(12) United States Patent
Ohgi et al.

(10) Patent No.: US 8,785,121 B2
(45) Date of Patent: Jul. 22, 2014

(54) SINGLE-STRANDED NUCLEIC ACID MOLECULE FOR CONTROLLING GENE EXPRESSION

(75) Inventors: Tadaaki Ohgi, Kurume (JP); Hirotake Hayashi, Kurume (JP); Hisao Shirohzu, Kurume (JP); Tomohiro Hamasaki, Kurume (JP); Akihiro Itoh, Kurume (JP); Hiroshi Suzuki, Kurume (JP)

(73) Assignee: BONAC Corporation, Fukuoka (JP)

(*) Notice: Subject to any disclaimer, the term of this patent is extended or adjusted under 35 U.S.C. 154(b) by 0 days.

(21) Appl. No.: 13/254,150

(22) PCT Filed: Jul. 8, 2011

(86) PCT No.: PCT/JP2011/065737
§ 371 (c)(1),
(2), (4) Date: Aug. 31, 2011

(87) PCT Pub. No.: WO2012/005368
PCT Pub. Date: Jan. 12, 2012

(65) Prior Publication Data
US 2012/0010271 A1    Jan. 12, 2012

(30) Foreign Application Priority Data

| Jul. 8, 2010 | (JP) | 2010-156122 |
| Aug. 3, 2010 | (JP) | 2010-174915 |
| Oct. 13, 2010 | (JP) | 2010-230806 |
| Oct. 13, 2010 | (JP) | 2010-230808 |
| Dec. 2, 2010 | (JP) | 2010-269823 |
| Dec. 2, 2010 | (JP) | 2010-269824 |

(51) Int. Cl.
| C12Q 1/68 | (2006.01) |
| C12P 19/34 | (2006.01) |
| C12N 15/63 | (2006.01) |
| C07H 21/02 | (2006.01) |
| C07H 21/04 | (2006.01) |

(52) U.S. Cl.
USPC ......... 435/6.1; 435/6.11; 435/6.12; 435/91.1; 435/91.31; 435/455; 514/44; 536/23.1; 536/24.5

(58) Field of Classification Search
USPC ............... 435/6, 91.1, 91.31, 455, 375, 6.1; 514/44; 536/23.1, 24.5, 24.3
See application file for complete search history.

(56) References Cited

U.S. PATENT DOCUMENTS

| 3,687,808 | A | 8/1972 | Merigan, Jr. |
| 7,595,301 | B2 | 9/2009 | Kunugiza et al. |
| 2002/0156261 | A1 | 10/2002 | Malvy et al. |
| 2003/0059789 | A1 | 3/2003 | Efimov et al. |
| 2004/0058886 | A1 | 3/2004 | Scaringe |
| 2006/0276421 | A1 | 12/2006 | Kunugiza et al. |
| 2010/0137407 | A1 | 6/2010 | Abe et al. |
| 2011/0052666 | A1 | 3/2011 | Kaemmerer et al. |
| 2011/0055965 | A1 | 3/2011 | Abe et al. |
| 2012/0135521 | A1* | 5/2012 | Eshleman et al. ............ 435/375 |

FOREIGN PATENT DOCUMENTS

| CN | 1860228 A | 11/2006 |
| CN | 101679962 A | 3/2010 |
| EP | 1669450 A1 | 6/2006 |
| EP | 2143792 A1 | 1/2010 |
| EP | 2233573 A1 | 9/2010 |
| EP | 1669450 B1 | 11/2011 |
| EP | 2562257 A1 | 2/2013 |
| JP | 2005-521393 A | 7/2005 |
| JP | 2008-278784 | 11/2008 |
| WO | 95/29241 A2 | 11/1995 |
| WO | 98/16550 A1 | 4/1998 |
| WO | 03/068798 A2 | 8/2003 |
| WO | 03/079757 A2 | 10/2003 |
| WO | 2004/015075 | 2/2004 |
| WO | 2004/090108 | 10/2004 |
| WO | 2005/019453 | 3/2005 |
| WO | 2006/074108 A2 | 7/2006 |
| WO | 2006/088490 A2 | 8/2006 |
| WO | 2008/116094 | 9/2008 |
| WO | 2008/140126 | 11/2008 |
| WO | 2009/000520 A1 | 12/2008 |
| WO | 2009/073809 | 6/2009 |
| WO | 2009/076321 A2 | 6/2009 |
| WO | 2009/102081 | 8/2009 |
| WO | 2011/132672 A1 | 10/2011 |

OTHER PUBLICATIONS

Abe et al., FEBS Letters, vol. 425, pp. 91-96 (1998).*
Nilsson et al, Science, vol. 265, pp. 2085-2088 (1994).*
Clusel et al, Nucliec Acids Res., vol. 21, No. 15, pp. 3405-3411 (1993).*
Hamazaki et al., Helvetica Chimica Acta, vol. 85, pp. 2183-2194 (2002).*
Fire et al., "Potent and specific genetic interference by double-stranded RNA in *Caenorhabditis elegans*", Nature, 1998, vol. 391, pp. 806-811.
Limbach et al., "Summary: the modified nucleosides of RNA", Nucleic Acids Research, 1994, vol. 22, No. 12, pp. 2183-2196.

(Continued)

*Primary Examiner* — Jane Zara
(74) *Attorney, Agent, or Firm* — Morgan, Lewis & Bockius LLP

(57) ABSTRACT

Provided is a novel nucleic acid molecule that is a single-stranded nucleic acid molecule including an expression inhibitory sequence that inhibits expression of a target gene. The single-stranded nucleic acid molecule includes, in sequence from the 5' side to the 3' side: a 5' side region (Xc); an inner region (Z); and a 3' side region (Yc). The inner region (Z) is composed of an inner 5' side region (X) and an inner 3' side region (Y) that are linked to each other. The 5' side region (Xc) is complementary to the inner 5' side region (X). The 3' side region (Yc) is complementary to the inner 3' side region (Y). At least one of the inner region (Z), the 5' side region (Xc), and the 3' side region (Yc) includes the expression inhibitory sequence.

30 Claims, 23 Drawing Sheets
(2 of 23 Drawing Sheet(s) Filed in Color)

(56) References Cited

OTHER PUBLICATIONS

Nykanen et al., "ATP Requirements and Small Interfering RNA Structure in the RNA Interference Pathway", Cell, 2001, vol. 107, pp. 309-321.

Teramoto et al., "Prediction of siRNA functionality using generalized string kernel and support vector machine", FEBS Letters, 2005, vol. 579, pp. 2878-2882.

Elbashir et al., "Functional anatomy of siRNAs for mediating efficient RNAi in *Drosophila melanogaster* embryo lysate", The EMBO Journal, 2001, vol. 20, No. 23, pp. 6877-6888.

Cheng et al., "TGF-β1 Gene Silencing for Treating Liver Fibrosis", Molecular Pharmaceutics, 2009, vol. 6, Iss.3, pp. 772-779.

Confalone, et al., "Design and Synthesis of Potential DNA Crosslinking Reagents Based on the Anthramycin Class of Minor Groove Binding Compounds", J. Org. Chem., 1988, vol. 53, pp. 482-487.

Oliveira, et al., "Efficient and Expeditious Protocols for the Synthesis of Racemic and Enantiomerically Pure Endocyclic Enecarbamates from *N*-Acyl Lactams and *N*-Acyl Pyrrolidines", J. Org. Chem., 1999, vol. 64, pp. 6646-6652.

Püschl, et al., "Pyrrolidine PNA: A Novel Conformationally Restricted PNA Analogue", Org. Lett., 2000, vol. 2, No. 6, pp. 4161-4163.

Anderson et al., "Bispecific Short Hairpin siRNA Constructs Targeted to CD4, CXCR4. and CCR5 Confer HIV-1 Resistance," Oligonucleotides, 13: 303-312 (2003).

Kumar et al, "Pyrrolidine Nucleic Acids: DNA/PNA Oligomers with 2-Hydroxy/Aminomethyl-4-(thymin-l-yl)pyrrolidine-N-acetic acid," Organic Letters, 3: 1269-1272 (2001).

Lonkar et al.. "Design and synthesis of conformationally frozen peptide nucleic acid backbone: chiral piperidine PNA as a hexitol nucleic acid surrogate," Bioorganic & Medicinal Chemistry Letters, 14: 2147-2149 (2004).

Supplementary European Search Report issued in corresponding European Application No. 746147.5 dated Mar. 26, 2012.

Office Action issued in corresponding European Application No. 11746147.5 dated Apr. 20, 2012.

Office Action issued in related European Application No. 11748250.5 dated May 29, 2012.

Supplementary European Search Report issued in related European Application No. 11748260.5 dated Apr. 5, 2012.

Leirdal et al., "Gene silencing in mammalian cells by preformed small RNA duplexes", Biochem. Biophys. Res. Commun., 2002, vol. 295, pp. 744-748.

Bramsen et al., "Improved silencing properties using small internally segmented interfering RNAs", Nucleic Acids Res., 2007, vol. 35, No. 17, pp. 5886-5897.

Yamaka Wa et al., "Properties and Anti-HIV Activity of Nicked Dumbbell Oligonucleotides", Nucleosides & Nucleotides, 1996, vol. 15(1-3), pp. 519-529.

Hosoya et al., "Sequence-specific inhibition of a transcription factor by circular dumbbell DNA oligonucleotides", FEBS Lett., 1999, vol. 461, pp. 136-140.

Kunugiza et al., "Inhibitory effect of ribbon-type NF-kappaB decoy oligodeoxynucleotides on osteoclast induction and activity in vitro and in vivo ", Arthritis Res. Ther., 2006, vol. 8, No. 4, R103, pp. 1-10.

Abe et al., "Dumbbell-Shaped Nanocircular RNAs for RNA Interference", J. Am. Chem. Soc., 2007, vol. 129, pp. 15108-15109.

Supplemental structure search results accompanying WO 2009/000520.

Office Action issued in corresponding European Patent Application No. 11746147.5 dated Sep. 26, 2012.

Office Action issued in corresponding European Patent Application No. 11746147.5 dated Mar. 25, 2013.

Yu et al., "RNA interference by expression of short-interfering RNAs and hairpin RNAs in mammalian cells," Proceedings of the National Academy of Sciences, 99: 6047-6052 (2002).

Paddison et al., "Short hairpin RNAs (shRNAs) induce sequence-specific silencing in mammalian cells," Genes & Development, 16: 948-958 (2002).

McAnuff et al., "Potency of siRNA Versus shRNA Mediated Knockdown In Vivo," Journal of Pharmaceutical Sciences, 96: 2922-2930 (2007).

Search Report issued in related International Patent Application No. PCT/JP2012/080461 dated Jan. 22, 2013.

Partial European Search Report issued in related European Divisional Patent Application No. 13167541.5 dated Jul. 31, 2013.

Bosi et al., "Antimycobacterial Activity of Ionic Fullerene Derivatives," Bioorganic & Medical Chemistry Letters, 10: 1043-1045 (2013).

Office Action issued in corresponding Chinese Patent Application No. 201180027223.1 dated Nov. 21, 2013.

Extended European Search Report issued in related European Patent Application No. 13184178.5 dated Oct. 24, 2013.

Office Action issued in related U.S. Appl. No. 13/254,159 dated Nov. 21, 2012.

Supplemental structure search results accompanying WO 2009/000520, Oct. 2012.

* cited by examiner ssRNA (−)

NK-0035 (+)

NK-0033 (+)

| | Xc/Yc | | | |
|---|---|---|---|---|
| NK-0036 | 25/1 | 5'- aaccaugaugaaguauucaacaagcGGCUGUUGUCAUAACUUCUCAUGUUCUUCg -3' | SEQ ID NO: 51 |
| NK-0025 | 24/1 | 5'- accaugaugaaguauucaacaagccCCACACCGGCUGUUGUCAUAACUUCUCAUGUUCUUCg -3' | SEQ ID NO: 52 |
| NK-0037 | 23/2 | 5'- ccaugagaaguaugcaacaagccCCACACCGGCUGUUGUCAUACUUCUCAUCUCAUGUUCUUCga -3' | SEQ ID NO: 53 |
| NK-0016 | 22/3 | 5'- caugagaaguaugcaacaagcCCACACCGGCUGUUGUCAUACUUCUCAUCUCAUGGUUCUUCga -3' | SEQ ID NO: 2 |
| NK-0038 | 21/4 | 5'- augagaaguaugcaacaagcCCACACCGGCUGUUGUCAUACUUCUCAUCUCAUGGUUCUUCgaa -3' | SEQ ID NO: 54 |
| NK-0026 | 20/5 | 5'- ugagaaguaugcaacaagcCCACACCGGCUGUUGUCAUACUUCUCAUCUCAUGGUUCUUCgaac -3' | SEQ ID NO: 55 |
| NK-0027 | 18/7 | 5'- agaaguaugcaacaagcCCACACCGGCUGUUGUCAUACUCUCAUGUUCUUCgaaccau -3' | SEQ ID NO: 56 |
| NK-0028 | 16/9 | 5'- aaguaugcaacaagcCCACACCGGCUGUUGUCAUACUUCUCAUCUCAUGGUUCUUCgaaccauga -3' | SEQ ID NO: 57 |
| NK-0029 | 14/11 | 5'- guaugcaacaagcCCACACCGGCUGUUGUCAUACUUCUCAUGGUUCUUCgaaccaugaga -3' | SEQ ID NO: 58 |
| NK-0014 | 12/13 | 5'- augcaacaagcCCACACCGGCUGUUGUCAUACUUCUCAUCUCAUGGUUCUUCgaaccaugagaag -3' | SEQ ID NO: 14 |
| NK-0030 | 9/16 | 5'- caacaagcCCACACCGGCUGUUGUCAUACUUCUCAUGGUUCUUCgaaccaugagaaguau -3' | SEQ ID NO: 59 |
| NK-0031 | 7/18 | 5'- acaagcCCACACCGGCUGUUGUCAUACUUCUCAUGGUUCUUCgaaccaugagaaguauga -3' | SEQ ID NO: 60 |
| NK-0020 | 5/20 | 5'- aagcCCACACCGGCUGUUGUCAUACUUCUCAUGGUUCUUCgaaccaugagaaguaugaca -3' | SEQ ID NO: 61 |
| NK-0019 | 4/21 | 5'- agcCCACACCGGCUGUUGUCAUACUUCUCAUGGUUCUUCgaaccaugagaaguaugacaa -3' | SEQ ID NO: 7 |
| NK-0018 | 3/22 | 5'- gcCCACACCGGCUGUUGUCAUACUUCUCAUGGUUCUUCgaaccaugagaaguaugacaac -3' | SEQ ID NO: 62 |
| NK-0039 | 2/23 | 5'- cCCACACCGGCUGUUGUCAUACUUCUCAUGGUUCUUCgaaccaugagaaguaugacaaca -3' | SEQ ID NO: 63 |
| NK-0032 | 1/24 | 5'- CCACACCGGCUGUUGUCAUACUUCUCAUGGUUCUUCgaaccaugagaaguaugacaacag -3' | SEQ ID NO: 64 |
| NK-0040 | 1/25 | 5'- CCACACCGGCUGUUGUCAUACUUCUCAUGGUUCUUCgaaccaugagaaguaugacaacagc -3' | SEQ ID NO: 65 |

FIG. 21

| Xc+Yc/X+Y | | | |
|---|---|---|---|
| NK-0047 | 26/27 | 5' - accaugaaguaugacaacagcCCACACCGGCUGUUGUCAUACUUCUCAUGGUUCGuuCGg - 3' | SEQ ID NO: 66 |
| NK-0025 | 25/26 | 5' - accaugaaguaugacaacagcCCACACCGGCUGUUGUCAUACUUCUCAUGGUUCGUUCGg - 3' | SEQ ID NO: 52 |
| NK-0048 | 24/25 | 5' - accaugaaguaugacaacagcCCACACCGCUGUUGUCAUACUUCUCAUGGUUCGUUCGg - 3' | SEQ ID NO: 67 |
| NK-0049 | 23/24 | 5' - ccaucagaaguaugacaacagcCCACACCGCUGUUGUCAUACUUCUCAUGGUUCuuCGg - 3' | SEQ ID NO: 68 |
| NK-0050 | 23/24 | 5' - accaugagaaguaugacaacagCCACACCCUGUUGUCAUACUUCUCAUGGUUCuuCGa - 3' | SEQ ID NO: 69 |
| NK-0051 | 22/23 | 5' - ccaucagaaguaugacaacagcCCACACCCUGUUGUCAUACUUCUCAUGGUUCuuCGa - 3' | SEQ ID NO: 70 |
| NK-0052 | 21/22 | 5' - ccaugagaaguaugacaacagcCCACACCCUGUUGUCAUACUUCUCAUGGUuuuCGa - 3' | SEQ ID NO: 71 |
| NK-0053 | 21/22 | 5' - ccaucagaaguaugacaacagCCACACCCUGUUGUCAUACUUCUCAUGGUuuuCGa - 3' | SEQ ID NO: 72 |
| NK-0054 | 20/21 | 5' - caucagaaguaugacaacagcCCACACCCUGUUGUCAUACUUCUCAUGGUuuCGa - 3' | SEQ ID NO: 73 |

FIG. 23

```
         Xc/X
NK-0001  25/25  5'- aacuauagaaguauaacaaacaagcuCCACACCGGCUGUGUCAUACUUCUCAUGGUCUUCGg -3'   SEQ ID NO: 74
                                                                         **
NK-0002  23/25  5'- ccaugagaaguaugacaaacagagccCCACACCGGCUGUGUCAUACUUCUCAUGGUCUUCGg -3'   SEQ ID NO: 75
                                                                       ** *
NK-0003  22/25  5'- caugagagauugacaaacagccCCACACCGGCUGUUGUCAUACUUCUCAUGGUUCUUCGg -3'    SEQ ID NO: 76
```

FIG. 25

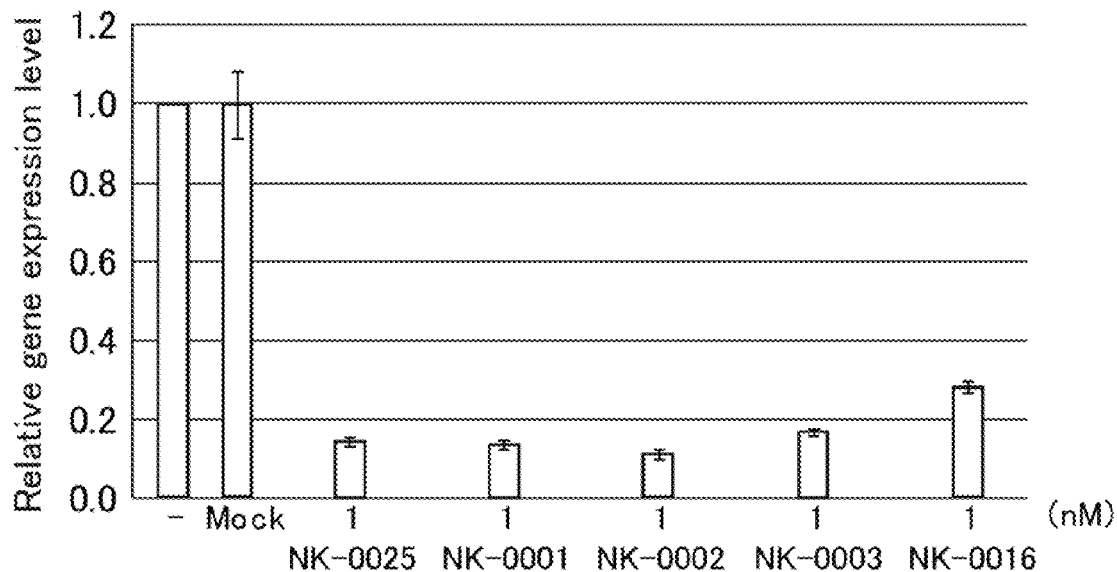
FIG. 26
NK-0079(SEQ ID NO: 77)Lx/Ly=4/7
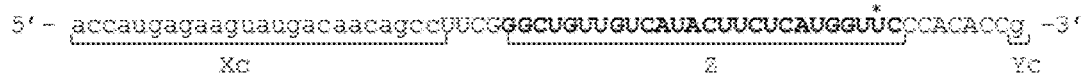
NK-0080(SEQ ID NO: 78)Lx/Ly=1/1
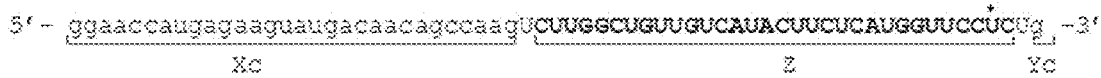
NK-0081(SEQ ID NO: 79)Lx/Ly=0/0
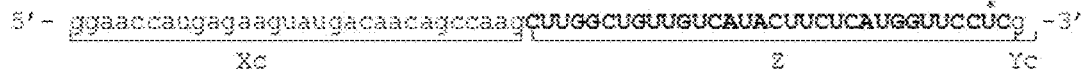
NK-0082(SEQ ID NO: 8)Lx/Ly=4/3
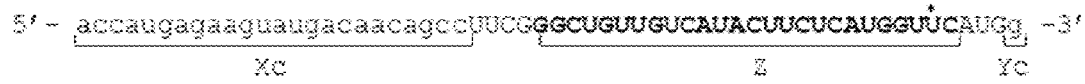
NK-0083(SEQ ID NO: 37)Lx/Ly=9/3
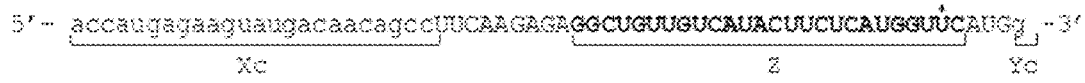
FIG. 27

```
                           SEQUENCE LISTING

<160> NUMBER OF SEQ ID NOS: 80

<210> SEQ ID NO 1
<211> LENGTH: 19
<212> TYPE: RNA
<213> ORGANISM: Artificial
<220> FEATURE:
<223> OTHER INFORMATION: siRNA

<400> SEQUENCE: 1
guugucauac uucucaugg                                                    19

<210> SEQ ID NO 2
<211> LENGTH: 62
<212> TYPE: RNA
<213> ORGANISM: Artificial
<220> FEATURE:
<223> OTHER INFORMATION: nucleic acid molecule

<400> SEQUENCE: 2
caugagaagu augacaacag ccccacaccg gcuguuguca uacuucucau gguucuucgg        60
aa                                                                      62

<210> SEQ ID NO 3
<211> LENGTH: 21
<212> TYPE: RNA
<213> ORGANISM: Artificial
<220> FEATURE:
<223> OTHER INFORMATION: sense

<400> SEQUENCE: 3
ccaugagaag uaugacaaca g                                                 21

<210> SEQ ID NO 4
<211> LENGTH: 21
<212> TYPE: RNA
<213> ORGANISM: Artificial
<220> FEATURE:
<223> OTHER INFORMATION: antisense

<400> SEQUENCE: 4
guugucauac uucucauggu u                                                 21

<210> SEQ ID NO 5
<211> LENGTH: 19
<212> TYPE: RNA
<213> ORGANISM: Artificial
<220> FEATURE:
<223> OTHER INFORMATION: siRNA

<400> SEQUENCE: 5
auuguaacga gacaaacac                                                    19

<210> SEQ ID NO 6
<211> LENGTH: 19
<212> TYPE: RNA
<213> ORGANISM: Artificial
<220> FEATURE:
<223> OTHER INFORMATION: siRNA

<400> SEQUENCE: 6
uugcgcuuuu uggugacgc                                                    19
```

<210> SEQ ID NO 7
<211> LENGTH: 62
<212> TYPE: RNA
<213> ORGANISM: Artificial
<220> FEATURE:
<223> OTHER INFORMATION: nucleic acid molecule

<400> SEQUENCE: 7
agccccacac cggcuguugu cauacuucuc augguucuuc ggaaccauga gaaguaugac      60
aa                                                                    62

<210> SEQ ID NO 8
<211> LENGTH: 58
<212> TYPE: RNA
<213> ORGANISM: Artificial
<220> FEATURE:
<223> OTHER INFORMATION: nucleic acid molecule

<400> SEQUENCE: 8
accaugagaa guaugacaac agccuucggg cuguugucau acuucucaug guucaugg        58

<210> SEQ ID NO 9
<211> LENGTH: 23
<212> TYPE: DNA
<213> ORGANISM: Artificial
<220> FEATURE:
<223> OTHER INFORMATION: primer

<400> SEQUENCE: 9
ggagaaggct ggggctcatt tgc                                             23

<210> SEQ ID NO 10
<211> LENGTH: 23
<212> TYPE: DNA
<213> ORGANISM: Artificial
<220> FEATURE:
<223> OTHER INFORMATION: primer

<400> SEQUENCE: 10
tggccagggg tgctaagcag ttg                                             23

<210> SEQ ID NO 11
<211> LENGTH: 23
<212> TYPE: DNA
<213> ORGANISM: Artificial
<220> FEATURE:
<223> OTHER INFORMATION: primer

<400> SEQUENCE: 11
gccacggctg cttccagctc ctc                                             23

<210> SEQ ID NO 12
<211> LENGTH: 25
<212> TYPE: DNA
<213> ORGANISM: Artificial
<220> FEATURE:
<223> OTHER INFORMATION: primer

<400> SEQUENCE: 12
aggtctttgc ggatgtccac gtcac                                           25

<210> SEQ ID NO 13
<211> LENGTH: 51
<212> TYPE: RNA
<213> ORGANISM: Artificial

```
<220> FEATURE:
<223> OTHER INFORMATION: nucleic acid molecule

<400> SEQUENCE: 13
caugagaagu augacaacag ccggcuguug ucauacuucu caugguucga a            51

<210> SEQ ID NO 14
<211> LENGTH: 62
<212> TYPE: RNA
<213> ORGANISM: Artificial
<220> FEATURE:
<223> OTHER INFORMATION: nucleic acid molecule

<400> SEQUENCE: 14
augacaacag ccccacaccg gcuguuguca uacuucucau gguucuucgg aaccaugaga   60
ag                                                                 62

<210> SEQ ID NO 15
<211> LENGTH: 62
<212> TYPE: RNA
<213> ORGANISM: Artificial
<220> FEATURE:
<223> OTHER INFORMATION: nucleic acid molecule

<400> SEQUENCE: 15
ugucagugcu cauuuacaag ccccacaccg gcuuguaaau gagcacugac acuucuucgg   60
aa                                                                 62

<210> SEQ ID NO 16
<211> LENGTH: 21
<212> TYPE: RNA
<213> ORGANISM: Artificial
<220> FEATURE:
<223> OTHER INFORMATION: siRNA

<400> SEQUENCE: 16
aaagucaaug uacagcugcu u                                            21

<210> SEQ ID NO 17
<211> LENGTH: 24
<212> TYPE: DNA
<213> ORGANISM: Artificial
<220> FEATURE:
<223> OTHER INFORMATION: primer

<400> SEQUENCE: 17
ccattgctgt cccgtgcaga gctg                                         24

<210> SEQ ID NO 18
<211> LENGTH: 25
<212> TYPE: DNA
<213> ORGANISM: Artificial
<220> FEATURE:
<223> OTHER INFORMATION: primer

<400> SEQUENCE: 18
atggtagccc ttgggctcgt ggatc                                        25

<210> SEQ ID NO 19
<211> LENGTH: 24
<212> TYPE: DNA
<213> ORGANISM: Artificial
<220> FEATURE:
<223> OTHER INFORMATION: primer
```

```
<400> SEQUENCE: 19
gtcgtaccac aggcattgtg atgg                                              24

<210> SEQ ID NO 20
<211> LENGTH: 22
<212> TYPE: DNA
<213> ORGANISM: Artificial
<220> FEATURE:
<223> OTHER INFORMATION: primer

<400> SEQUENCE: 20
gcaatgcctg ggtacatggt gg                                                22

<210> SEQ ID NO 21
<211> LENGTH: 25
<212> TYPE: DNA
<213> ORGANISM: Artificial
<220> FEATURE:
<223> OTHER INFORMATION: primer

<400> SEQUENCE: 21
cccttattga cctcaactac atggt                                             25

<210> SEQ ID NO 22
<211> LENGTH: 23
<212> TYPE: DNA
<213> ORGANISM: Artificial
<220> FEATURE:
<223> OTHER INFORMATION: primer

<400> SEQUENCE: 22
gaggggccat ccacagtctt ctg                                               23

<210> SEQ ID NO 23
<211> LENGTH: 21
<212> TYPE: DNA
<213> ORGANISM: Artificial
<220> FEATURE:
<223> OTHER INFORMATION: primer

<400> SEQUENCE: 23
actccacgtg gaaatcaacg g                                                 21

<210> SEQ ID NO 24
<211> LENGTH: 20
<212> TYPE: DNA
<213> ORGANISM: Artificial
<220> FEATURE:
<223> OTHER INFORMATION: primer

<400> SEQUENCE: 24
tagtagacga tgggcagtgg                                                   20

<210> SEQ ID NO 25
<211> LENGTH: 22
<212> TYPE: DNA
<213> ORGANISM: Artificial
<220> FEATURE:
<223> OTHER INFORMATION: primer

<400> SEQUENCE: 25
atggctagrc tctgtgcttc ct                                                22

<210> SEQ ID NO 26
<211> LENGTH: 24
```

```
<212> TYPE: DNA
<213> ORGANISM: Artificial
<220> FEATURE:
<223> OTHER INFORMATION: primer

<400> SEQUENCE: 26
agggctctcc agayttctgc tctg                                              24

<210> SEQ ID NO 27
<211> LENGTH: 21
<212> TYPE: DNA
<213> ORGANISM: Artificial
<220> FEATURE:
<223> OTHER INFORMATION: primer

<400> SEQUENCE: 27
catcaactat aagcagctcc a                                                 21

<210> SEQ ID NO 28
<211> LENGTH: 21
<212> TYPE: DNA
<213> ORGANISM: Artificial
<220> FEATURE:
<223> OTHER INFORMATION: primer

<400> SEQUENCE: 28
ttcaagtgga gagcagttca g                                                 21

<210> SEQ ID NO 29
<211> LENGTH: 61
<212> TYPE: RNA
<213> ORGANISM: Artificial
<220> FEATURE:
<223> OTHER INFORMATION: nucleic acid molecule

<400> SEQUENCE: 29
agcuguacau ugacuuuagc cccacaccgg cuaaagucaa uguacagcug cuucuucgga       60
a                                                                       61

<210> SEQ ID NO 30
<211> LENGTH: 62
<212> TYPE: RNA
<213> ORGANISM: Artificial
<220> FEATURE:
<223> OTHER INFORMATION: nucleic acid molecule

<400> SEQUENCE: 30
agcagcugua cauugacuuu agccccacac cggcuaaagu caauguacag cugcuucuuc       60
gg                                                                      62

<210> SEQ ID NO 31
<211> LENGTH: 61
<212> TYPE: RNA
<213> ORGANISM: Artificial
<220> FEATURE:
<223> OTHER INFORMATION: nucleic acid molecule

<400> SEQUENCE: 31
gcagcuguac auugacuuua gccccacacc ggcuaaaguc aauguacagc ugcuucuucg       60
g                                                                       61

<210> SEQ ID NO 32
<211> LENGTH: 51
<212> TYPE: RNA
```

```
<213> ORGANISM: Artificial
<220> FEATURE:
<223> OTHER INFORMATION: nucleic acid molecule

<400> SEQUENCE: 32
cagcuguaca uugacuuuag ccggcuaaag ucaauguaca gcugcuucga a          51

<210> SEQ ID NO 33
<211> LENGTH: 50
<212> TYPE: RNA
<213> ORGANISM: Artificial
<220> FEATURE:
<223> OTHER INFORMATION: nucleic acid molecule

<400> SEQUENCE: 33
agcuguacau ugacuuuagc cggcuaaagu caauguacag cugcuucgaa            50

<210> SEQ ID NO 34
<211> LENGTH: 51
<212> TYPE: RNA
<213> ORGANISM: Artificial
<220> FEATURE:
<223> OTHER INFORMATION: nucleic acid molecule

<400> SEQUENCE: 34
agcagcugua cauugacuuu agccggcuaa agucaaugua cagcugcuuc g          51

<210> SEQ ID NO 35
<211> LENGTH: 50
<212> TYPE: RNA
<213> ORGANISM: Artificial
<220> FEATURE:
<223> OTHER INFORMATION: nucleic acid molecule

<400> SEQUENCE: 35
gcagcuguac auugacuuua gccggcuaaa gucaauguac agcugcuucg            50

<210> SEQ ID NO 36
<211> LENGTH: 51
<212> TYPE: RNA
<213> ORGANISM: Artificial
<220> FEATURE:
<223> OTHER INFORMATION: nucleic acid molecule

<400> SEQUENCE: 36
ugucagugcu cauuuacaag ccggcuugua aaugagcacu gacacuucga a          51

<210> SEQ ID NO 37
<211> LENGTH: 63
<212> TYPE: RNA
<213> ORGANISM: Artificial
<220> FEATURE:
<223> OTHER INFORMATION: nucleic acid molecule

<400> SEQUENCE: 37
accaugagaa guaugacaac agccuucaag agaggcuguu gucauacuuc ucaugguuca    60
ugg                                                                 63

<210> SEQ ID NO 38
<211> LENGTH: 51
<212> TYPE: RNA
<213> ORGANISM: Artificial
<220> FEATURE:
<223> OTHER INFORMATION: nucleic acid molecule

<400> SEQUENCE: 38
```

```
ccaucaacga uaagugaaag ccggcuuuca cuuaucguug auggcuucga a        51
```

```
<210> SEQ ID NO 39
<211> LENGTH: 21
<212> TYPE: RNA
<213> ORGANISM: Artificial
<220> FEATURE:
<223> OTHER INFORMATION: sense

<400> SEQUENCE: 39
gcagcuguac auugacuuua g                                        21

<210> SEQ ID NO 40
<211> LENGTH: 21
<212> TYPE: RNA
<213> ORGANISM: Artificial
<220> FEATURE:
<223> OTHER INFORMATION: antisense

<400> SEQUENCE: 40
aaagucaaug uacagcugcu u                                        21

<210> SEQ ID NO 41
<211> LENGTH: 21
<212> TYPE: RNA
<213> ORGANISM: Artificial
<220> FEATURE:
<223> OTHER INFORMATION: sense

<400> SEQUENCE: 41
gugucagugc ucauuuacaa g                                        21

<210> SEQ ID NO 42
<211> LENGTH: 21
<212> TYPE: RNA
<213> ORGANISM: Artificial
<220> FEATURE:
<223> OTHER INFORMATION: antisense

<400> SEQUENCE: 42
uguaaaugag cacugacacu u                                        21

<210> SEQ ID NO 43
<211> LENGTH: 62
<212> TYPE: RNA
<213> ORGANISM: Artificial
<220> FEATURE:
<223> OTHER INFORMATION: nucleic acid molecule

<400> SEQUENCE: 43
uguuugucuc guuacaauau ccccacaccg gauauuguaa cgagacaaac acuccuucgg   60
ga                                                                 62

<210> SEQ ID NO 44
<211> LENGTH: 62
<212> TYPE: RNA
<213> ORGANISM: Artificial
<220> FEATURE:
<223> OTHER INFORMATION: nucleic acid molecule

<400> SEQUENCE: 44
aguguuuguc ucguuacaau auccccacac cggauauugu aacgagacaa acacuccuuc   60
gg                                                                 62
```

```
<210> SEQ ID NO 45
<211> LENGTH: 23
<212> TYPE: DNA
<213> ORGANISM: Artificial
<220> FEATURE:
<223> OTHER INFORMATION: primer

<400> SEQUENCE: 45
aaagctgcca atgcccctcg acc                                              23

<210> SEQ ID NO 46
<211> LENGTH: 22
<212> TYPE: DNA
<213> ORGANISM: Artificial
<220> FEATURE:
<223> OTHER INFORMATION: primer

<400> SEQUENCE: 46
taggtgggtg gccctcgtct tg                                               22

<210> SEQ ID NO 47
<211> LENGTH: 62
<212> TYPE: RNA
<213> ORGANISM: Artificial
<220> FEATURE:
<223> OTHER INFORMATION: nucleic acid molecule

<400> SEQUENCE: 47
cgucaccaaa aagcgcaauu ccccacaccg gaauugcgcu uuuggugac gcuucuucgg        60 aa                                                                     62

<210> SEQ ID NO 48
<211> LENGTH: 62
<212> TYPE: RNA
<213> ORGANISM: Artificial
<220> FEATURE:
<223> OTHER INFORMATION: nucleic acid molecule

<400> SEQUENCE: 48
agcgucacca aaaagcgcaa uuccccacac cggaauugcg cuuuuuggug acgcuucuuc       60
gg                                                                     62

<210> SEQ ID NO 49
<211> LENGTH: 24
<212> TYPE: DNA
<213> ORGANISM: Artificial
<220> FEATURE:
<223> OTHER INFORMATION: primer

<400> SEQUENCE: 49
ctggacatca agctggccct ggac                                             24

<210> SEQ ID NO 50
<211> LENGTH: 24
<212> TYPE: DNA
<213> ORGANISM: Artificial
<220> FEATURE:
<223> OTHER INFORMATION: primer

<400> SEQUENCE: 50
caccagcttg cgcatggcca cttc                                             24

<210> SEQ ID NO 51
<211> LENGTH: 62
```

```
<212> TYPE: RNA
<213> ORGANISM: Artificial
<220> FEATURE:
<223> OTHER INFORMATION: nucleic acid molecule

<400> SEQUENCE: 51
aaccaugaga aguaugacaa cagccccaca ccggcuguug ucauacuucu caugguucuu    60
cg                                                                  62

<210> SEQ ID NO 52
<211> LENGTH: 62
<212> TYPE: RNA
<213> ORGANISM: Artificial
<220> FEATURE:
<223> OTHER INFORMATION: nucleic acid molecule

<400> SEQUENCE: 52
accaugagaa guaugacaac agccccacac cggcuguugu cauacuucuc augguucuuc    60
gg                                                                  62

<210> SEQ ID NO 53
<211> LENGTH: 62
<212> TYPE: RNA
<213> ORGANISM: Artificial
<220> FEATURE:
<223> OTHER INFORMATION: nucleic acid molecule

<400> SEQUENCE: 53
ccaugagaag uaugacaaca gccccacacc ggcuguuguc auacuucuca ugguucuucg    60
ga                                                                  62

<210> SEQ ID NO 54
<211> LENGTH: 62
<212> TYPE: RNA
<213> ORGANISM: Artificial
<220> FEATURE:
<223> OTHER INFORMATION: nucleic acid molecule

<400> SEQUENCE: 54
augagaagua ugacaacagc cccacaccgg cuguugucau acuucucaug guucuucgga    60
ac                                                                  62

<210> SEQ ID NO 55
<211> LENGTH: 62
<212> TYPE: RNA
<213> ORGANISM: Artificial
<220> FEATURE:
<223> OTHER INFORMATION: nucleic acid molecule

<400> SEQUENCE: 55
ugagaaguau gacaacagcc ccacaccggc uguugucaua cuucucaugg uucuucggaa    60
cc                                                                  62

<210> SEQ ID NO 56
<211> LENGTH: 62
<212> TYPE: RNA
<213> ORGANISM: Artificial
<220> FEATURE:
<223> OTHER INFORMATION: nucleic acid molecule

<400> SEQUENCE: 56
agaaguauga caacagcccc acaccggcug uugucauacu ucucaugguu cuucggaacc    60
``` au                                                                      62

<210> SEQ ID NO 57
<211> LENGTH: 62
<212> TYPE: RNA
<213> ORGANISM: Artificial
<220> FEATURE:
<223> OTHER INFORMATION: nucleic acid molecule

<400> SEQUENCE: 57
aaguaugaca acagccccac accggcuguu gucauacuuc ucaugguucu ucggaaccau        60
ga                                                                      62

<210> SEQ ID NO 58
<211> LENGTH: 62
<212> TYPE: RNA
<213> ORGANISM: Artificial
<220> FEATURE:
<223> OTHER INFORMATION: nucleic acid molecule

<400> SEQUENCE: 58
guaugacaac agccccacac cggcuguugu cauacuucuc augguucuuc ggaaccauga        60
ga                                                                      62

<210> SEQ ID NO 59
<211> LENGTH: 62
<212> TYPE: RNA
<213> ORGANISM: Artificial
<220> FEATURE:
<223> OTHER INFORMATION: nucleic acid molecule

<400> SEQUENCE: 59
acaacagccc cacaccggcu guugucauac uucucauggu cuucggaac caugagaagu         60 au                                                                      62

<210> SEQ ID NO 60
<211> LENGTH: 62
<212> TYPE: RNA
<213> ORGANISM: Artificial
<220> FEATURE:
<223> OTHER INFORMATION: nucleic acid molecule

<400> SEQUENCE: 60
aacagcccca caccggcugu ugucauacuu cucaugguuc uucggaacca ugagaaguau        60
ga                                                                      62

<210> SEQ ID NO 61
<211> LENGTH: 62
<212> TYPE: RNA
<213> ORGANISM: Artificial
<220> FEATURE:
<223> OTHER INFORMATION: nucleic acid molecule

<400> SEQUENCE: 61
cagccccaca ccggcuguug ucauacuucu caugguucuu cggaaccaug agaaguauga       60
ca                                                                      62

<210> SEQ ID NO 62
<211> LENGTH: 62
<212> TYPE: RNA
<213> ORGANISM: Artificial
<220> FEATURE:
<223> OTHER INFORMATION: nucleic acid molecule

<400> SEQUENCE: 62
gccccacacc ggcuguuguc auacuucuca ugguucuucg gaaccaugag aaguaugaca       60
ac                                                                    62

<210> SEQ ID NO 63
<211> LENGTH: 62
<212> TYPE: RNA
<213> ORGANISM: Artificial
<220> FEATURE:
<223> OTHER INFORMATION: nucleic acid molecule

<400> SEQUENCE: 63
ccccacaccg gcuguuguca uacuucucau gguucuucgg aaccaugaga aguaugacaa       60
ca                                                                    62

<210> SEQ ID NO 64
<211> LENGTH: 62
<212> TYPE: RNA
<213> ORGANISM: Artificial
<220> FEATURE:
<223> OTHER INFORMATION: nucleic acid molecule

<400> SEQUENCE: 64
cccacaccgg cugugucau acuucucaug guucuucgga accaugagaa guaugacaac       60
ag                                                                    62

<210> SEQ ID NO 65
<211> LENGTH: 62
<212> TYPE: RNA
<213> ORGANISM: Artificial
<220> FEATURE:
<223> OTHER INFORMATION: nucleic acid molecule

<400> SEQUENCE: 65
ccacaccggc uguugucaua cuucucaugg uucuucggaa ccaugagaag uaugacaaca       60
gc                                                                    62

<210> SEQ ID NO 66
<211> LENGTH: 64
<212> TYPE: RNA
<213> ORGANISM: Artificial
<220> FEATURE:
<223> OTHER INFORMATION: nucleic acid molecule

<400> SEQUENCE: 66
aaccaugaga aguaugacaa cagccccaca ccggcuguug ucauacuucu cagguucgu       60 ucgc                                                                  64

<210> SEQ ID NO 67
<211> LENGTH: 60
<212> TYPE: RNA
<213> ORGANISM: Artificial
<220> FEATURE:
<223> OTHER INFORMATION: nucleic acid molecule

<400> SEQUENCE: 67
accaugagaa guaugacaac agcccacacc ggcuguguca uacuucucau gguucuucgg       60

<210> SEQ ID NO 68
<211> LENGTH: 58
<212> TYPE: RNA

```
<213> ORGANISM: Artificial
<220> FEATURE:
<223> OTHER INFORMATION: nucleic acid molecule

<400> SEQUENCE: 68
ccaugagaag uaugacaaca gcccacaccg cuguugucau acuucucaug guuuucga      58

<210> SEQ ID NO 69
<211> LENGTH: 58
<212> TYPE: RNA
<213> ORGANISM: Artificial
<220> FEATURE:
<223> OTHER INFORMATION: nucleic acid molecule

<400> SEQUENCE: 69
accaugagaa guaugacaac agccacaccc uguugcaua cuucucaugg uucuucgg       58

<210> SEQ ID NO 70
<211> LENGTH: 56
<212> TYPE: RNA
<213> ORGANISM: Artificial
<220> FEATURE:
<223> OTHER INFORMATION: nucleic acid molecule

<400> SEQUENCE: 70
ccaugagaag uaugacaaca gccacacccu guugucauac uucucauggu uuucga        56

<210> SEQ ID NO 71
<211> LENGTH: 54
<212> TYPE: RNA
<213> ORGANISM: Artificial
<220> FEATURE:
<223> OTHER INFORMATION: nucleic acid molecule

<400> SEQUENCE: 71
caugagaagu augacaacag ccacacccug uugcauacu ucucaugguu ucga           54

<210> SEQ ID NO 72
<211> LENGTH: 54
<212> TYPE: RNA
<213> ORGANISM: Artificial
<220> FEATURE:
<223> OTHER INFORMATION: nucleic acid molecule

<400> SEQUENCE: 72
ccaugagaag uaugacaaca ccacaccugu ugcauacuu cucaugguuu ucga           54

<210> SEQ ID NO 73
<211> LENGTH: 52
<212> TYPE: RNA
<213> ORGANISM: Artificial
<220> FEATURE:
<223> OTHER INFORMATION: nucleic acid molecule

<400> SEQUENCE: 73
caugagaagu augacaacac cacaccuguu gucauacuuc ucaugguuuc ga            52

<210> SEQ ID NO 74
<211> LENGTH: 63
<212> TYPE: RNA
<213> ORGANISM: Artificial
<220> FEATURE:
<223> OTHER INFORMATION: nucleic acid molecule

<400> SEQUENCE: 74
aaccaugaga aguaugacaa cagccccaca ccggcuguug ucauacuucu cauggguucuu   60
```

```
cgg                                                              63

<210> SEQ ID NO 75
<211> LENGTH: 61
<212> TYPE: RNA
<213> ORGANISM: Artificial
<220> FEATURE:
<223> OTHER INFORMATION: nucleic acid molecule

<400> SEQUENCE: 75
ccaugagaag uaugacaaca gccccacacc ggcuguuguc auacuucuca ugguucuucg   60
g                                                                61

<210> SEQ ID NO 76
<211> LENGTH: 60
<212> TYPE: RNA
<213> ORGANISM: Artificial
<220> FEATURE:
<223> OTHER INFORMATION: nucleic acid molecule

<400> SEQUENCE: 76
caugagaagu augacaacag ccccacaccg gcuguuguca uacuucucau gguucuucgg   60

<210> SEQ ID NO 77
<211> LENGTH: 62
<212> TYPE: RNA
<213> ORGANISM: Artificial
<220> FEATURE:
<223> OTHER INFORMATION: nucleic acid molecule

<400> SEQUENCE: 77
accaugagaa guaugacaac agccuucggg cuguugucau acuucucaug guucccacac   60
cg                                                               62

<210> SEQ ID NO 78
<211> LENGTH: 65
<212> TYPE: RNA
<213> ORGANISM: Artificial
<220> FEATURE:
<223> OTHER INFORMATION: nucleic acid molecule

<400> SEQUENCE: 78
ggaaccauga gaaguaugac aacagccaag ucuuggcugu ugucauacuu cucaugguuc   60
cucug                                                            65

<210> SEQ ID NO 79
<211> LENGTH: 63
<212> TYPE: RNA
<213> ORGANISM: Artificial
<220> FEATURE:
<223> OTHER INFORMATION: nucleic acid molecule

<400> SEQUENCE: 79
ggaaccauga gaaguaugac aacagccaag cuuggcuguu gucauacuuc ucaugguucc   60
ucg                                                              63

<210> SEQ ID NO 80
<211> LENGTH: 62
<212> TYPE: RNA
<213> ORGANISM: Artificial
<220> FEATURE:
<223> OTHER INFORMATION: nucleic acid molecule
```

```
<400> SEQUENCE: 80
cagcuguaca uugacuuuag ccccacaccg gcuaaaguca auguacagcu gcuucuucgg     60
aa                                                                    62
```

SINGLE-STRANDED NUCLEIC ACID MOLECULE FOR CONTROLLING GENE EXPRESSION

A computer readable text file, entitled "SequenceListing.txt," created on or about Aug. 31, 2011 with a file size of about 15 kb contains the sequence listing for this application and is hereby incorporated by reference in its entirety.

TECHNICAL FIELD

The present invention relates to a single-stranded nucleic acid molecule that inhibits gene expression, a composition containing the single-stranded nucleic acid molecule, and the use of the single-stranded nucleic acid molecule.

BACKGROUND ART

As a technique for inhibiting gene expression. RNA interference (RNAi) is known, for example (Non-Patent Document 1). Inhibition of gene expression by RNA interference generally is carried out by administering a short double-stranded RNA molecule to a cell or the like, for example. The double-stranded RNA molecule generally is called siRNA (small interfering RNA). It has been reported that not only siRNA but also a circular RNA molecule that is rendered partially double-stranded by intermolecular annealing also can inhibit gene expression (Patent Document 1). However, the RNA molecules used in these techniques to induce the inhibition of the gene expression have the following problems.

First, in order to produce the siRNA, it is necessary to synthesize a sense strand and an antisense strand separately and to hybridize these strands at the end of the process. Thus, there is a problem of low manufacturing efficiency. Furthermore, when the siRNA is administered to a cell, it is necessary to administer the siRNA to the cell while repressing the dissociation to single-stranded RNAs, which requires a laborious task of setting the conditions for handling the siRNA. On the other hand, the circular RNA molecule has a problem in that its synthesis is difficult.

CITATION LIST

Patent Document(s)

Patent Document, 1: JP 2008-278784 A

Non-Patent Document(s)

Non-Patent Document 1: Fire, et al., Nature, vol. 391, pp. 806-811, 1998

BRIEF SUMMARY OF THE INVENTION

With the foregoing in mind, it is an object of the present invention to provide a novel nucleic acid molecule that can inhibit gene expression and also can be produced easily and efficiently.

In order to achieve the above object, the present invention provides a single-stranded nucleic acid molecule including an expression inhibitory sequence that inhibits expression of a target gene. The single-stranded nucleic acid molecule includes, in sequence from the 5' side to the 3' side: a 5' side region (Xc); an inner region (Z); and a 3' side region (Yc). The inner region (Z) is composed of an inner 5' side region (X) and an inner 3' side region (Y) that are linked to each other. The 5' side region (Xc) is complementary to the inner 5' side region (X). The 3' side region (Yc) is complementary to the inner 3' side region (Y). At least one of the inner region (Z), the 5' side region (Xc), and the 3' side region (Yc) includes the expression inhibitory sequence.

The present invention also provides a composition for inhibiting the expression of a target gene. The composition contains the single-stranded nucleic acid molecule according to the present invention.

The present invention also provides a pharmaceutical composition containing the single-stranded nucleic acid molecule according to the present invention.

The present invention also provides a method for inhibiting the expression of a target gene. In this method, the single-stranded nucleic acid molecule according to the present invention is used.

The present invention also provides a method for treating a disease, including the step of: administering the single-stranded nucleic acid molecule according to the present invention to a patient. The single-stranded nucleic acid molecule includes, as the expression inhibitory sequence, a sequence that inhibits expression of a gene causing the disease.

According to the single-stranded nucleic acid molecule of the present invention, it is possible to inhibit gene expression. Moreover, since the single-stranded nucleic acid molecule is not circular, it can be synthesized easily. Also, since it is a single strand, an annealing step required in the production of a double strand is not necessary, so that it can be produced efficiently.

It is the inventors of the present invention who first discovered that the gene expression can be inhibited according to the structure of the single-stranded nucleic acid molecule of the present invention. It is speculated that the gene inhibitory effect of the single-stranded nucleic acid molecule of the present invention is caused by a phenomenon similar to RNA interference. It is to be noted, however, that the inhibition of the gene expression in the present invention is not limited or restricted by RNA interference.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 12 show photographs each showing the result of Giemsa staining of cells in a BALF sample in the example of the present invention.

FIG. 13 shows photographs each showing the result of the HE staining of the lung tissue in the example of the present invention.

FIG. 21 shows ssRNA used in still another example of the present invention.

FIG. 23 shows ssRNA used in still another example of the present invention.

FIG. 25 shows ssRNA used in still another example of the present invention.

FIG. 26 is a graph showing the relative expression level of the GAPDH gene in the example of the present invention.

FIG. 27 shows ssRNA used in still another example of the present invention.

MODE FOR CARRYING OUT THE INVENTION

Figure 1A:
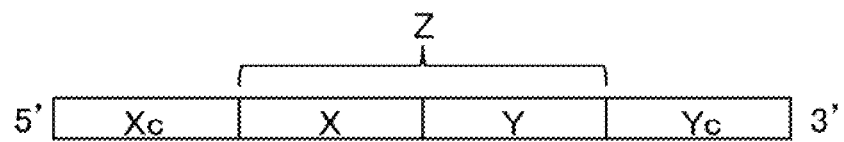
FIG. 1 shows schematic views illustrating an example of the single-stranded nucleic acid molecule of the present invention.

Terms used in the present specification each have a meaning generally used in the art, unless otherwise stated.

1. ssNc Molecule

The single-stranded nucleic acid molecule of the present invention is, as described above, a single-stranded nucleic acid molecule including an expression inhibitory sequence that inhibits expression of a target gene. The single-stranded nucleic acid molecule includes, in sequence from the 5' side to the 3' side: a 5' side region (Xc); an inner region (Z); and a 3' side region (Yc). The inner region (Z) is composed of an inner 5' side region (X) and an inner 3' side region (Y) that are linked to each other. The 5' side region (Xc) is complementary to the inner 5' side region (X). The 3' side region (Yc) is complementary to the inner 3' side region (Y). At least one of the inner region (Z), the 5' side region (Xc), and the 3' side region (Yc) includes the expression inhibitory sequence.

In the present invention, "inhibition of expression of a target gene" means disrupting the expression of the target gene, for example. The mechanism by which the inhibition is achieved is not particularly limited, and may be downregulation or silencing, for example. The inhibition of the expression of the target gene can be verified by: a decrease in the amount of a transcription product derived from the target gene; a decrease in the activity of the transcription product; a decrease in the amount of a translation product generated from the target gene; a decrease in the activity of the translation product; or the like, for example. The proteins may be mature proteins, precursor proteins before being subjected to processing or post-translational modification, or the like, for example.

The single-stranded nucleic acid molecule of the present invention hereinafter also may be referred to as the "ssNc molecule" of the present invention. The ssNc molecule of the present invention can be used to inhibit the expression of a target gene in vivo or in vitro, for example, so that it also can be referred to as an "ssNc molecule for inhibiting the expression of a target gene" or "inhibitor of the expression of a target gene". Furthermore, the ssNc molecule of the present invention can inhibit the expression of a target gene by, for example, RNA interference, so that it also can be referred to as an "ssNc molecule for RNA interference", "RNA interference-inducting molecule", "RNA interference agent", or "RNA interference-inducting agent". The ssNc molecule of the present invention also can inhibit a side effect such as interferon induction, for example.

In the ssNc molecule of the present invention, the 5' end and the 3' end are not linked to each other. Thus, the ssNc molecule of the present invention also can be referred to as a "linear single-stranded nucleic acid molecule". The ssNc molecule of the present invention is configured so that, for example, in the inner region (Z), the inner 5' side region (X) and the inner 3' side region (Y) are linked directly to each other.

In the ssNc molecule of the present invention, the 5' side region (Xc) is complementary to the inner 5' side region (X), and the 3' side region (Yc) is complementary to the inner 3' side region (Y). Thus, on the 5' side, a double strand can be formed by fold-back of the region (Xc) toward the region (X) and self-annealing of the regions (Xc) and (X). On the 3' side, a double strand can be formed by fold-back of the region (Yc) toward the region (Y) and self-annealing of the regions (Yc) and (Y). The ssNc molecule of the present invention can form a double strand intramolecularly as described above. Thus, the structure of the ssNc molecule is totally different from the structure of a double-stranded RNA obtained through annealing of two separate single-stranded RNAs, such as siRNA conventionally used in RNA interference, for example.

In the ssNc molecule of the present invention, the expression inhibitory sequence is a sequence that exhibits an activity of inhibiting the expression of a target gene when the ssNc molecule of the present invention is introduced into a cell in vivo or in vitro, for example. The expression inhibitory sequence is not particularly limited, and can be set as appropriate depending on the kind of a target gene whose expression is to be inhibited. As the expression inhibitory sequence, a sequence involved in RNA interference caused by siRNA can be used as appropriate, for example. Generally, RNA interference is a phenomenon in which a long double-stranded RNA (dsRNA) is cleaved in a cell by Dicer to produce a double-stranded RNA (siRNA: small interfering RNA) composed of about 19 to 21 base pairs and having a protruding 3' end, and one of the single-stranded RNAs composing the siRNA binds to a target mRNA to degrade the mRNA, whereby the translation of the mRNA is inhibited. As the sequence of the single-stranded RNA of the siRNA binding to the target mRNA, various kinds of sequences for various kinds of target genes have been reported, for example. In the present invention, for example, the sequence of the single-stranded RNA of the siRNA can be used as the expression inhibitory sequence.

It should be noted that the point of the present invention is not the sequence information of the expression inhibitory sequence for the target gene. Actually, the present invention relates to the structure of a nucleic acid molecule for allowing a target gene inhibitory activity brought about by the expression inhibitory sequence to function in a cell, for example. Therefore, in the present invention, not only the sequences of the single-stranded RNA of the siRNA known at the time of the filing of the present application but also sequences that would be identified in the future can be used as the expression inhibitory sequence, for example.

The expression inhibitory sequence preferably is at least 90% complementary, more preferably 95% complementary, still more preferably 98% complementary, and particularly preferably 100% complementary to a predetermined region of the target gene, for example. When the expression inhibitory sequence satisfies the above-described complementarity, an off-target effect can be reduced sufficiently, for example.

Specific examples of the expression inhibitory sequence are as follows: when the target gene is the GAPDH gene, a 19-mer sequence shown in SEQ ID NO: 1 can be used, for example; when the target gene is the TGF-β1 gene, a 21-mer sequence shown in SEQ ID NO: 16 can be used, for example; when the target gene is the LAMA1 gene, a 19-mer sequence shown in SEQ ID NO: 5 can be used, for example; and when the target gene is the LMNA gene, a 19-mer sequence shown in SEQ ID NO: 6 can be used, for example.

| | |
|---|---|
| 5'-GUUGUCAUACUUCUCAUGG-3' | (SEQ ID NO: 1) |
| 5'-AAAGUCAAUGUACAGCUGCUU-3' | (SEQ ID NO: 16) |
| 5'-AUUGUAACGAGACAAACAC-3' | (SEQ ID NO: 5) |
| 5'-UUGCGCUUUUUGGUGACGC-3' | (SEQ ID NO: 6) |

It is speculated that the inhibition of the expression of a target gene by the ssNc molecule of the present invention is achieved by RNA interference or a phenomenon similar to RNA interference (RNA interference-like phenomenon) caused by the structure of the ssNc molecule in which the expression inhibitory sequence is included in at least one of the inner region (Z), the 5' side region (Xc), and the 3' side region (Yc), for example. It should be noted, however, that the present invention is by no means limited by this mechanism. Unlike the so-called siRNA, the ssNc molecule of the present invention is not introduced to a cell or the like in the form of dsRNA composed of two single-stranded RNAs, and it is not always necessary to cleave out the expression inhibitory sequence in the cell, for example. Thus, it can be said that the ssNc molecule of the present invention exhibits an RNA interference-like function, for example.

In the ssNc molecule of the present invention, the expression inhibitory sequence is included in at least one of the inner region (Z), the 5' side region (Xc), and the 3' side region (Yc), as described above. The ssNc molecule of the present invention may include one expression inhibitory sequence, or two or more expression inhibitory sequences, for example.

In the latter case, the ssNc molecule of the present invention may include, for example: two or more identical expression inhibitory sequences for the same target gene; two of more different expression inhibitory sequences for the same target gene; or two or more different expression inhibitory sequences for different target genes. When the ssNc molecule of the present, invention includes two or more expression inhibitory sequences, the positions of the respective expression inhibitory sequences are not particularly limited, and they may be in one region or different regions selected from the inner region (Z), the 5' side region (Xc), and the 3' side region (Yc). When the ssNc molecule of the present invention includes two or more expression inhibitory sequences for different target genes, the ssNc molecule of the present invention can inhibit the expressions of two or more kinds of different target genes, for example.

As described above, the inner region (Z) is composed of the inner 5' side region (X) and the inner 3' side region (Y) that are linked to each other. The regions (X) and (Y) are linked directly to each other with no intervening sequence therebetween, for example. The inner region (Z) is described as being "composed of the inner 5' side region (X) and the inner 3' side region (Y) that are linked to each other" merely to indicate the sequence context between the 5' side region (Xc) and the 3' side region (Yc). This description does not intend to limit that, in the use of the ssNc molecule, the 5' side region (Xc) and the 3' side region (Xc) in the inner region (Z) are discrete independent regions, for example. That is, for example, when the expression inhibitory sequence is included in the inner region (Z), the expression inhibitory sequence may be arranged so as to extend across the regions (X) and (Y) in the inner region (Z).

In the ssNc molecule of the present invention, the 5' side region (Xc) is complementary to the inner 5' side region (X). It is only necessary that the region (Xc) has a sequence complementary to the entire region or part of the region (X). Specifically, for example, it is preferable that the region (Xc)

includes or is composed of a sequence complementary to the entire region or a part of the region (X). The region (Xc) may be perfectly complementary to the entire region or part of the region (X), or one or a few bases in the region (Xc) may be noncomplementary to the same, for example. Preferably, the region (Xc) is perfectly complementary to the same. In the ssNc molecule of the present invention, the 3' side region (Yc) is complementary to the inner 3' side region (Y). It is only necessary that the region (Yc) has a sequence complementary to the entire region or part of the region (Y). Specifically, for example, it is preferable that the region (Yc) includes or is composed of a sequence complementary to the entire region or part of the region (Y). The region (Yc) may be perfectly complementary to the entire region or part of the region (Y), or one or a few bases in the region (Yc) may be noncomplementary to the same, for example. Preferably, the region (Yc) is perfectly complementary to the same. The expression "one or a few bases" means, for example, 1 to 3 bases, preferably 1 base or 2 bases.

In the ssNc molecule of the present invention, the 5' side region (Xc) and the inner 5' side region (X) may be linked to each other either directly or indirectly, for example. In the former case, the regions (Xc) and (X) may be linked directly by phosphodiester linkage, for example. In the latter case, the ssNc molecule may be configured so that it has a linker region (Lx) between the regions (Xc) and (X), and the regions (Xc) and (X) are linked via the linker region (Lx), for example.

In the ssNc molecule of the present invention, the 3' side region (Yc) and the inner 3' side region (Y) may be linked to each other either directly or indirectly, for example. In the former case, the regions (Yc) and (Y) may be linked directly by phosphodiester linkage, for example. In the latter case, the ssNc molecule may be configured so that it has a linker region (Ly) between the regions (Yc) and (Y), and the regions (Yc) and (Y) are linked via the linker region (Ly), for example.

The ssNc molecule of the present invention may have both the linker regions (Lx) and (Ly), or may have either one of them, for example. In the latter case, the ssNc molecule of the present invention may be configured so that, for example, it has the linker region (Lx) between the 5' side region (Xc) and the inner 5' side region (X) and does not have the linker region (Ly) between the 3' side region (Yc) and the inner 3' side region (Y), i.e., the regions (Yc) and (Y) are linked directly to each other. Also, in the latter case, the ssNc molecule of the present invention may be configured so that, for example, it has the linker region (Ly) between the 3' side region (Yc) and the inner 3' side region (Y) and does not have the linker region (Lx) between the 5' side region (Xc) and the inner 5' side region (X), i.e., the regions (Xc) and (X) are linked directly to each other.

Preferably, the linker regions (Lx) and (Ly) each have a structure such that self-annealing is not caused inside themselves.

Figure 1B:
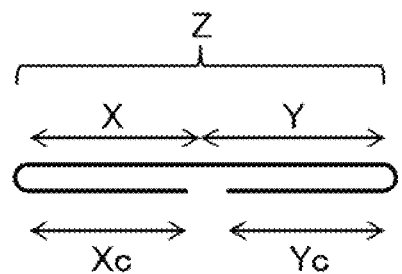

FIG. 1 shows schematic views illustrating an example of the ssNc molecule of the present invention, including no linker region. FIG. 1A is a schematic view showing the order of the respective regions from the 5' side to the 3' side in the ssNc molecule. FIG. 1B is a schematic view showing the state where double strands are formed in the ssNc molecule. As shown in FIG. 1B, in the ssNc molecule, the 5' side region (Xc) folds back, whereby a double strand is formed by the 5' side region (Xc) and the inner 5' side region (X), and the 3' side region (Yc) folds back, whereby a double strand is formed by the 3' side region (Yc) and the inner 3' side region (Y). The schematic views shown in FIG. 1 merely illustrate the order in which the respective regions are linked to each other and the positional relationship of the respective regions forming the double strands, and they do not limit the length and the like of each region, for example.

Figure 2A:
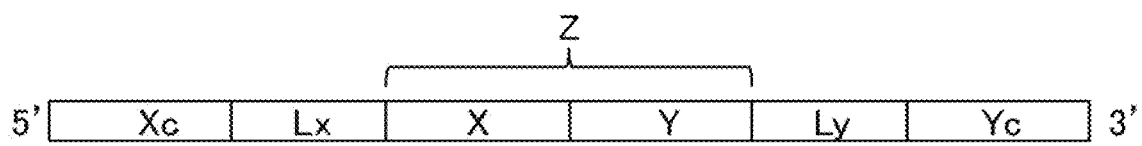
FIG. 2 shows schematic views illustrating another example of the single-stranded nucleic acid molecule of the present invention.
Figure 2B:
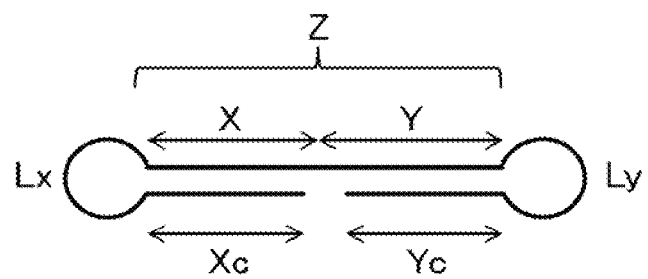
Figure 3A:
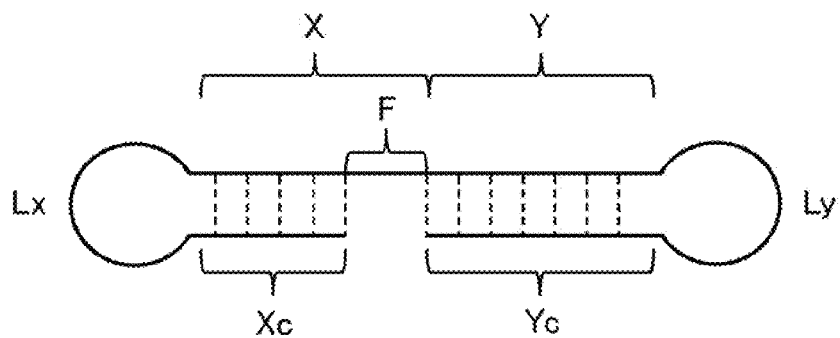
FIG. 3 shows schematic views illustrating other examples of the single-stranded nucleic acid molecule of the present invention.
Figure 3B:
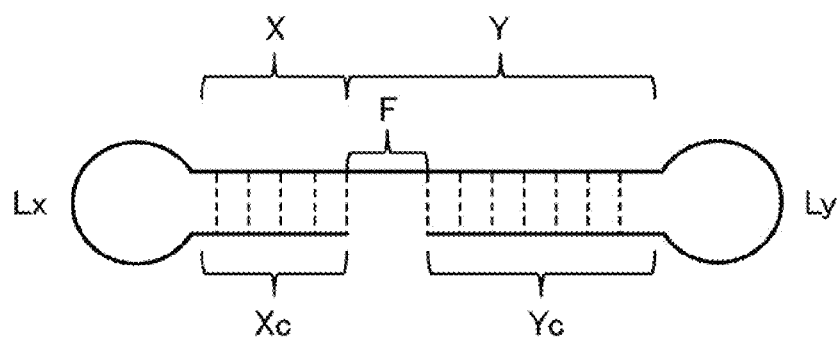
Figure 3C:
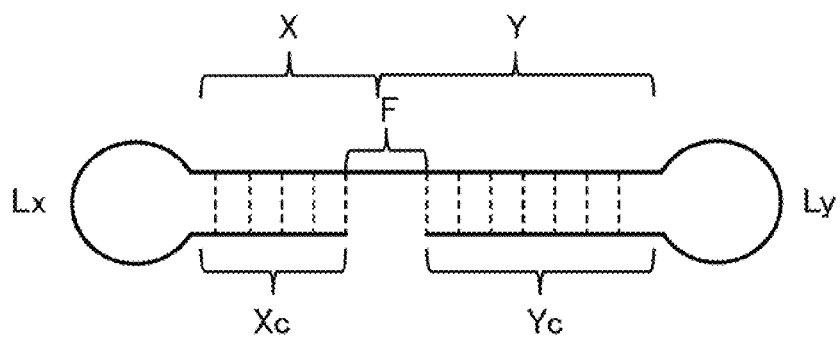
Figure 3D:
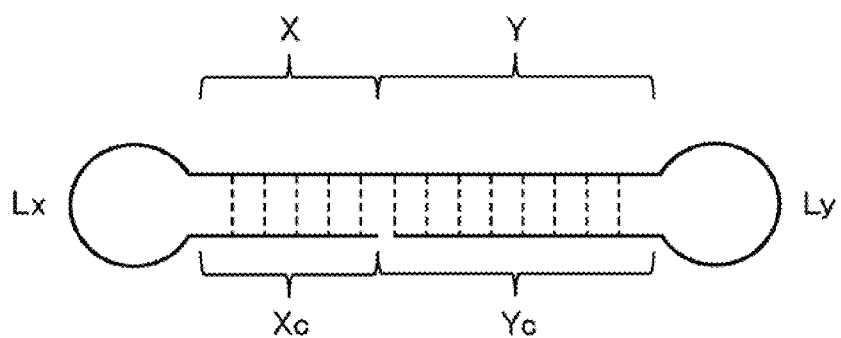

FIG. 2 shows schematic views illustrating an example of the ssNc molecule of the present invention, including the linker regions. FIG. 2A is a schematic view showing the order of the respective regions from the 5' side to the 3' side in the ssNc molecule, as an illustrative example. FIG. 2B is a schematic view showing the state where double strands are formed in the ssNc molecule. As shown in FIG. 2B, in the ssNc molecule, double strands are formed between the 5' side region (Xc) and the inner 5' side region (X) and between the inner 3' side region (Y) and the 3' side region (Yc), respectively, and the Lx region and the Ly region each is a loop structure. The schematic views shown in FIG. 2 merely illustrates the order in which the respective regions are linked and the positional relationship of the respective regions forming the double strands, and they do not limit the length and the like of each region, for example.

In the ssNc molecule of the present invention, the number of bases in each of the 5' side region (Xc), the inner 5' side region (X), the inner 3' side region (Y), and the 3' side region (Yc) is not particularly limited, and may be as follows, for example. In the present invention, "the number of bases" means the "length", for example, and it also can be referred to as the "base length".

As described above, the 5' side region (Xc) may be complementary to the entire region of the inner 5' side region (X), for example. In this case, it is preferable that, for example, the region (Xc) has the same base length as the region (X), and is composed of a base sequence complementary to the entire region extending from the 5' end to the 3' end of the region (X). It is more preferable that the region (Xc) has the same base length as the region (X), and all the bases in the region (Xc) are complementary to all the bases in the region (X), i.e., the region (Xc) is perfectly complementary to the region (X), for example. It is to be noted, however, that the configuration of the region (Xc) is not limited thereto, and one or a few bases in the region (Xc) may be noncomplementary to the corresponding bases in the region (X), for example, as described above.

Furthermore, as described above, the 5' side region (Xc) may be complementary to part of the inner 5' side region (X), for example. In this case, it is preferable that, for example, the region (Xc) has the same base length as the part of the region (X), i.e., the region (Xc) is composed of a base sequence whose base length is shorter than the base length of the region (X) by one or more bases. It is more preferable that the region (Xc) has the same base length as the part of the region (X) and all the bases in the region (Xc) are complementary to all the bases in the part of the region (X), i.e., the region (Xc) is perfectly complementary to the part of the region (X), for example. The part of the region (X) preferably is a region (segment) having a base sequence composed of successive bases starting from the base at the 5' end (the 1st base) in the region (X), for example.

As described above, the 3' side region (Yc) may be complementary to the entire region of the inner 3' side region (Y), for example. In this case, it is preferable that, for example, the region (Yc) has the same base length as the region (Y), and is composed of a base sequence complementary to the entire region extending from the 5' end to the 3' end of the region (Y). It is more preferable that the region (Yc) has the same base length as the region (Y), and all the bases in the region (Yc) are complementary to all the bases in the region (Y), i.e., the region (Yc) is perfectly complementary to the region (Y), for example. It is to be noted, however, that the configuration of the region (Yc) is not limited thereto, and one or a few bases in the region (Yc) may be noncomplementary to the corresponding bases in the region (Y), for example, as described above.

Furthermore, as described above, the 3' side region (Yc) may be complementary to part of the inner 3' side region (Y), for example. In this case, it is preferable that, for example, the region (Yc) has the same base length as the part of the region (Y), i.e., the region (Yc) is composed of a base sequence whose base length is shorter than the base length of the region (Y) by one or more bases. It is more preferable that the region (Yc) has the same base length as the part of the region (Y) and all the bases in the region (Yc) are complementary to all the bases in the part of the region (Y), i.e., the region (Yc) is perfectly complementary to the part of the region (Y), for example. The part of the region (Y) preferably is a region (segment) having a base sequence composed of successive bases starting from the base at the 3' end (the 1st base) in the region (Y), for example.

In the ssNc molecule of the present invention, the relationship of the number of bases (Z) in the inner region (Z) with the number of bases (X) in the inner 5' side region (X) and the number of bases (Y) in the inner 3' side region (Y), and the relationship of the number of bases (Z) in the inner region (Z) with the number of bases (X) in the inner 5' side region (X) and the number of bases (Xc) in the 5' side region (Xc) satisfy the conditions of Expressions (1) and (2), for example.

$$Z = X + Y \tag{1}$$

$$Z \geq Xc + Yc \tag{2}$$

In the ssNc molecule of the present invention, the length relationship between the number of bases (X) in the inner 5' side region (X) and the number of bases (Y) in the inner 3' side region (Y) is not particularly limited, and may satisfy any of the conditions of the following expressions, for example.

$$X = Y \tag{19}$$

$$X < Y \tag{20}$$

$$X > Y \tag{21}$$

In the ssNc molecule of the present invention, the relationship between the number of bases (X) in the inner 5' side region (X) and the number of bases (Xc) in the 5' side region (Xc), and the relationship between the number of bases (Y) in the inner 3' side region (Y) and the number of bases (Yc) in the 3' side region (Yc) satisfy any of the following conditions (a) to (d), for example.

(a) Conditions of Expressions (3) and (4) are satisfied.

$$X > Xc \tag{3}$$

$$Y = Yc \tag{4}$$

(b) Conditions of Expressions (5) and (6) are satisfied.

$$X = Xc \tag{5}$$

$$Y > Yc \tag{6}$$

(c) Conditions of Expressions (7) and (8) are satisfied.

$$X > Xc \tag{7}$$

$$Y > Yc \tag{8}$$

(d) Conditions of Expressions (9) and (10) are satisfied.

$$X = Xc \tag{9}$$

$$Y = Yc \tag{10}$$

In the above-described conditions (a) to (d), the difference between the number of bases (X) in the inner 5' side region (X) and the number of bases (Xc) in the 5' side region (Xc), and the difference between the number of bases (Y) in the inner 3' side region (Y) and the number of bases (Yc) in the 3' side region (Yc) preferably satisfy the following conditions (a) to (d), for example.

(a) Conditions of Expressions (11) and (12) are satisfied.

$$X-Xc=1 \text{ to } 10, \text{ preferably } 1, 2, 3 \text{ or } 4, \text{ and more preferably } 1, 2 \text{ or } 3 \tag{11}$$

$$Y-Yc=0 \tag{12}$$

(b) Conditions of Expressions (13) and (14) are satisfied.

$$X-Xc=0 \tag{13}$$

$$Y-Yc=1 \text{ to } 10, \text{ preferably } 1, 2, 3 \text{ or } 4, \text{ and more preferably } 1, 2 \text{ or } 3 \tag{14}$$

(c) Conditions of Expressions (15) and (16) are satisfied.

$$X-Xc=1 \text{ to } 10, \text{ preferably } 1, 2 \text{ or } 3, \text{ and more preferably } 1 \text{ or } 2 \tag{15}$$

$$Y-Yc=1 \text{ to } 10, \text{ preferably } 1, 2 \text{ or } 3, \text{ and more preferably } 1 \text{ or } 2 \tag{16}$$

(d) Conditions of Expressions (17) and (18) are satisfied.

$$X-Xc=0 \tag{17}$$

$$Y-Yc=0 \tag{18}$$

Regarding the ssNc molecules satisfying the conditions (a) to (d), examples of their structures are shown respectively in the schematic views of FIG. 3. FIG. 3 shows the ssNc molecules including the linker regions (Lx) and (Ly). FIG. 3A shows an example of the ssNc molecule satisfying the condition (a); FIG. 3B shows an example of the ssNc molecule satisfying the condition (b); FIG. 3C shows an example of the ssNc molecule satisfying the condition (c); and FIG. 3D shows an example of the ssNc molecule satisfying the condition (d). In FIG. 3, dotted lines indicate a state where double strands are formed by self-annealing. The ssNc molecules shown in FIG. 3 are all directed to examples where the relationship between the number of bases (X) in the inner 5' side region (X) and the number of bases (Y) in the inner 3' side region (Y) satisfy "X<Y" of Expression (20). It is to be noted, however, that the relationship is not limited thereto, and "X=Y" of Expression (19) or "X>Y" of Expression (21) may be satisfied. The schematic views shown in FIG. 3 merely illustrate the relationship between the inner 5' side region (X) and the 5' side region (Xc) and the relationship between the inner 3' side region (Y) and the 3' side region (Yc), and they do not limit the length, the shape, and the like of each region, and also the presence or absence of the linker regions (Lx) and (Ly), for example.

Each of the ssNc molecules satisfying the conditions (a) to (c) is configured so that, for example, when the double strands are formed by the 5' side region (Xc) and the inner 5' side region (X) and by the 3' side region (Yc) and the inner 3' side region (Y), respectively, the inner region (Z) includes at least one base that cannot be aligned with either of the 5' side region (Xc) and the 3' side region (Yc). In the inner region (Z), the base that cannot be aligned (a base that does not form the double strand) hereinafter also is referred to as an "unpaired base". In FIG. 3, a region composed of the unpaired base(s) is shown as "F". The number of bases in the region (F) is not particularly limited. The number of bases (F) in the region (F) is as follows, for example: "Xc−X" in the case of the ssNc molecule satisfying the condition (a); "Y−Yc" in the case of the ssNc molecule satisfying the condition (b); and the total of "Xc–X" and "Y–Yc" in the case of the ssNc molecule satisfying the condition (c).

On the other hand, the ssNc molecule satisfying the condition (d) is configured so that, for example, the entire region of the inner region (2) is aligned with the 5' side region (Xc) and the 3' side region (Yc), in other words, the entire region of the inner region (Z) forms a double strand. In the ssNc molecule satisfying the condition (d), the 5' end of the 5' side region (Xc) and the 3' end of the 3' side region (Yc) are not linked to each other.

Examples of the lengths of the respective regions in the ssNc molecule of the present invention are given below. It is to be noted, however, that the present invention is by no means limited thereto. In the present invention, for example, the numerical range regarding the number of bases discloses all the positive integers falling within that range. For example, the description "1 to 4 bases" disclosed all of "1, 2, 3, and 4 bases" (the same applies hereinafter).

The total number of the bases in the 5' side region (Xc), the bases in the 3' side region (Yc), and the unpaired bases (F) in the inner region (2) is equal to the number of the bases in the inner region (Z), for example. Thus, the length of the 5' side region (Xc) and the length of the 3' side region (Yc) can be determined as appropriate depending on the length of the inner region (Z), the number of the unpaired bases (F), and the positions of the unpaired bases, for example.

The number of the bases in the inner region (Z) is 19 or more, for example. The lower limit of the number of the bases is, for example, 19, preferably 20, and more preferably 21. The upper limit of the number of the bases is, for example, 50, preferably 40, and more preferably 30. A specific example of the number of the bases in the inner region (Z) is 19, 20, 21, 22, 23, 24, 25, 26, 27, 28, 29, or 30.

When the inner region (Z) includes the expression inhibitory sequence, the inner region (Z) may be a region composed of the expression inhibitory sequence only or a region including the expression inhibitory sequence, for example. The number of bases of the expression inhibitory sequence is, for example, 19 to 30, preferably 19, 20, or 21. When the inner region (Z) includes the expression inhibitory sequence, the expression inhibitory sequence further may have an additional sequence on its 5' sidle and/or 3' side. The number of bases in the additional sequence is, for example, 1 to 31, preferably 1 to 21, more preferably 1 to 11, and still more preferably 1 to 7.

The number of bases in the 5' side region (Xc) is, for example, 1 to 29, preferably 1 to 11, more preferably 1 to 7, still more preferably 1 to 4, and particularly preferably 1, 2, or 3. When the inner region (Z) or the 3' side region (Yc) includes the expression inhibitory sequence, the number of bases as described above is preferable, for example. A specific example is as follows: when the number of bases in the inner region (Z) is 19 to 30 (e.g. 19), the number of bases in the 5' side region (Xc) is, for example, 1 to 11, preferably 1 to 7, more preferably 1 to 4, and still more preferably 1, 2, or 3.

When the 5' side region (Xc) includes the expression inhibitory sequence, the 5' side region (Xc) may be a region composed of the expression inhibitory sequence only or a region including the expression inhibitory sequence, for example. The length of the expression inhibitory sequence is as described above, for example. When the 5' side region (Xc) includes the expression inhibitory sequence, the expression inhibitory sequence further may have an additional sequence on its 5' side and/or 3' side. The number of bases in the additional sequence is, for example, 1 to 11, preferably 1 to 7.

The number of bases in the 3' side region (Yc) is, for example, 1 to 29, preferably 1 to 11, more preferably 1 to 7, still more preferably 1 to 4, and particularly preferably 1, 2, or 3. When the inner region (Z) or the 5' side region (Xc) includes the expression inhibitory sequence, the number of bases as described above is preferable, for example. A specific example is as follows: when the number of bases in the inner region (Z) is 19 to 30 (e.g., 19), the number of bases in the 3' side region (Yc) is, for example, 1 to 11, preferably 1 to 7, more preferably 1 to 4, and still more preferably 1, 2, or 3.

When the 3' side region (Yc) includes the expression inhibitory sequence, the 3' side region (Yc) may be a region composed of the expression inhibitory sequence only or a region including the expression inhibitory sequence, for example. The length of the expression inhibitory sequence is as described above, for example. When the 3' side region (Yc) includes the expression inhibitory sequence, the expression inhibitory sequence further may have an additional sequence on its 5' side and/or 3' side. The number of bases in the additional sequence is, for example, 1 to 11, preferably 1 to 7.

As described above, the relationship among the number of bases in the inner region (Z), the number of bases in the 5' side region (Xc), and the number of bases in the 3' side region (Yc) can be expressed by Expression (2): "$Z \geq Xc+Yc$", for example. Specifically, the number of bases represented by "Xc+Yc" is equal to the number of bases in the inner region (Z), or lower than the number of bases in the inner region (Z), for example. In the latter case, "Z−(Xc+Yc)" is, for example, 1 to 10, preferably 1 to 4, and more preferably 1, 2, or 3. The "Z (Xc+Yc)" corresponds to the number of bases (F) in the unpaired base region (F) in the inner region (Z), for example.

In the ssNc molecule of the present invention, the lengths of the linker regions (Lx) and (Ly) are not particularly limited. The length of the linker region (Lx) preferably is such that, for example, the inner 5' side region (X) and the 5' side region (Xc) can form a double strand. The length of the linker region (Ly) preferably is such that, for example, the inner 3' side region (Y) and the 3' side region (Yc) can form a double strand. When the components (building blocks) of the linker regions (Lx) and (Ly) include bases, the number of bases in the linker region (Lx) may be equal to or different from the number of bases in the linker region (Ly). Also, their base sequences may be the same or different. The lower limit of the number of bases in each of the linker regions (Lx) and (Ly) is, for example, 1, preferably 2, and more preferably 3, and the upper limit of the same is, for example, 100, preferably 80, and more preferably 50. The number of bases in each of the linker regions specifically is 1 to 50, 1 to 30, 1 to 20, 1 to 10, 1 to 7, or 1 to 4, for example, but it is not limited to these examples.

The full length of the ssNc molecule of the present invention is not particularly limited. In the ssNc molecule of the present invention, the lower limit of the total number of bases (the number of bases in the full length ssNc molecule), is, for example, 38, preferably 42, more preferably 50, still more preferably 51, and particularly preferably 52, and the upper limit of the same is, for example, 300, preferably 200, more preferably 150, still more preferably 100, and particularly preferably 80. In the ssNc molecule of the present invention, the lower limit of the total number of bases excluding those in the linker regions (Lx) and (Ly) is, for example, 38, preferably 42, more preferably 50, still more preferably 51, and particularly preferably 52, and the upper limit of the same is, for example, 300, preferably 200, more preferably 150, still more preferably 100, and particularly preferably 80.

The components of the ssNc molecule of the present invention are not particularly limited, and examples thereof include nucleotide residues. Examples of the nucleotide residues include a ribonucleotide residue and a deoxyribonucleotide residue. The nucleotide residue may be the one that is not modified (unmodified nucleotide residue) or the one that has been modified (modified nucleotide residue), for example. By configuring the ssNc molecule of the present invention so as to include a modified nucleotide residue, for example, the resistance of the ssNc molecule to nucleases can be improved, thereby allowing the stability of the ssNc molecule to be improved. Furthermore, the ssNc molecule of the present invention further may include, for example, a non-nucleotide residue in addition to the nucleotide residue. The details of the nucleotide residue and the non-nucleotide residue will be described below.

In the ssNc molecule of the present invention, the nucleotide residue is preferable as the component of each of the inner region (Z), the 5' side region (Xc), and the 3' side region (YC). Each of the regions is composed of any of the following residues (1) to (3), for example.
(1) an unmodified nucleotide residue(s)
(2) a modified nucleotide residue(s)
(3) an unmodified nucleotide residue(s) and a modified nucleotide residue(s)

In the ssNc molecule of the present invention, the components of the linker regions (Lx) and (Ly) are not particularly limited, and examples thereof include the above-described nucleotide residues and non-nucleotide residues. Each of the linker regions may be composed of the nucleotide residue(s) only, the non-nucleotide residue(s) only, or both the nucleotide residue(s) and the non-nucleotide residue(s). Each of the linker regions is composed of any of the following residues (1) to (7), for example.
(1) an unmodified nucleotide residue(s)
(2) a modified nucleotide residue(s)
(3) an unmodified nucleotide residue(s) and a modified nucleotide residue(s)
(4) a non-nucleotide residue(s)
(5) a non-nucleotide residue(s) and an unmodified nucleotide residue(s)
(6) a non-nucleotide residue(s) and a modified nucleotide residue(s)
(7) a non-nucleotide residue(s), an unmodified nucleotide residue(s), and a modified nucleotide residue(s)

When the ssNc molecule of the present invention has both the linker regions (Lx) and (4), the components of both the regions may be the same or different, for example. Specific examples are such that: the components of both the regions are the nucleotide residues; the components of both the regions are the non-nucleotide residues; and the component of one of the regions is the nucleotide residue while the component of the other linker region is the non-nucleotide residue.

Examples of the ssNc molecule of the present invention include: molecules composed of the nucleotide residues only; and molecules including the non-nucleotide residue(s) in addition to the nucleotide residues. In the ssNc molecule of the present invention, the nucleotide residues may be the unmodified nucleotide residues only; the modified nucleotide residues only; or both the unmodified nucleotide residue(s) and the modified nucleotide residue(s), as described above, for example. When the ssNc molecule includes both the unmodified nucleotide residue(s) and the modified nucleotide residue(s), the number of the modified nucleotide residue(s) is not particularly limited, and is, for example, "one or more", specifically, for example, 1 to 5, preferably 1 to 4, more preferably 1 to 3, and most preferably 1 or 2. When the ssNc molecule of the present invention include the non-nucleotide residue(s), the number of the non-nucleotide residue(s) is not particularly limited, and is, for example, "one or more", specifically, for example, 1 to 8, 1 to 6, 1 to 4, or 1, 2, or 3.

In the ssNc molecule of the present invention, the nucleotide residue preferably is a ribonucleotide residue, for example. In this case, the ssNc molecule of the present invention also is referred to as an "RNA molecule" or "ssRNA molecule", for example. Examples of the ssRNA molecule include: molecules composed of the ribonucleotide residues only; and a molecule including the non-nucleotide residue(s) in addition to the ribonucleotide residues. As described above, as the ribonucleotide residues, the ssRNA molecule may include: the unmodified ribonucleotide residues only; modified ribonucleotide residues only; or both the unmodified ribonucleotide residue(s) and the modified ribonucleotide residue(s), for example.

When the ssRNA molecule includes the modified ribonucleotide residue(s) in addition to the unmodified ribonucleotide residues, for example, the number of the modified ribonucleotide residue(s) is not particularly limited, and is, for example, "one or more", specifically, for example, 1 to 5, preferably 1 to 4, more preferably 1 to 3, and most preferably 1 or 2. The modified ribonucleotide residue as contrasted to the unmodified ribonucleotide residue may be the deoxyribonucleotide residue obtained by substituting a ribose residue with a deoxyribose residue, for example. When the ssRNA molecule includes the deoxyribonucleotide residue(s) in addition to the unmodified ribonucleotide residue(s), for example, the number of the deoxyribonucleotide residue(s) is not particularly limited, and is, for example, "one or more", specifically, for example, 1 to 5, preferably 1 to 4, more preferably 1 to 3, and most preferably 1 or 2.

The ssNc molecule of the present invention may include a labeling substance (marker), and may be labeled with the labeling substance, for example. The labeling substance is not particularly limited, and may be a fluorescent substance, a dye, an isotope, or the like, for example. Examples of the fluorescent substance include: fluorophores such as pyrene, TAMRA, fluorescein, a Cy3 dye, and a Cy5 dye. Examples of the dye include Alexa dyes such as Alexa 488. Examples of the isotope include stable isotopes and radioisotopes. Among them, stable isotopes are preferable. Stable isotopes have a low risk of radiation exposure, and they require no dedicated facilities, for example. Thus, stable isotopes are excellent in handleability and can contribute to cost reduction. Moreover, a stable isotope does not change the physical properties of a compound labeled therewith, for example, and thus has an excellent property as a tracer. The stable isotope is not particularly limited, and examples thereof include $^2H$, $^{13}C$, $^{13}N$, $^{17}O$, $^{18}O$, $^{33}S$, $^{34}S$, and, $^{36}S$.

As previously described, the ssNc molecule of the present invention can inhibit the expression of a target gene. Thus, the ssNc molecule of the present invention can be used as a therapeutic agent for treating a disease caused by a gene, for example. When the ssNc molecule includes, as the expression inhibitory sequence, a sequence that inhibits expression of a gene causing the disease, for example, it is possible to treat the disease by inhibiting the expression of the target gene. In the present invention, the term "treatment" encompasses: prevention of diseases; improvement of diseases; and improvement in prognosis, for example, and it can mean any of them.

The method of using the ssNc molecule of the present invention is not particularly limited. For example, the ssNc molecule may be administered to a subject having the target gene.

Examples of the subject to which the ssNc molecule of the present invention is administered include cells, tissues, and organs. Examples of the subject also include humans and nonhuman animals such as nonhuman mammals, i.e., mammals excluding humans. The administration may be performed in vivo or in vitro, for example. The cells are not particularly limited, and examples thereof include: various cultured cells such as HeLa cells, 293 cells, NIH3T3 cells, and COS cells; stem cells such as ES cells and hematopoietic stem cells; and cells isolated from living organisms, such as primary cultured cells.

In the present invention, the target gene whose expression is to be inhibited is not particularly limited, and any desired gene can be set to the target gene. After setting the target gene, the expression inhibitory sequence may be designed as appropriate depending on the kind of the target gene, as described above.

Specific examples of the ssNc molecule of the present invention will be given below. It is to be noted, however, that the present invention is by no means limited thereto. Examples of the base sequence of the ssNc molecule include: base sequences of SEQ ID NOs: 2, 7, 8, 13, 14, 29 to 35, 37, 43, 44, 47, 48, and 51 to 80; and base sequences obtained by for example, deletion, substitution, and/or addition of one or more bases in these base sequences. When the target gene is the GAPDH gene, examples of the base sequence of the ssNc molecule include the base sequences of SEQ ID NOs: 2, 7, 8, 13, 37 and 51 to 80. When the target gene is the TGF-β1, examples of the base sequence of the ssNc molecule include the base sequences of SEQ ID NOs: 14 and 29 to 35. When the target gene is the LAMA1 gene, examples of the base sequence of the ssNc molecule include the base sequences of SEQ ID NOs: 43 and 44. When the target gene is the LMNA gene, examples of the base sequence of the ssNc molecule include the base sequences of SEQ ID NOs: 47 and 48.

As to the use of the ssNc molecule of the present invention, the following description regarding the composition, the inhibitory method, the treatment method, and the like according to the present invention to be describe below can be referred to.

Since the ssNc molecule of the present invention can inhibit the expression of a target gene as described above, it is useful as a pharmaceutical, a diagnostic agent, an agricultural chemical, and a tool for conducting research on agricultural chemicals, medical science, life science, and the like, for example.

2. Nucleotide Residue

The nucleotide residue includes, as its components, a sugar, a base, and a phosphate. The nucleotide residue may be, for example, a ribonucleotide residue or a deoxyribonucleotide residue, as described above. The ribonucleotide residue has, for example: a ribose residue as the sugar; and adenine (A), guanine (O), cytosine (C), or uracil (U) as the base. The deoxyribose residue has, for example: a deoxyribose residue as the sugar; and adenine (A), guanine (G), cytosine (C), or thymine (T) as the base.

The nucleotide residue may be, for example, an unmodified nucleotide residue or a modified nucleotide residue. The components of the unmodified nucleotide residue are the same or substantially the same as the components of a naturally-occurring nucleotide residue, for example. Preferably, the components are the same or substantially the same as the components of a nucleotide residue occurring naturally in a human body.

The modified nucleotide residue is a nucleotide residue obtained by modifying the unmodified nucleotide residue, for example. The modified nucleotide residue may be such that any of the components of the unmodified nucleotide residue is modified, for example. In the present invention, "modification" means, for example: substitution, addition, and/or deletion of any of the components; and substitution, addition, and/or deletion of an atom(s) and/or a functional group(s) in the component(s). It also can be referred to as "alteration". Examples of the modified nucleotide residue include naturally-occurring nucleotide residues and artificially-modified nucleotide residues. Regarding the naturally-derived modified nucleotide residues, Limbach et al. (1994, Summary: the modified nucleosides of RNA, Nucleic Acids Res. 22: pp. 2183 to 2196) can be referred to, for example. The modified nucleotide residue may be a residue of an alternative of the nucleotide, for example.

Examples of the modification of the nucleotide residue include modification of a ribose-phosphate backbone (hereinafter referred to as a "ribophosphate backbone").

In the ribophosphate backbone, a ribose residue may be modified, for example. In the ribose residue, for example, the 2'-position carbon can be modified. Specifically, a hydroxyl group hound to the 2'-position carbon can be substituted with hydrogen or a halogen such as fluoro, for example. By substituting the hydroxyl group bound to the 2'-position carbon with hydrogen, it is possible to substitute the ribose residue with deoxyribose. The ribose residue can be substituted with its stereoisomer, for example, and may be substituted with an arabinose residue, for example.

The ribophosphate backbone may be substituted with a non-ribophosphate backbone having a non-ribose residue and/or a non-phosphate, for example. The non-ribophosphate backbone may be, for example, the ribophosphate backbone modified so as to be uncharged. Examples of an alternative obtained by substituting the ribophosphate backbone with the non-ribophosphate backbone in the nucleotide include morpholino, cyclobutyl, and pyrrolidine. Other examples of the alternative include artificial nucleic acid monomer residues. Specific examples thereof include PNA (Peptide Nucleic Acid), LNA (Locked Nucleic Acid), and ENA (2'-O,4'-C-Ethylenebridged Nucleic Acid). Among them, PNA is preferable.

In the ribophosphate backbone, a phosphate group can be modified, for example. In the ribophosphate backbone, a phosphate group in the closest proximity to the sugar residue is called an "α-phosphate group". The α-phosphate group is charged negatively, and the electric charges are distributed evenly over two oxygen atoms that are not linked to the sugar residue. Among the four oxygen atoms in the α-phosphate group, the two oxygen atoms not linked to the sugar residue in the phosphodiester linkage between the nucleotide residues hereinafter are referred to as "non-linking oxygens". On the other hand, two oxygen atoms that are linked to the sugar residue in the phosphodiester linkage between the nucleotide residues hereinafter are referred to as "linking oxygens". The α-phosphate group preferably is modified so as to be uncharged, or so as to render the charge distribution between the non-linking oxygens asymmetric, for example.

In the phosphate group, the non-linking oxygen(s) may be substituted, for example. The oxygen(s) can be substituted with any atom selected from S (sulfur). Se (selenium), B (boron), C (carbon). H (hydrogen). N (nitrogen), and OR (R is an alkyl group or an aryl group), for example, and substitution with S is preferable. It is preferable that both the non-linking oxygens are substituted, for example, and it is more preferable that both the non-linking oxygens are substituted with S. Examples of the thus-modified phosphate group include phosphorothioates, phosphorodithioates, phosphoroselenates, borano phosphates, borano phosphate esters, hydrogen phosphonates, phosphoroamidates, alkyl or aryl phosphonates, and phosphotriesters. In particular, phosphorodithioate in which both of the two non-linking oxygens are substituted with S is preferable.

In the phosphate group, the linking oxygen(s) may be substituted, for example. The oxygen(s) can be substituted with any atom selected from S (sulfur), C (carbon), and N (nitrogen), for example. Examples of the thus-modified phosphate group include: bridged phosphoroamidates resulting from the substitution with N; bridged phosphorothioates resulting from the substitution S; and bridged methylenephosphonates resulting from the substitution C. Preferably, substitution of the linking oxygen(s) is performed in at least one of the 5' end nucleotide residue and the 3' end nucleotide residue of the ssNc molecule of the present invention, for example. When the substitution is performed on the 5' side, substitution with C is preferable. When the substitution is performed on the 3' side, substitution with N is preferable.

The phosphate group may be substituted with the phosphate-free linker, for example. The linker may contain siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo, methyleneoxymethylimino, or the like. Preferably, the linker may contain a methylene carbonyl amino group and a methylenemethylimino group.

In the ssNc molecule of the present invention, for example, at least one of a nucleotide residue at the 3' end and a nucleotide residue at the 5' end may be modified. The nucleotide residue at either one of the 3' end and the 5' end may be modified, or the nucleotide residues at both the 3' end and the 5' end may be modified, for example. The modification may be as described above, for example, and it is preferable to modify a phosphate group(s) at the end(s). The entire phosphate group may be modified, or one or more atoms in the phosphate group may be modified, for example. In the former case, for example, the entire phosphate group may be substituted or deleted.

Modification of the nucleotide residue(s) at the end(s) may be addition of any other molecule, for example. Examples of the other molecule include functional molecules such as labeling substances as described above and protecting groups. Examples of the protecting groups include S (sulfur), Si (silicon), B (boron), and ester-containing groups. The functional molecules such as the labeling substances can be used in the detection and the like of the ssNc molecule of the present invention, for example.

The other molecule may be added to the phosphate group of the nucleotide residue, or may be added to the phosphate group or the sugar residue via a spacer, for example. The terminal atom of the spacer can be added to or substituted for either one of the linking oxygens of the phosphate group, or O, N, S, or C of the sugar residue, for example. The binding site in the sugar residue preferably is, for example, C at the 3'-position, C at the 5'-position, or any atom bound thereto. The spacer also can be added to or substituted for a terminal atom of the nucleotide alternative such as PNA, for example.

The spacer is not particularly limited, and examples thereof include $-(CH_2)_n-$, $-(CH_2)_nN-$, $-(CH_2)_nO-$, $-(CH_2)_n S-$, $O(CH_2CH_2O)_nCH_2CH_2OH$, abasic sugars, amide, carboxy, amine, oxyamine, oxyimine, thioether, disulfide, thiourea, sulfonamide, and morpholino, and also biotin reagents and fluorescein reagents. In the above formulae, n is a positive integer, and n=3 or 6 is preferable.

Other examples of the molecule to be added to the end include dyes, intercalating agents (e.g., acridines), crosslinking agents (e.g., psoralen, mitomycin C), porphyrins (TPPC4, texaphyrin, Sapphyrin), polycyclic aromatic hydrocarbons (e.g., phenazine, dihydrophenazine), artificial endonucleases EDTA), lipophilic carriers (e.g., cholesterol, cholic acid, adamantane acetic acid, 1-pyrene butyric acid, dihydrotestosterone, 1,3-Bis-O (hexadecyl)glycerol, a geranyloxyhexyl group, hexadecylglycerol, borneol, menthol, 1,3-propanediol, a heptadecyl group, palmitic acid, myristic acid, O3-(oleoyl)lithocholic acid, O3-(oleoyl)cholic acid, dimethoxytrityl, or phenoxazine), peptide complexes (e.g. Antennapedia peptide, Tat peptide), alkylating agents, phosphate, amino, mercapto, PEG (e.g., PEG-40K), MPEG, $(MPEG)_2$, polyamine, alkyl, substituted alkyl, radiolabeled markers, enzymes, haptens (e.g., biotin), transport/absorption facilitators (e.g., aspirin, vitamin E, folic acid), and synthetic ribonucleases (e.g. imidazole, bisimidazole, histamine, imidazole clusters, acridine-imidazole complexes, $Eu^{3+}$ complexes of tetraazamacrocycles).

In the ssNc molecule of the present invention, the 5' end may be modified with a phosphate group or a phosphate group analog, for example.

Examples of the phosphate group include:
5'-monophosphate $((HO)_2(O)P—O-5')$;
5'-diphosphate $((HO)_2(O)P—O—P(HO)(O)—O-5')$;
5'-triphosphate $(HO)_2(O)P—O—(HO)(O)P—O—P(HI)(O)—O-5')$;
5'-guanosine cap (7-methylated or non-methylated. 7m-G-O-5'-(HO)(O)P—O—(HO)(O)P—O—P(HO)(O)—O-5')$;
5'-adenosine cap (Appp);
any modified or unmodified nucleotide cap structure $(N—O-5'-(HO)(O)P—O—(HO)(O)P—O—P(HO)(O)—O-5')$;
5'-monothiophosphate (phosphorothioate: $(HO)_2(S)P—O-5')$;
5'-monodithiophosphate (phosphorodithioate: $(HO)(HS)(S)P—O-5')$;
5'-phosphorothiolate $((HO)_2(O)P—S-5')$;
sulfur substituted monophosphate, diphosphate, and triphosphates (e.g., 5'-α-thiotriphosphate, 5'-γ-thiotriphosphate, and the like);
5'-phosphoramidates $((HO)_2(O)P—NH-5', (HO)(NH_2)(O)P—O-5')$;
5'-alkylphosphonates (e.g., RP(OH)(O)—O-5', $(OH)_2(O)P$-5'-$CH_2$, where R is alkyl (e.g. methyl, ethyl, isopropyl, propyl, or the like)); and
5'-alkyletherphosphonates (e.g., RP(OH)(O)—O-5', where R is alkylether (e.g., methoxymethyl, ethoxymethyl, or the like)).

In the nucleotide residue, the base is not particularly limited. The base may be a natural base or a non-natural base, for example. The base may be a naturally-derived base or a synthetic base, for example. As the base, a common (universal) base, a modified analog thereof, and the like can be used, for example.

Examples of the base include: purine bases such as adenine and guanine; and pyrimidine bases such as cytosine, uracil, and thymine. Other examples of the base include inosine, thymine, xanthine, hypoxanthine, nubularine, isoguanisine, and tubercidine. Examples of the base also include: alkyl derivatives such as 2-aminoadenine, 6-methylated purine, and 2-propylated purin; 5-halouracil and 5-halocytosine; 5-propynyl uracil and 5-propynyl cytosine; 6-azo uracil, 6-azo cytosine, and 6-azo thymine; 5-uracil (pseudouracil), 4-thiouracil, 5-halouracil, 5-(2-aminopropyl)uracil, 5-amino allyl uracil; 8-halogenated, aminated, thiolated, thioalkylated, hydroxylated, and other 8-substituted purines; 5-trifluoromethylated and other 5-substituted pyrimidines; 7-methylguanine; 5-substituted pyrimidines; 6-azapyrimidines;

N-2, N-6, and O-6 substituted purines (including 2-aminopropyladenine); 5-propynyluracil and 5-propynylcytosine; dihydrouracil; 3-deaza-5-azacytosine; 2-aminopurine; 5-alkyluracil; 7-alkylguanine; 5-alkylcytosine; 7-deazaadenine; N6,N6-dimethyladenine; 2,6-diaminopurine; 5-amino-allyl-uracil; N3-methyluracil; substituted 1,2,4-triazoles; 2-pyridinone; 5-nitroindole; 3-nitropyrrole; 5-methoxyuracil; uracil-5-oxyacetic acid; 5-methoxycarbonylmethyluracil; 5-methyl-2-thiouracil; 5-methoxycarbonylmethyl-2-thiouracil; 5-methylaminomethyl-2-thiouracil; 3-(3-amino-3-carboxypropyl)uracil; 3-methylcytosine; 5-methylcytosine; N4-acetylcytosine; 2-thiocytosine; N6-methyladenine; N6-isopentyladenine; 2-methylthio-N-6-isopentenyladenine; N-methylguanine; and O-alkylated bases. Examples of the purities and pyrimidines include those disclosed in U.S. Pat. No. 3,687,808, "Concise Encyclopedia of Polymer Science and Engineering", pp. 858 to 859, edited by Kroschwitz J. I. John Wiley & Sons, 1990, and Englisch et al, Angewandte Chemie, International Edition, 1991, vol. 30, p. 613.

Other examples of the modified nucleotide residue include those having no base, i.e., those having an abasic ribophosphate backbone. Furthermore, as the modified nucleotide residue, those described in U.S. Provisional Application 60/465,665 (filing date: Apr. 23, 2003) and International Application No. PCT/US04/07070 (filing date: Mar. 8, 2004) can be used, for example, and these documents are incorporated herein by reference.

3. Non-Nucleotide Residue

The non-nucleotide residue is not particularly limited. The ssNc molecule of the present invention may include, as the non-nucleotide residue, a non-nucleotide structure containing a pyrrolidine skeleton or a piperidine skeleton, for example. Preferably, at least one of the linker regions (Lx) and (Ly) has the non-nucleotide residue, for example. For example, the non-nucleotide residue may be in the linker region (Lx), in the linker region (Ly), or in both the linker regions. The linker regions (Lx) and (Ly) may be the same or different, for example.

The pyrrolidine skeleton may be the backbone of a pyrrolidine derivative obtained through substitution of at least one carbon constituting the 5-membered ring of pyrrolidine, for example. In the case of substitution, it is preferable to substitute the carbon(s) other than C-2, for example. The carbon may be substituted with nitrogen, oxygen, or sulfur, for example. The pyrrolidine skeleton may contain, for example, a carbon-carbon double bond or a carbon-nitrogen double bond in, for example, the 5-membered ring of pyrrolidine. In the pyrrolidine skeleton, carbons and nitrogen constituting the 5-membered ring of pyrrolidine each may have a hydrogen group bound thereto, or a substituent to be described below bound thereto, for example. The linker region (Lx) may be linked to the regions (X) and (Xc) via, for example, any group in the pyrrolidine skeleton, preferably any one carbon atom or nitrogen in the 5-membered ring, and more preferably the 2-position carbon (C-2) or nitrogen in the 5-membered ring. Examples of the pyrrolidine skeleton include proline backbones and prolinol backbones. The proline backbones, the prolinol backbones, and the like are excellent in safety because they are substances present in living organisms and reductants thereof, for example.

The piperidine skeleton may be the backbone of a piperidine derivative obtained through substitution of at least one carbon constituting the 6-membered ring of piperidine, for example. In the case of substitution, it is preferable to substitute the carbon(s) other than C-2, for example. The carbon may be substituted with nitrogen, oxygen, or sulfur, for example. The piperidine skeleton may contain, for example, a carbon-carbon double bond or a carbon-nitrogen double bond in, for example, the 6-membered ring of piperidine. In the piperidine skeleton, carbons and nitrogen constituting the 6-membered ring of piperidine each may have a hydrogen group bound thereto, or a substituent to be described below bound thereto, for example. The linker region (Lx) may be linked to the regions (X) and (Xc) via, for example, any group in the piperidine skeleton, preferably any one carbon atom or nitrogen in the 6-membered ring, and more preferably the 2-position carbon (C-2) or nitrogen in the 6-membered ring. The same applies to the linker region (Ly).

Each of the linker regions may be composed of the non-nucleotide residue(s) having the non-nucleotide structure only, or may contain the non-nucleotide residue(s) having the non-nucleotide structure and the nucleotide residue(s), for example.

The linker region is represented by the following formula (I), for example.

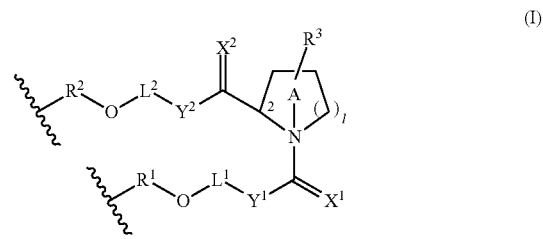

In the formula (I), $X^1$ and $X^2$ are each independently $H_2$, O, S, or NH;

$Y^1$ and $Y^2$ are each independently a single bond, $CH_2$, NH, O, or S;

$R^3$ is a hydrogen atom or substituent that is bound to C-3, C-4, C-5, or C-6 on a ring A;

the substituent is OH, $OR^4$, $NH_2$, $NHR^4$, $NR^4R^5$, SH, $SR^4$, or an oxo group (=O);

when $R^3$ is the substituent, there may be one substituent $R^3$, two or more substituents $R^3$, or no substituent $R^3$, and when there are a plurality of substituents $R^3$, they may be the same or different;

$R^1$ and $R^5$ are each a substituent or a protecting group, and they may be the same or different;

$L^1$ is an alkylene chain composed of n atoms, and a hydrogen atom(s) on an alkylene carbon atom(s) may or may not be substituted with OH, $OR^a$, $NH_2$, $NHR^a$, $NR^aR^b$, SH, or $SR^a$, or, $L^1$ is a polyether chain obtained by substituting at least one carbon atom on the alkylene chain with an oxygen atom, provided that: when $Y^1$ is NH, O, or S, an atom bound to $Y^1$ in $L^1$ is carbon, an atom bound to $OR^1$ in $L^1$ is carbon, and oxygen atoms are not adjacent to each other;

$L^2$ is an alkylene chain composed of m atoms, and a hydrogen atom(s) on an alkylene carbon atom(s) may or may not be substituted with OH, $O^c$, $NH_2$, $NHR^c$, $NR^cR^d$, SH, or $SH^c$, or $L^2$ is a polyether chain obtained by substituting at least one carbon atom on the alkylene chain with an oxygen atom, provided that: when $Y^2$ is NH, O, or S, an atom bound to $Y^2$ in $L^2$ is carbon, an atom bound to $OR^2$ in $L^2$ is carbon, and oxygen atoms are not adjacent to each other;

$R^a$, $R^b$, $R^c$, and $R^d$ are each independently a substituent or a protecting group;

l is 1 or 2;

m is an integer in the range from 0 to 30;

n is an integer in the range from 0 to 30;

on the ring A, one carbon atom other than C-2 may be substituted with nitrogen, oxygen, or sulfur, and the ring A may contain a carbon-carbon double bond or a carbon-nitrogen double bond. When the linker region (Lx) is represented by the formula (I), the regions (Xc) and (X) are each linked to the linker region (Lx) via —$OR^1$— or —$OR^2$—. Furthermore, when the linker region (Ly) is represented by the formula (I), the regions (Yc) and (Y) are each linked to the linker region (Ly) via —$OR^1$— or —$OR^2$—. It is to be noted that $R^1$ and $R^2$ may or may not be present, and when they are present. $R^1$ and $R^2$ are each independently a nucleotide residue or the structure of the formula (I).

In the formula (I), $X^1$ and $X^2$ are each independently $H_2$, O, S, or NH, for example. In the formula (I), "$X^1$ is $H_2$" means that $X^1$ forms $CH_2$ (a methylene group) together with a carbon atom to which $X^1$ binds. The same applies to $X^2$.

In the formula (I), l in the ring A is 1 or 2. When l=1, the ring A is a 5-membered ring, which is, for example, the pyrrolidine skeleton. The pyrrolidine skeleton is, for example, a proline backbone, a prolinol backbone, or the like, and specific examples include divalent structures of the proline backbone and the prolinol backbone. When l=2, the ring A is a 6-membered ring, which is, for example, the piperidine skeleton. On the ring A, one carbon atom other than C-2 may be substituted with nitrogen, oxygen, or sulfur. Furthermore, the ring A may contain a carbon-carbon double bond or a carbon-nitrogen double bond. The ring A may be in either L-form or D-form, for example.

In the formula (I), $Y^1$ and $Y^2$ are each independently a single bond, $CH_2$, NH, O, or S.

In the formula (I), $R^3$ is a hydrogen atom or substituent that is bound to C-3. C-4, C-5, or C-6 on the ring A. The substituent is OH, $OR^4$, $NH_2$, $NHR^4$, $NR^4R^5$, SH, $SR^4$, or an oxo group (=O). When $R^3$ is the substituent, there may be one substituent $R^3$ two or more substituents $R^3$, or no substituent $R^3$, and when there are a plurality of substituents $R^3$, they may be the same or different. $R^4$ and $R^5$ are each a substituent or a protecting group, and they may be the same or different.

Examples of the substituent include halogens, alkyls, alkenyls, alkynyls, haloalkyls, aryls, heteroaryls, cycloalkyls, cycloalkenyls, cycloalkylalkyls, cyclylalkyls, hydroxyalkyls, alkoxyalkyls, aminoalkyls, heterocyclylalkenyls, heterocyclylalkyls, heteroarylalkyls, silyls, and silyloxyalkyls. The same applies hereinafter.

The protecting group is a functional group that inactivates a highly-reactive functional group, for example. Examples of the protecting group include known protecting groups. Regarding the protecting group, the description in the literature (J. F. W. McOmie, "Protecting Groups in Organic Chemistry", Plenum Press, London and New York, 1973) is incorporated herein by reference, for example. The protecting group is not particularly limited, and examples thereof include a tert-butyldimethylsilyl (TBDMS) group, a bis(2-acetoxyethyloxy)methyl (ACE) group, a triisopropylsilyloxymethyl (TOM) group, a 1-(2-cyanoethoxy)ethyl (CEE) group, a 2-cyanoethoxymethyl (CEM) group, a tolylsulfonylethoxymethyl (TEM) group, and dimethoxytrityl (DMTr). When $R^3$ is $OR^4$, the protecting group is not particularly limited, and examples thereof include a TBDMS group, an ACE group, a TOM group, a CEE group, a CEM group, and a TEM group. Other examples of the protecting group include silyl-containing groups to be described below. The same applies hereinafter.

In the formula (I), $L^1$ is an alkylene chain composed of n atoms. A hydrogen atom(s) on an alkylene carbon atom(s) may or may not be substituted with OH, $OR^n$, $NH_2$, $NHR^a$, $NR^cR^b$, SH, or $SR^a$, for example. Alternatively, $L^1$ may be a polyether chain obtained by substituting at least one carbon atom on the alkylene chain with an oxygen atom. The polyether chain is, for example, polyethylene glycol. When $Y^1$ is NH, O, or S, an atom bound to $Y^1$ in $L^1$ is carbon, an atom bound to $OR^1$ in $L^1$ is carbon, and oxygen atoms are not adjacent to each other. That is, for example, when $Y^1$ is O, this oxygen atom and the oxygen atom in $L^1$ are not adjacent to each other, and the oxygen atom in $OR^1$ and the oxygen atom in $L^1$ are not adjacent to each other.

In the formula (I), $L^2$ is an alkylene chain composed of m atoms. A hydrogen atom(s) on an alkylene carbon atom(s) may or may not be substituted with OH, $OR^c$, $NH_2$, $NR^cR^d$, SH, or $SR^c$, for example. Alternatively, $L^2$ may be a polyether chain obtained by substituting at least one carbon atom on the alkylene chain with an oxygen atom. When $Y^2$ is NH, O, or S, an atom bound to $Y^2$ in $L^2$ is carbon, an atom bound to $OR^2$ in $L^2$ is carbon, and oxygen atoms are not adjacent to each other. That is, for example, when $Y^2$ is O, this oxygen atom and the oxygen atom in $L^2$ are not adjacent to each other, and the oxygen atom in $OR^2$ and the oxygen atom in $L^2$ are not adjacent, to each other.

n of $L^1$ and m of $L^2$ are not particularly limited, and the lower limit of each of them may be 0, for example, and the upper limit of the same is not particularly limited. n and m can be set as appropriate depending on a desired length of the linker region (Lx), for example. For example, from the view point of manufacturing cost, yield, and the like, n and m are each preferably 0 to 30, more preferably 0 to 20, and still more preferably 0 to 15. n and in may be the same (n=m) or different. n+m is, for example, 0 to 30, preferably 0 to 20, and more preferably 0 to 13.

$R^a$, $R^b$, $R^c$, and $R^d$ each independently may be a substituent or a protecting group. The substituent and the protecting group are the same as described above, for example.

In the formula (I), hydrogen atoms each independently may be substituted with a halogen such as Cl, Br, F, or I, for example.

When the linker region (Lx) is represented by the formula (I), the regions (Xc) and (X) are each linked to the linker region (Lx) via —$OR^1$— or —$OR^2$—, for example. $R^1$ and $R^2$ may or may not be present. When $R^1$ and $R^2$ are present, $R^1$ and $R^2$ are each independently a nucleotide residue or the structure represented by the formula (I). When $R^1$ and/or $R^2$ is the nucleotide residue, the linker region (Lx) is composed of the non-nucleotide residue having the structure of the formula (I) excluding the nucleotide residue $R^1$ and/or $R^2$, and the nucleotide residue(s), for example. When $R^1$ and/or $R^2$ is the structure represented by the formula (I), the structure of the linker region (Lx) is such that, for example, two or more of the non-nucleotide residues having the structure of the formula (I) are linked to each other. The number of the structures of the formula (I) may be 1, 2, 3, or 4, for example. When the linker region (Lx) includes a plurality of the structures, the structures of the formula (I) may be linked either directly or via the nucleotide residue(s), for example. On the other hand, when $R^1$ and $R^2$ are not present, the linker region (Lx) is composed of the non-nucleotide residue having the structure of the formula (I) only for example. When the linker region (Lx) is represented by the formula (I), the description as to the linker region (Lx) stated above also applies to the region (Yc), the region (Y), and the linker region (Ly).

The combination of the regions (Xc) and (X) with —$OR^1$— and —$OR^2$—, and the combination of the regions (Yc) and (Y) with —OR¹— and —OR²— are not particularly limited, and may be any of the following conditions, for example.

Condition (1):
the regions (Xc) and (X) are linked to the structure of the formula (I) via —OR²— and —OR¹—, respectively; and
the regions (Yc) and (Y) are linked to the structure of the formula (I) via —OR¹— and —OR²—, respectively.

Condition (2):
the regions (Xc) and (X) are linked to the structure of the formula (I) via —OR²— and —OR¹—, respectively; and
the regions (Yc) and (Y) are linked to the structure of the formula (I) via —OR²— and —OR¹—, respectively.

Condition (3):
the regions (Xc) and (X) are linked to the structure of the formula (I) via —OR¹— and —OR²—, respectively; and
the regions (Yc) and (Y) are linked to the structure of the formula (I) via —OR¹— and —OR²—, respectively.

Condition (4):
the regions (Xc) and (X) are linked to the structure of the formula (I) via —OR¹— and —OR²—, respectively; and
the regions (Yc) and (Y) are linked to the structure of the formula (I) via —OR²— and —OR¹—, respectively.

Examples of the structure of the formula (I) include the structures of the following formulae (I-1) to (I-9). In the following formulae, n and m are the same as in the formula (I). In the following formulae, q is an integer from 0 to 10.

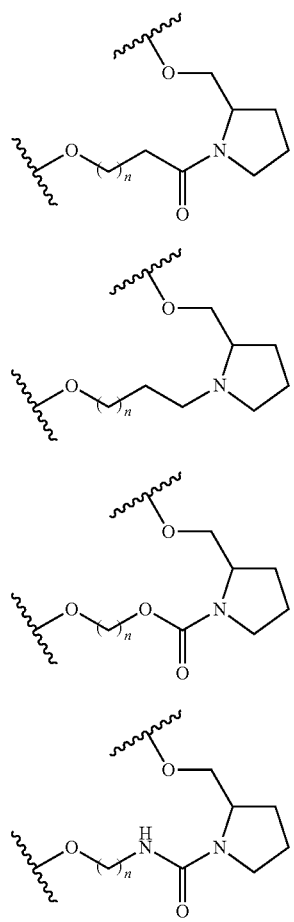

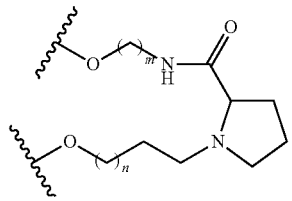

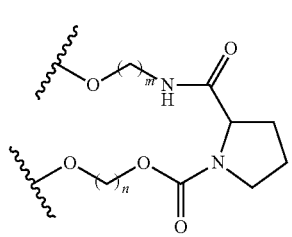

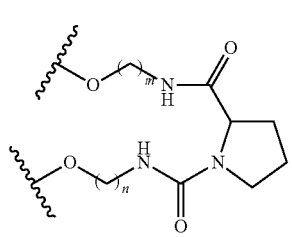

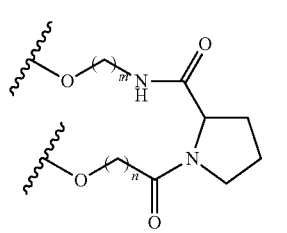

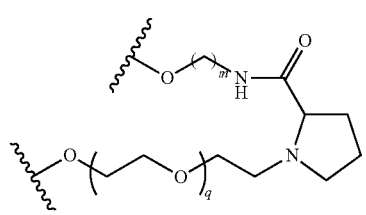

In the formulae (I-1) to (I-9), n, m, and q are not particularly limited, and are as described above. Specific examples are as follows: in the formula (I-1), n=8; in the formula (I-2), n=3; in the formula (I-3), n=4 or 8; in the formula (I-4), n=7 or 8; in the formula (I-5), n=3 and m=4; in the formula (I-6), n=8 and m=4; in the formula (I-7), n=8 and m=4; in the formula (I-8), n=5 and m=4; and in the formula (I-9), q=1 and m=4. The following formula (I-4a) shows an example of the formula (I-4) (n=8), and the following formula (I-6a) shows an example of the formula (I-6) (n=5, m=4).

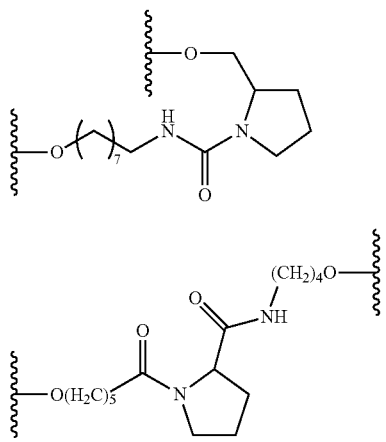

In the present invention, the term "alkyl" encompasses straight-chain and branched alkyl groups, for example. The number of carbon atoms in the alkyl is not particularly limited, and is, for example, 1 to 30, preferably 1 to 6 or 1 to 4. Examples of the alkyl group include: methyl, ethyl, n-propyl, isopropyl, n-butyl, isobutyl, sec-butyl, tert-butyl, n-pentyl, isopentyl, neopentyl, n-hexyl, isohexyl, n-heptyl, n-octyl, n-nonyl, and n-decyl. Among them, methyl, ethyl, n-propyl, isopropyl, n-butyl, isobutyl, sec-butyl, tert-butyl, n-pentyl, isopentyl, neopentyl, n-hexyl, isohexyl, and the like are preferable, for example.

In the present invention, the term "alkenyl" encompasses straight-chain and branched alkenyls, for example. Examples of the alkenyl include the above-described alkyls having one or more double bonds. The number of carbon atoms in the alkenyl is not particularly limited, and is, for example, the same as that in the alkyl, preferably 2 to 8. Examples of the alkenyl include vinyl, 1-propenyl, 2-propenyl, 1-butenyl, 2-butenyl, 3-butenyl, 1,3-butadienyl, and 3-methyl-2-butenyl.

In the present invention, the term "alkynyl" encompasses straight-chain and branched alkynyls, for example. Examples of the alkynyl include the above-described alkyls having one or more triple bonds. The number of carbon atoms in the alkynyl is not particularly limited, and is, for example, the same as that in the alkyl, preferably 2 to 8. Examples of the alkynyl include ethynyl, propynyl, and butynyl. The alkynyl may further include one or more double bonds, for example.

In the present invention, the term "aryl" encompasses monocyclic aromatic hydrocarbon groups and polycyclic aromatic hydrocarbon groups, for example. Examples of the monocyclic aromatic hydrocarbon group include phenyl. Examples of the polycyclic aromatic hydrocarbon group include 1-naphthyl, 2-naphthyl, 1-anthryl, 2-anthryl, 9-anthryl, 1-phenanthryl, 2-phenanthryl, 3-phenanthryl, 4-phenanthryl, and 9-phenanthryl. Among them, phenyl, naphthyls such as 1-naphthyl and 2-naphthyl, and the like are preferable, for example.

In the present invention, the term "heteroaryl" encompasses monocyclic aromatic heterocyclic groups and condensed aromatic heterocyclic groups, for example. Examples of the heteroaryl include furyls (e.g.: 2-furyl, 3-furyl), thienyls (e.g.: 2-thienyl, 3-thienyl), pyrrolyls (e.g.: 1-pyrrolyl, 2-pyrrolyl, 3-pyrrolyl), imidazolyls (e.g.: 1-imidazolyl, 2-imidazolyl, 4-imidazolyl), pyrazolyls (e.g.: 1-pyrazolyl, 3-pyrazolyl, 4-pyrazolyl), triazolyls (e.g.: 1,2,4-triazole-1-yl, 1,2,4-tetrazolyl-3-yl, 1,2,4-triazole-4-yl), tetrazolyls (e.g.: 1-tetrazolyl, 2-tetrazolyl, 5-tetrazolyl), oxazolyls (e.g.: 2-oxazolyl, 4-oxazolyl, 5-oxazolyl), isoxazolyls (e.g.: 3-isoxazolyl, 4-isoxazolyl, 5-isoxazolyl), thiazolyls (e.g.: 2-thiazolyl, 4-thiazolyl, 5-thiazolyl), thiadiazolyls, isothiazolyls (e.g.: 3-isothiazolyl, 4-isothiazolyl, 5-isothiazolyl), pyridyls (e.g.: 2-pyridyl, 3-pyridyl, 4-pyridyl), pyridazinyls (e.g.: 3-pyridazinyl, 4-pyridazinyl), pyrimidinyls (e.g.: 2-pyrimidinyl, 4-pyrimidinyl, 5-pyrimidinyl), furazanyls (e.g.: 3-furazanyl), pyrazinyls (e.g.: 2-pyrazinyl), oxadiazolyls (e.g.: 1,3,4-oxadiazole-2-yl), benzofuryls (e.g.: 2-benzo[b]furyl, 3-benzo[b]furyl, 4-benzo[b]furyl, 5-benzo[b]furyl, 6-benzo[b]furyl, 7-benzo[b]furyl), benzothienyls (e.g.: 2-benzo[b]thienyl, 3-benzo[b]thienyl, 4-benzo[b]thienyl, 5-benzo[b]thienyl, 6-benzo[b]thienyl, 7-benzo[b]thienyl), benzimidazolyls (e.g.: 1-benzimidazolyl, 2-benzimidazolyl, 4-benzimidazolyl, 5-benzimidazolyl), dibenzofuryls, benzoxazolyls, benzothiazolyls, quinoxalyls (e.g.: 2-quinoxalinyl, 5-quinoxalinyl, 6-quinoxalinyl), cinnolinyls (e.g.: 3-cinnolinyl, 4-cinnolinyl, 5-cinnolinyl, 6-cinnolinyl, 7-cinnolinyl, 8-cinnolinyl), quinazolyls (e.g.: 2-quinazolinyl, 4-quinazolinyl, 5-quinazolinyl, 6-quinazolinyl, 7-quinazolinyl, 8-quinazolinyl), quinolyls (e.g.: 2-quinolyl, 3-quinolyl, 5-quinolyl, 6-quinolyl, 7-quinolyl, 8-quinolyl), phthalazinyls (e.g.: 1-phthalazinyl, 5-phthalazinyl, 6-phthalazinyl), isoquinolyls (e.g.: 1-isoquinolyl, 3-isoquinolyl, 4-isoquinolyl, 5-isoquinolyl, 6-isoquinolyl, 7-isoquinolyl, 8-isoquinolyl), puryls, pteridinyls (e.g.: 2-pteridinyl, 4-pteridinyl, 6-pteridinyl, 7-pteridinyl), carbazolyls, phenanthridinyls, acridinyls (e.g.: 1-acridinyl, 2-acridinyl, 3-acridinyl, 4-acridinyl, 9-acridinyl), indolyls (e.g.: 1-indolyl, 2-indolyl, 3-indolyl, 4-indolyl, 5-indolyl, 6-indolyl, 7-indolyl), isoindolyls, phenazinyls (e.g.: 1-phenazinyl, 2-phenazinyl), and phenothiazinyls (e.g.: 1-phenothiazinyl, 2-phenothiazinyl, 3-phenothiazinyl, 4-phenothiazinyl).

In the present invention, the term "cycloalkyl" refers to cyclic saturated hydrocarbon groups, for example, and the number of carbon atoms in the cycloalkyl is 3 to 15, for example. Examples of the cycloalkyl include cyclopropyl, cyclobutyl, cyclopentyl, cyclohexyl, cycloheptyl, cyclooctyl, bridged cyclic hydrocarbon groups, and spiro hydrocarbon groups. Among them, cyclopropyl, cyclobutyl, cyclopentyl, cyclohexyl, bridged cyclic hydrocarbons, and the like are preferable.

In the present invention, examples of the "bridged cyclic hydrocarbon groups" include bicyclo[2.1.0]-pentyl, bicyclo[2.2.1]heptyl, bicyclo[2.2.2]octyl, and bicyclo[3.2.1]octyl, tricyclo[2.2.1.0]heptyl, bicyclo[3.3.1]nonane, 1-adamantyl, and 2-adamantyl.

In the present invention, examples of the "spiro hydrocarbon groups" include spiro[3.4]octyl.

In the present invention, the term "cycloalkenyl" encompasses unsaturated cyclic aliphatic hydrocarbon groups, for example, and the number of carbon atoms in the cycloalkenyl is 3 to 7, for example. Examples of the cycloalkenyl group include cyclopropenyl, cyclobutenyl, cyclopentenyl, cyclohexenyl, and cycloheptenyl. Among them, cyclopropenyl, cyclobutenyl, cyclopentenyl, cyclohexenyl, and the like are preferable. The term "cycloalkenyl" also encompasses bridged cyclic hydrocarbon groups and spiro hydrocarbon groups having an unsaturated bond in their rings, for example.

In the present invention, examples of the "arylalkyl" include benzyl, 2-phenethyl, and naphthalenylmethyl. Examples of the "cycloalkylalkyl" and "cyclylalkyl" include cyclohexylmethyl and adamantylmethyl. Examples of the "hydroxyalkyl" include hydroxymethyl and 2-hydroxyethyl.

In the present invention, the "alkoxy" encompasses groups composed of any of the above-described alkyls and oxygen (alkyl-O-groups), and examples thereof include methoxy, ethoxy, n-propoxy, isopropoxy, and n-butoxy. Examples of the "alkoxyalkyl" include methoxymethyl. Examples of the "aminoalkyl" include 2-aminoethyl.

In the present invention, examples of the "heterocyclyl" include 1-pyrrolinyl, 2-pyrrolinyl, 3-pyrrolinyl, 1-pyrrolidinyl, 2-pyrrolidinyl, 3-pyrrolidinyl, pyrrolidinone, 1-imidazoliny, 2-imidazoliny, 4-imidazoliny, 1-imidazolidinyl, 2-imidazolidinyl, 4-imidazolidinyl, imidazolidinone, 1-pyrazolinyl, 3-pyrazolinyl, 4-pyrazolinyl, 1-pyrazolidinyl, 3-pyrazolidinyl, 4-pyrazolidinyl, piperidinone, piperidino, 2-piperidinyl, 3-piperidinyl, 4-piperidinyl, 1-piperazinyl, 2-piperazinyl, piperazinone, 2-morpholinyl, 3-morpholinyl, morpholino, tetrahydropyranyl, and tetrahydrofuranyl.

In the present invention, examples of the "heterocyclylalkyl" include piperidinylmethyl and piperazinylmethyl. Examples of the "heterocyclylalkenyl" include 2-piperidinyl ethenyl. Examples of the "heteroarylalkyl" include pyridylmethyl and quinoline-3-ylmethyl.

In the present invention, the term "silyl" encompasses groups represented by the formula $R_3Si-$, where R independently can be selected from the above-described alkyls, aryls, and cycloalkyls. Examples of the silyl include a trimethylsilyl group and a tert-butyldimethylsilyl group. Examples of the "silyloxy" include a trimethylsilyloxy group. Examples of the "silyloxyalkyl" include trimethylsilyloxymethyl.

In the present invention, examples of the "alkylene" include methylene, ethylene, and propylene.

In the present invention, the above-described various groups may be substituted. Examples of the substituent include hydroxy, carboxy, halogens, alkyl halides (e.g.: $CF_3$, $CH_2CF_3$, $CH_2CCl_3$), nitro, nitroso, cyano, alkyls (e.g.: methyl, ethyl, isopropyl, tert-butyl), alkenyls (e.g.: vinyl), alkenyls (e.g.: ethynyl), cycloalkyls (e.g.: cyclopropyl, adamantyl), cycloalkylalkyls (e.g.: cyclohexylmethyl, adamantylmethyl), cycloalkenyls (e.g.: cyclopropenyl), aryls (e.g.: phenyl, naphthyl), arylalkyls (e.g.: benzyl, phenethyl), heteroaryls (e.g.: pyridyl, furyl), heteroarylalkyls pyridylmethyl), heterocyclyls (e.g.: piperidyl), heterocyclylalkyls (e.g.: morpholylmethyl), alkoxys (e.g.: methoxy, ethoxy, propoxy, butoxy), halogenated alkoxys (e.g.: $OCF_3$) alkenyloxys (e.g.: vinyloxy, allyloxy), aryloxys (e.g.: phenyloxy), alkyloxycarbonyls (e.g.: methoxycarbonyl, ethoxycarbonyl, tert-butoxycarbonyl), arylalkyloxys (e.g.: benzyloxy), aminos [alkylaminos (e.g.: methylamino, ethylamino, dimethylamino), acylaminos (e.g.: acetylamino, benzoylamino), arylalkylaminos (e.g.: benzylamino, tritylamino), hydroxyamino], alkylaminoalkyls (e.g.: diethylaminomethyl), sulfamoyl, and oxo.

4. Synthesis Method of ssNC Molecule of the Present Invention

The method for synthesizing the ssNc molecule of the present invention is not particularly limited, and a conventionally known method can be employed. Examples of the method include synthesis methods according to genetic engineering procedures and chemical synthesis methods. Examples of the genetic engineering procedures include: synthesis methods utilizing in vitro transcription; methods using a vector; and methods carried out using a PCR cassette. The vector is not particularly limited, and examples thereof include non-virus vectors such as plasmid, and virus vectors. The chemical synthesis methods are not particularly limited, and examples thereof include a phosphoramidite method and an H-phosphonate method. The chemical synthesis methods can be carried out using a commercially available automated nucleic acid synthesizer, for example. In the chemical synthesis methods, an amidite generally is used. The amidite is not particularly limited. Examples of commercially available amidites include RNA Phosphoramidites (2'-O-TBDMSi, trade name, Samchully Pharm. Co., Ltd.). ACE amidite, TOM amidite. CEE amidite, CEM amidite, and TEM amidite.

5. Composition

The inhibitory composition according to the present invention is, as described above, a composition for inhibiting the expression of a target gene, containing the ssNc molecule of the present invention. The composition of the present invention is characterized in that it contains the ssNc molecule of the present invention, and other configurations are by no means limited. The inhibitory composition of the present invention also can be referred to as an inhibitory reagent, for example.

According to the present invention, for example, by administering the composition to a subject in which the target gene is present, it is possible to inhibit the expression of the target gene.

Furthermore, as described above, the pharmaceutical composition according to the present invention contains the ssNc molecule of the present invention. The pharmaceutical composition of the present invention is characterized in that it contains the ssNc molecule of the present invention, and other configurations are by no means limited. The pharmaceutical composition of the present invention also can be referred to as a pharmaceutical, for example.

According to the present invention, for example, by administering the pharmaceutical composition to a patient with a disease caused by a gene, it is possible to inhibit the expression of the gene, thereby treating the disease. In the present invention, the term "treatment" encompasses: prevention of diseases; improvement of diseases; and improvement in prognosis, for example, and it can mean any of them.

In the present invention, a disease to be treated is not particularly limited, and examples thereof include diseases caused by the expression of genes. Depending on the kind of the disease, a gene that causes the disease may be set as the target gene, and further, depending on the target gene, the expression inhibitory sequence may be set as appropriate.

A specific example is as follows. By setting the TGF-β1 gene as the target gene and incorporating an expression inhibitory sequence for this gene into the ssNc molecule, the ssNc molecule can be used for the treatment of inflammatory diseases, specifically, acute lung injury and the like, for example.

The method of using the inhibitory composition and the pharmaceutical composition according to the present invention (hereinafter, both the compositions simply are referred to as "the compositions") are not particularly limited, and examples thereof include administering the ssNc molecule to a subject having the target gene.

Examples of the subject to which the ssNc molecule of the present invention is administered include cells, tissues, and organs. Examples of the subject also include humans and nonhuman animals such as nonhuman mammals, i.e., mammals excluding humans. The administration may be performed in vivo or in vitro, for example. The cells are not particularly limited, and examples thereof include: various cultured cells such as HeLa cells, 293 cells, NIH3T3 cells, and COS cells; stern cells such as ES cells and hematopoietic stem cells; and cells isolated from living organisms, such as primary cultured cells.

The administration method is not particularly limited, and can be determined as appropriate depending on the subject, for example. When the subject is a cultured cell, the administration method may be a method using a transfection reagent, an electroporation method, or the like, for example.

Each of the compositions of the present invention may contain only the ssNc molecule of the present invention or further may contain an additive(s) in addition to the ssNc molecule, for example. The additive is not particularly limited, and preferably is a pharmaceutically acceptable additive, for example. The kind of the additive is not particularly limited, and can be selected as appropriate depending on the kind of the subject, for example.

In the composition of the present invention, the ssNc molecule may form a complex with the additive, for example. The additive also can be referred to as a complexing agent, for example. The formation of the complex allows the ssNc molecule to be delivered efficiently, for example. The bond between the ssNc molecule and the complexing agent is not particularly limited, and examples thereof include noncovalent bond. The complex may be an inclusion complex, for example.

The complexing agent is not particularly limited, and examples thereof include polymers, cyclodextrins, and adamantine. Examples of the cyclodextrins include linear cyclodextrin copolymers and linear oxidized cyclodextrin copolymers.

Other examples of the additive include a carrier, a binding substance that binds to a target cell, a condensing agent, a fusogenic agent, and an excipient.

The carrier preferably is a polymer, more preferably a biopolymer, for example. Preferably, the carrier is biodegradable, for example. Examples of the carrier include: proteins such as human serum albumin (HSA), low-density lipoprotein (LDL), and globulin; carbohydrates such as, for example, dextran, pullulan, chitin, chitosan, inulin, cyclodextrin, and hyaluronic acid; and lipids. As the carrier, a synthetic polymer such as a synthetic polyamino acid also can be used, for example. Examples of the polyamino acid include polylysine (PLL), poly L-aspartic acid, poly L-glutamic acid, styrene-maleic anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymer, and polyphosphazine.

Examples of the binding substance include thyroid-stimulating hormone, melanocyte-stimulating hormone, lectin, glycoproteins, surfactant protein A. Mucin carbohydrate, multivalent lactose, multivalent galactose. N-acetyl-galactosamine, N-acetyl-gulucosamine, multivalent mannose, multivalent fucose, glycosylated polyamino acid, multivalent galactose, transferrin, bisphosphonate, polyglutamic acid, polyaspartic acid, lipids, cholesterol, steroids, bile acid, folate, vitamin B12, biotin, Neproxin, RGD peptide, and RGD peptide mimetic.

Examples of the fusogenic agent and the condensing agent include polyamino chains such as polyethyleneimine (PEI). PEI may be either linear or branched, and also, may be either synthetic or naturally occurring, for example. The PEI may be substituted with an alkyl or a lipid, for example. As the fusogenic agent, it is also possible to use polyhistidine, polyimidazole, polypyridine, polypropyleneimine, mellitin, a polyacetal substance (e.g., cationic polyacetal or the like), or the like, for example. The fusogenic agent may have an α-helix structure, for example. The fusogenic agent may be a membrane disruptive agent such as mellitin, for example.

As to the compositions according to the present invention, for example, the descriptions regarding the formation of the complex and the like in U.S. Pat. No. 6,509,323, U.S. Patent Publication No. 2003/0008818, PCT/US04/07070, and the like are incorporated herein by reference.

Other examples of the additive include amphiphilic molecules. The amphiphilic molecule is a molecule having a hydrophobic region and a hydrophilic region, for example. The molecule preferably is a polymer, for example. The polymer may have, for example, a secondary structure, preferably a repeating secondary structure. Specifically, polypeptide is preferable, and α-helix polypeptide and the like are more preferable, for example.

The amphiphilic polymer may be a polymer having two or more amphiphilic subunits, for example. Examples of the subunit include subunits with a cyclic structure having at least one hydrophilic group and one hydrophobic group. The subunit may contain steroid such as cholic acid, an aromatic structure, and the like, for example. The polymer may contain, for example, both a cyclic structure subunit, such as an aromatic subunit, and an amino acid.

6. Inhibitory Method

The inhibitory method according to the present invention is, as described above, a method for inhibiting the expression of a target gene, in which the ssNc molecule of the present invention is used. The inhibitory method of the present invention is characterized in that the ssNc molecule of the present invention is used therein, and other steps and conditions are by no means limited.

In the inhibitory method of the present invention, the mechanism by which the gene expression is inhibited is not particularly limited, and examples thereof include inhibition of the expression by RNA interference or an RNA interference-like phenomenon. The inhibitory method of the present invention is, for example, a method for inducing RNA interference that inhibits the expression of a target gene, and it also can be referred to an inhibitory method that is characterized in that the ssNc molecule of the present invention is used therein.

The inhibitory method of the present invention includes the step of administering the ssNc molecule to a subject in which the target gene is present, for example. By the administration step, the ssNc molecule is brought into contact with the subject to which the ssNc molecule is administered, for example. Examples of the subject include cells, tissues, and organs. Examples of the subject also include humans and nonhuman animals such as nonhuman mammals, i.e., mammals excluding humans. The administration may be performed in vivo or in vitro, for example.

In the inhibitory method of the present invention, the ssNc molecule may be administered alone, or the composition of the present invention containing the ssNc molecule may be administered, for example. The administration method is not particularly limited, and can be selected as appropriate depending on the kind of the subject, for example.

7. Treatment Method

As described above, the method for treating a disease according to the present invention includes the step of administering the ssNc molecule of the present invention to a patient, and the ssNc molecule includes, as the expression inhibitory sequence, a sequence that inhibits expression of a gene causing the disease. The treatment method of the present invention is characterized in that the ssNc molecule of the present invention is used therein, and other steps and conditions are by no means limited.

The description regarding the inhibitory method of the present invention also applies to the treatment method of the present invention, for example. The administration method is not particularly limited, and may be either oral administration or parenteral administration, for example.

8. Use of ssNc Molecule

The use according to the present invention is the use of the ssNc molecule of the present invention for inhibiting the expression of a target gene. Also, the use according to the present invention is the use of the ssNc molecule of the present invention for inducing RNA interference.

The nucleic acid molecule according to the present invention is a nucleic acid molecule for use in treatment of a disease. The nucleic acid molecule is the ssNc molecule of the present invention, and the ssNc molecule includes, as the expression inhibitory sequence, a sequence that inhibits expression of a gene causing the disease.

In the following, the present invention will be described in detail with reference to examples and the like. It is to be noted, however, that the present invention is by no means limited thereto.

EXAMPLES

Example A1

Synthesis of RNA

As RNA (Ex) of the present example, ssRNA (NK-0016) shown below was synthesized. NK-0016 includes a 19-mer expression inhibitory sequence (SEQ ID NO: 1) that inhibits expression of the GAPDH gene. In the sequence of NK-0016, a region between a region (Xc) and a region (X) is a linker region (Lx), and a region between a region (Y) and a region (Yc) is a linker region (Ly) (hereinafter the same). In this sequence, the 5' region (Xc) and the 3' region (Yc) are indicated with lower-case letters (hereinafter the same).

Expression inhibitory sequence for the GAPDH gene (SEQ ID NO: 1)

```
5'-GUUGUCAUACUUCUCAUGG-3'
```

```
Ex: NK-0016 (SEQ ID NO: 2)
5' - caugagaaguaugacaacagccCCACACCGGCUGUUGUCAUACUUCUCAUGGUUCUUCGgaa - 3'
          |_____Xc_____|  |_____X_____|  |___Y___||_Yc_|
```

As RNA of a comparative example, dsRNA (NI-0011) shown below as an RNAi positive control (Pc) was synthesized. NI-0011 has an overhang of two bases at the 3' end of each single strand, and the single strand of SEQ ID NO: 4 has the above-described 19-mer expression inhibitory sequence, similarly to NK-0016.

```
Pc: NI-0011
5'- CCAUGAGAAGUAUGACAACAG -3'    (SEQ ID NO: 3)

3'- UUGGUACUCUUCAUACUGUUG -5'    (SEQ ID NO: 4)
```

The RNAs were synthesized based on a phosphoramidite method with the use of a nucleic acid synthesizer (trade name: ABI Expedite (registered trademark) 8909 Nucleic Acid Synthesis System, Applied Biosystems). In the synthesis. RNA Phosphoramidites (2'-O-TBDMSi, trade name, Samchully Pharm. Co., Ltd.) were used as RNA amidites (the same applies hereinafter). The amidites were deprotected by a conventional method. The synthesized RNAs were purified by HPLC. Each of the purified RNAs was lyophilized. In the following examples, synthesis of RNAs was carried out in the same manner as in the present example, unless otherwise stated.

The lyophilized RNA was dissolved in distilled water for injection (Otsuka Pharmaceutical Co., Ltd., hereinafter the same) so as to achieve desired concentrations.

Example A2

Inhibitory Effect on the GAPDH Gene Expression in HCT116 Cells

Using the ssRNA of the present invention, inhibition of the GAPDH gene expression in vitro was examined.

(1) Materials and Method

As RNA (Ex) of the present example, ssRNA (NK-0016) of Example A1 was used.

RNA solutions were prepared by dissolving the RNA in distilled water for injection so as to achieve desired concentrations. HCT116 cells (DS Pharma Biomedical Co., Ltd.) were used as cells. A 10% FBS-containing McCoy's 5A (Invitrogen) medium was used as a medium. The culture conditions were set to 37° C. and 5% $CO_2$.

First, the HCT116 cells were cultured in the medium, and were dispensed to a 24 well plate so that each well contained 400 µl of the medium to achieve a density of $2 \times 10^4$ cells/well. The cells in the wells were cultured for another 24 hours. Thereafter, the cells were transfected with the RNA using a transfection reagent Lipofectamine 2000 (trade name, Invitrogen) according to the protocol supplied therewith. Specifically, the transfection was carried out by setting the composition per well as follows. The final concentration of the RNA in the well was set to 5 nmol/l, 10 nmol/l, 20 nmol/l, or 40 nmol/l.

TABLE 1

| (Composition per well: µl) | |
|---|---|
| Medium | 400 |
| (A) Lipofectamine 2000 | 1.5 |

TABLE 1-continued

| (Composition per well: μl) | |
| --- | --- |
| (B) Opti-MEM (Invitrogen) | 98 |
| (C) RNA solution | 0.5 |
| Total | 500 |

After the transfection, the cells in the wells were cultured for 48 hours, and then, the RNA was collected using an RNeasy Mini Kit (trade name, Qiagen) according to the protocol supplied therewith. Subsequently, cDNA was synthesized from the RNA using a reverse transcriptase (trade name: SuperScript III, invitrogen) according to the protocol supplied therewith. Then, PCR was carried out using the thus-synthesized cDNA as a template, and the expression level of the GAPDH gene and that of the β-actin gene as an internal standard were measured. The expression level of the GAPDH gene was corrected with reference to that of the β-actin gene.

The PCR was carried out using a LightCycler FastStart DNA Master SYBR Green I (trade name, Roche) as a reagent and a Light Cycler DX400 (trade name, Roche) as an instrument (hereinafter the same). The GAPDH gene and the β-actin gene were amplified using the following primer sets, respectively.

```
Primer set for GAPDH gene
5'-GGAGAAGGCTGGGGCTCATTTGC-3'      (SEQ ID NO: 9)

5'-TGGCCAGGGGTGCTAAGCAGTTG-3'      (SEQ ID NO: 10)

Primer set for β-actin gene
5'-GCCACGGCTGCTTCCAGCTCCTC-3'      (SEQ ID NO: 11)

5'-AGGTCTTTGCGGATGTCCACGTCAC-3'    (SEQ ID NO: 12)
```

As Control 1, regarding the cells to which 100 μl of (B) only had been added, the expression levels of the genes also were measured (−). Furthermore, as Control 2, regarding the cells subjected to the same transfection procedures as in the above except that the RNA solution was not added and that (B) and 1.5 μl of (A) were added so that the total amount of (A) and (B) would be 100 μl, the expression level of the gene also was measured (mock).

Then, the corrected expression level of the GAPDH gene in the control (−) was set as 1, and that in the cells transfected with the RNA at each concentration was presented as the relative value to that in the control (−).

(2) Results

Figure 4:
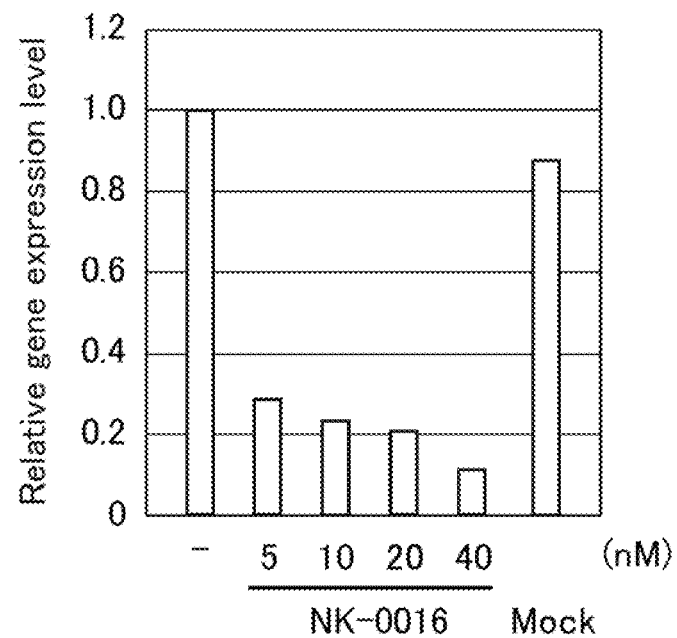
FIG. 4 is a graph showing the relative expression level of the GAPDH gene in an example of the present invention.

The results thereof are shown in FIG. 4. FIG. 4 is a graph showing the relative expression level of the GAPDH gene. As can be seen from FIG. 4, when NK-0016 was used, the expression amount was smaller than that in the control (−) to which the RNA was not added. Thus, it was found that NK-0016 inhibits the expression of the GAPDH gene. Also, as can be seen from FIG. 4, it was found that NK-0016 exhibits an inhibitory effect in a dose-dependent manner.

Example A3

Inhibitory Effect on the GAPDH Gene Expression in HCT116 Cells

Using the ssRNA of the present invention, inhibition of the GAPDH gene expression in vitro was examined.

(1) Materials and Method

As RNA (Ex) of the present example, the ssRNA (NK-0016) of Example A1 was used. As RNA of a comparative example, the dsRNA (NI-0011) as an RNAi positive control (Pc) was used. RNA solution was prepared by dissolving each of the RNAs in distilled water for injection so as to achieve a concentration of 40 μmol/l.

The expression level of the GAPDH gene in the HCT116 cells was examined in the same manner as in Example A2, except that the above RNA solution was used. The RNA concentration at the time of transfection was set to 40 nmol/l.

(2) Results

Figure 5:
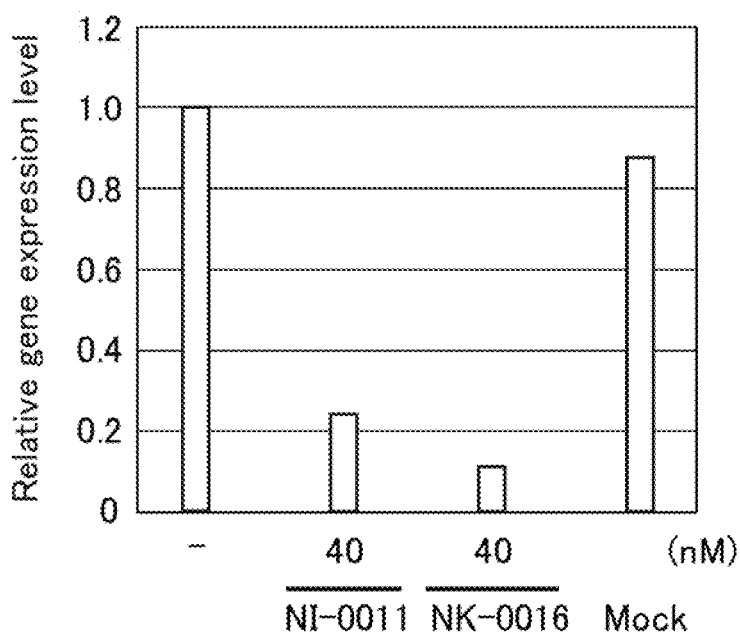
FIG. 5 is a graph showing the relative expression level of the GAPDH gene in another example of the present invention.

The results thereof are shown in FIG. 5. FIG. 5 is a graph showing the relative expression level of the GAPDH gene, and the vertical axis indicates the relative gene expression amount. As can be seen from FIG. 5, NK-0016 of the example exhibited a very powerful inhibitory activity, as compared with NI-0011 of the comparative example.

Example A4

Inhibitory Effect on the GAPDH Gene Expression in A549 Cells and 293 Cells

Using the ssRNA of the present invention, inhibition of the GAPDH gene expression in vitro was examined.

(1) Materials and Method

As RNAs (Ex) of the present example, NK-0016 of Example A1 and Ex-ssRNA (PK-0004) shown below were used. In PK-0004, a linker region (Lx) and a linker region (Ly) were provided by linking Compound 10 (L-proline-diamide-amidite) in Scheme 3 shown in the Examples B between Xc and X and between Yc and Y, respectively. The chemical formula of both the linkers is shown below. The sequences of NK-0016 and PK-0004 are identical except for the linker region (Lx) between Xc and X and the linker region (Ly) between Yc and Y.

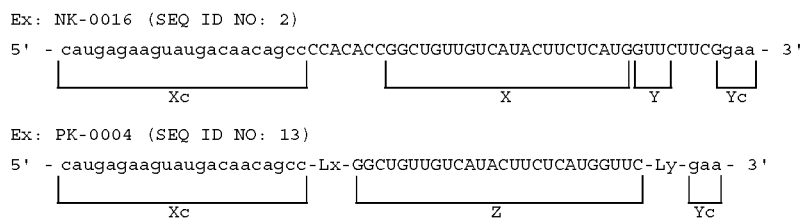

-continued

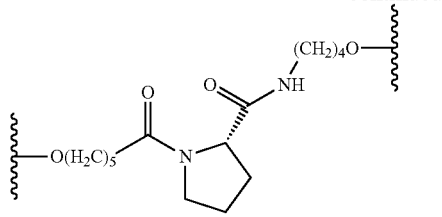

RNA solution was prepared by dissolving each of the RNAs in distilled water for injection so as to achieve a concentration of 20 μmol/l. A549 cells and 293 cells (DS Pharma Biomedical Co., Ltd.) were used as cells. As a medium for the former cells, a 10% FBS-containing DMEM (Invitrogen) was used. As a medium for the latter cells, a 10% FBS-containing MEM (Invitrogen) was used. The culture conditions were set to 37° C. and 5% $CO_2$.

First, the cells of each type were cultured in the medium, and were dispensed to a 24-well plate so that each well contained 400 μl of the medium to achieve a density of $5×10^4$ cells/well. The cells in the wells were cultured for another 24 hours. Thereafter, the cells were transfected with the RNA using a transfection reagent Lipofectamine 2000 (trade name, Invitrogen) according to the protocol supplied therewith. Specifically, the transfection was carried out by setting the composition per well as follows for the A549 cells and the 293 cells. In the following composition, (B) is Opti-MEM (trade name, Invitrogen), and (C) is the RNA solution of 20 μmol/l, and they were added so that the total amount of (B) and (C) would be 98.5 μl or 99 μl. The final concentration of the RNA in the well was set to 1 nmol/l, 3 nmol/l, or 10 nmol/l.

TABLE 2

(Composition per well: μl)

|  | A549 cells | 293 cells |
| --- | --- | --- |
| Medium | 400 | 400 |
| (A) Lipofectamine 2000 | 1.5 | 1 |
| (B) + (C) | 98.5 | 99 |
| Total | 500 | 500 |

After the transfection, the cells were cultured for 48 hours. Then, collection of the RNA, synthesis of cDNA, and PCR were carried out in the same manner as in Example A2, and the relative expression amount of the GAPDH gene was determined.

(2) Results

Figure 6:
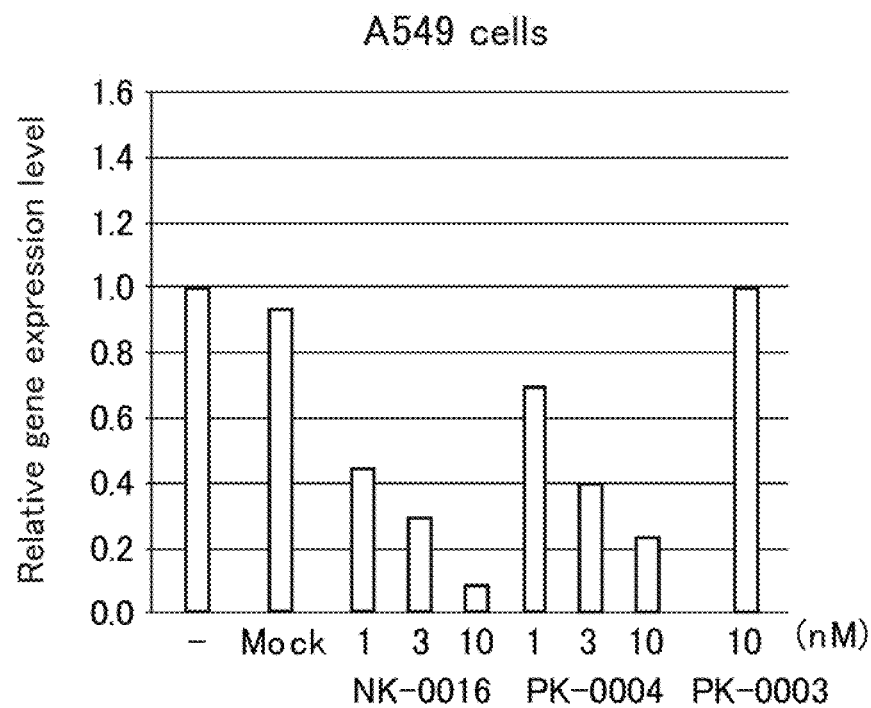
FIG. 6 is a graph showing the relative expression level of the GAPDH gene in A549 cells in still another example of the present invention
Figure 7:
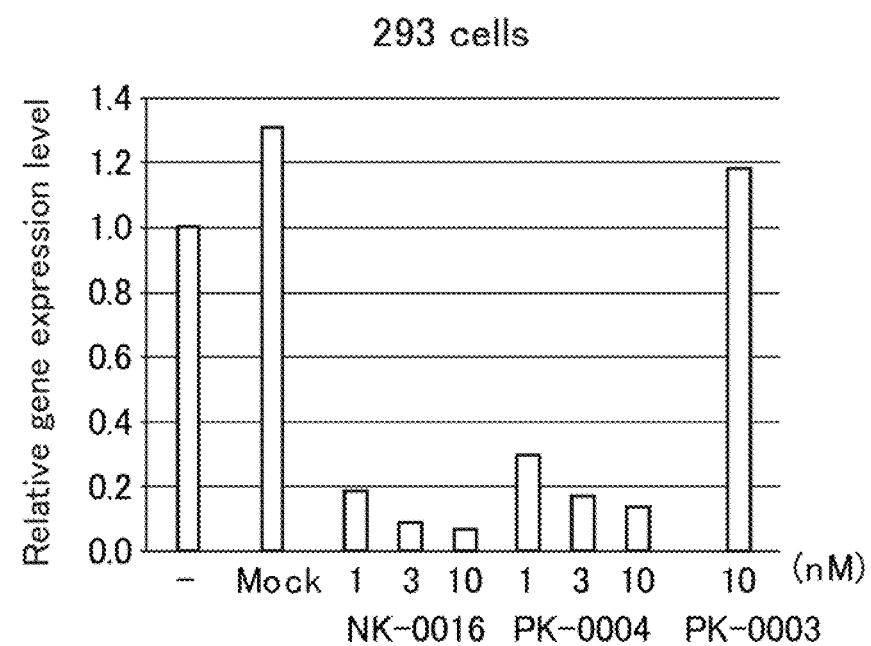
FIG. 7 is a graph showing the relative expression level of the GAPDH gene in 293 cells in the example of the present invention.

The results thereof are shown in FIGS. 6 and 7. FIG. 6 shows the result obtained regarding the A549 cells, and FIG. 7 shows the result obtained regarding the 293 cells. FIGS. 6 and 7 are each a graph showing the relative expression level of the GAPDH gene. As can be seen from FIGS. 6 and 7, it was found that NK-0016 and PK-0004 according to the present example exhibit a potent inhibitory activity, and they exhibit an inhibitory effect in a concentration-dependent manner.

Example A5

Inhibitory Effects on the TGF-β1 Gene Expression in Hepa1-6 Cells

Regarding the ssRNA of the present invention, the effect of inhibiting the TGF-β1 gene expression in vitro was examined.

(1) Materials and Method

As RNA (Ex) of the present example, ssRNA (NK-0033) shown below was used. NK-0033 includes the following 21-mer sequence that inhibits the expression of the TGF-β1 gene. This sequence was designed based on the siRNA used by Cheng et al. (Mol. Pharm., 2009, 6, pp. 772-779). TGF-β1 gene expression inhibitory sequence (SEQ ID NO: 16)

5'-AAAGUCAAUGUACAGCUGCUU-3'

As RNA of a comparative example, ssRNA (NK-0035) shown below as an RNAi negative control (Nc) was used. NK-0035 was designed so as to incorporate, instead of the expression inhibitory sequence, a scrambled sequence that is not involved in the expression inhibition.

```
Ex: NK-0033 (SEQ ID NO: 80)
5'-cagcuguacauugacuuuagccCCACACCGGCUAAAGUCAAUGUACAGCUGCUUCUUCGgaa-3'
   |_____|  |_____|  |__|
             Xc                           Z                    Yc Nc: NK-0035 (SEQ ID NO: 15)
5'-ugucagugcucauuuacaagccCCACACCGGCUUGUAAAUGAGCACUGACACUUCUUCGgaa-3'
   |_____|  |_____|  |__|
             Xc                           Z                    Yc
```

RNA solution was prepared by dissolving each of the RNAs in distilled water for injection. Hepa1-6 cells (The RIKEN BioResource Center) were used as cells, and a 10% FBS-containing DMEM (Invitrogen) was used as a medium. The culture conditions were set to 37° C. and 5% CO.

First, the Hepa1-6 cells were cultured in the medium, and were dispensed to a 24-well plate so that each well contained 400 μl of the medium to achieve a density of $3×10^4$ cells/well. The cells in the wells were cultured for another 24 hours.

Thereafter, the cells were transfected with the ssRNA using a transfection reagent Lipofectamine 2000 (trade name, Invitrogen) according to the protocol supplied therewith. Specifically, the transfection was carried out by setting the composition per well as follows. In the following composition, (B) is Opti-MEM (trade name. Invitrogen), and (C) is the RNA solution of 20 μmol/l, and they were added so that the total amount of (B) and (C) would be 98.5 μl. The final concentration of the RNA in the well was set to 10 nmol/l, 25 nmol/l, 50 nmol/l, or 100 nmol/l.

TABLE 3

| (Composition per well: μl) | |
| --- | --- |
| Medium | 400 |
| (A) Lipofectamine 2000 | 1.5 |
| (B) + (C) | 98.5 |
| Total | 500 |

After the transfection, the cells in the wells were cultured for 48 hours, and then, the RNA was collected using an RNeasy Mini Kit (trade name, Qiagen) according to the protocol supplied therewith. Subsequently, cDNA was synthesized from the RNA using a reverse transcriptase (trade name: SuperScript III, Invitrogen) according to the protocol supplied therewith. Then, PCR was carried out in the same manner as in Example A2, except that the following primer set for TGF-β1 gene and the following primer set for the β-actin gene were used, and the expression level of the TGF-β1 gene and that of the β-actin gene as an internal standard were measured. The expression level of the TGF-β1 gene was corrected with reference to that of the β-actin gene.

```
Primer set for TGF-β1 gene
5'-CCATTGCTGTCCCGTGCAGAGCTG-3'    (SEQ ID NO: 17)

5'-ATGGTAGCCCTTGGGCTCGTGGATC-3'   (SEQ ID NO: 18)

Primer set for β-actin gene amplification
5'-GTCGTACCACAGGCATTGTGATGG-3'    (SEQ ID NO: 19)

5'-GCAATGCCTGGGTACATGGTGG-3'      (SEQ ID NO: 20)
```

Regarding each of the control (−) and the control (mock), the expression level was measured in the same manner as in Example A2. The corrected expression level of the TGF-β1 gene in the control (−) was set as 1, and that in the cells transfected with each RNA was presented as the relative value to that in the control.

(2) Results

Figure 8:
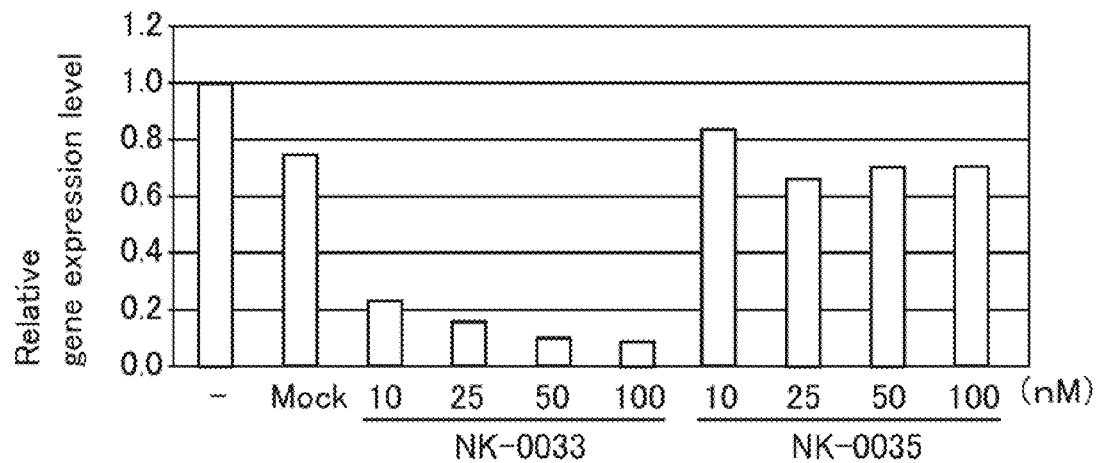
FIG. 8 is a graph showing the expression level of the TGF-β1 gene in still another example of the present invention.

The results thereof are shown in FIG. 8. FIG. 8 is a graph showing the relative expression level of the TGF-β1 gene. As can be seen from FIG. 8, NK-0033 according to the example inhibited the expression of the TGF-β1 gene in vitro. On the other hand, NK-0035 as a negative control did not inhibit the expression of the TGF-β1 gene.

Example A6

Inhibitory Effects on TGF-β1 Gene Expression and Acute Lung Injury In Vivo

Regarding the ssRNA of the present invention, the inhibitory effects on the expression and the acute lung injury in vivo were examined. These effects were examined according to the method described in Takagi et al. (J. Thromb Hemost 2009: 7: pp. 2053-2063).

(1) Materials and Method (1.1) Administration of ssRNAs to Mice with Acute Lung Injury As RNA (Ex) of the present example, the ssRNA (NK-0033) of Example A5 was used. As RNA of a comparative example, ssRNA (NK-0035) as an RNAi negative control (NO shown in Example A5 was used.

RNA solution was prepared by dissolving 100 μg of each of the ssRNAs in 80 μl of sterile physiological saline (Nippon Kayaku Co. Ltd. hereinafter the same). On the other hand, an LPS solution was prepared by dissolving 100 μg of lipopolysaccharide (LPS) in 50 μl of sterile physiological saline.

First, 80 μl of the RNA solution was instilled in tracheae of mice. Then, 1 hour after the instillation, 50 μl of the LPS solution was instilled in the tracheae of the mice to induce lung injury.

As a negative control for the LYS, 50 μl of sterile physiological saline containing no LPS was used instead of the LPS solution. Also, as a negative control for the RNA solution, 80 μl of sterile physiological saline was used.

The administration groups are shown below. In each administration group, four to six mice were used.

Administration Group 1:
1 hour after the administration of 80 μl of the sterile physiological saline, 50 μl of the sterile physiological saline was administered.

Administration Group 2:
1 hour after the administration of 80 μl of the RNA solution (NK-0033), 50 μl of the sterile physiological saline was administered.

Administration Group 3:
1 hour after the administration of 80 μl of the RNA solution (NK-0035), 50 μl of the sterile physiological saline was administered.

Administration Group 4:
1 hour after the administration of 80 μl of the sterile physiological saline, 50 μl of the LPS solution was administered.

Administration group 5:
1 hour after the administration of the RNA solution (NK-0033), 50 μl of LPS solution was administered.

Administration Group 6:
1 hour after the administration of the RNA solution (NK-0033), 50 μl of LPS solution was administered.

(1.2) Sampling of Bronchoalveolar Lavage Fluid (BALF)

24 hours after the instillation of the LPS solution, the mice were euthanized by administering an excess of pentobarbital to their abdominal cavities, and they were used as samples for the biochemical analysis and the histological analysis. As a negative control, sterile physiological saline was used instead of the LPS solution.

Blood samples were collected by puncturing the hearts of the mice. Each blood sample was added to a test tube containing a 3.8% aqueous solution of sodium citrate. The amount (volume) of the aqueous solution of sodium citrate was set to ¹⁄₁₀ of the blood sample. A BALF sample was collected from this mixture in a manner described in Yasui et al. (Am J Respir Crit. Care Med 2001: 163: 1660-8). Then, the total number of cells in the BALF sample was measured using a Nucleo Counter (trade name, ChemoMetec).

The BALF sample was centrifuged, and the supernatant of the BALF sample was collected. The supernatant was stored at −80° C. until the biochemical analysis was conducted. Furthermore, in order to count the different kinds of cells contained in the BALF sample, the BALF sample was centrifuged using a Cytospin, and the separated cells were subjected to Giemsa staining using a May-Grunwald-Giemsa (trade name, Merck). Also, lung tissues were collected from the mice and then stained with HE.

(2) Results (2.1) Inhibition of TGF-β1 Expression in Lung

Regarding each lung sample of the mice, the expression level of the TGF-β1 gene per unit lung weight was measured using a TGF-β1 Quantikine Colorimetric Sandwich ELISA (trade name, R&D Systems).

Figure 9:
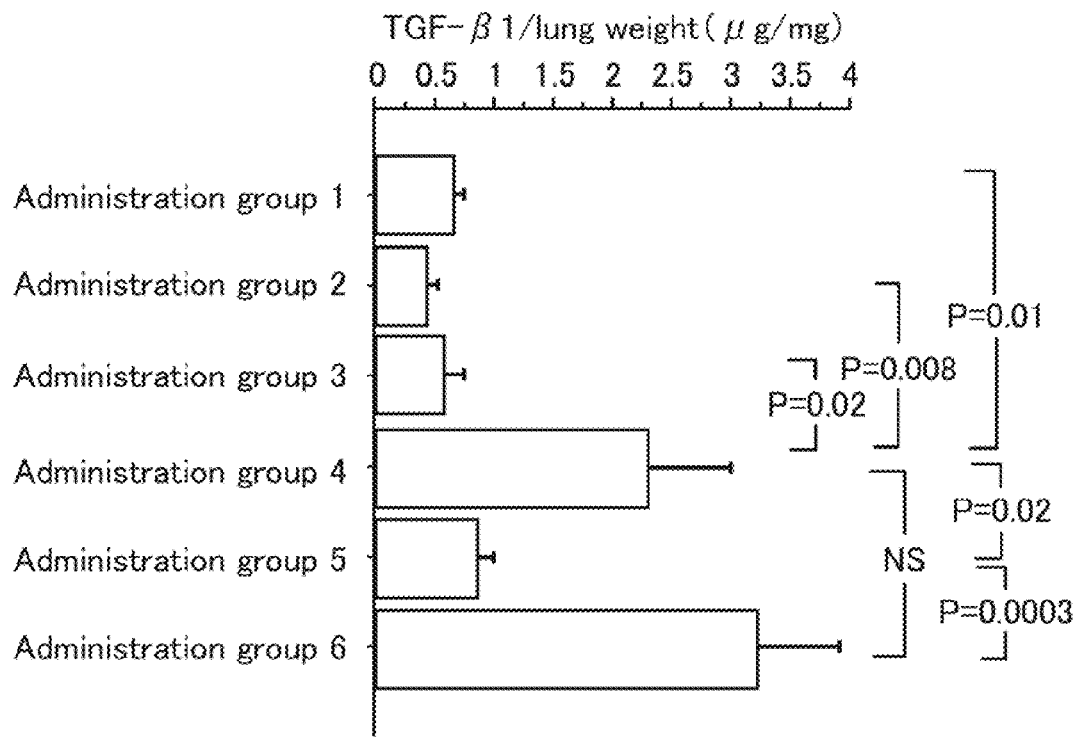
FIG. 9 is a graph showing the expression level of TGF-β1 per unit lung weight in each administration group in still another example of the present invention.

The results thereof are shown in FIG. 9. FIG. 9 is a graph showing the expression level of TGF-β1 per unit lung weight in each administration group. In the administration group 4 (LPS (+)/RNA (−)), the expression level of TGF-β1 was increased as a result of the LPS treatment, as compared with that in the administration group 1 (LPS (−)/RNA (−)). In the administration group 5 (LPS (+)/NK-0033 (+)) of the example, an increase in the expression level of TGF-β1 was inhibited as compared with that in the administration group 4 (LPS (+)/RNA (−)). This inhibitory effect was not observed in the administration group 6 (LPS (+)/negative control NK-0035 (+)). These results demonstrate that NK-0033 of the example can effectively inhibit the expression of the TGF-β1 gene.

(2.2) Inhibitory Effect on Acute Lung Injury

Inflammation in acute lung injury is caused by the infiltration of cells such as neutrophils into lungs. Thus, drugs that inhibit the infiltration of cells such as neutrophils into lungs can be used as therapeutic agents for inflammation in acute lung injury. Thus, the pharmacological effect of the ssRNA of the present invention was examined by counting the number of cells in bronchoalveolar lavage fluid (BALF) as an indicator of the number of cells having infiltrated to the lungs.

Figure 10:
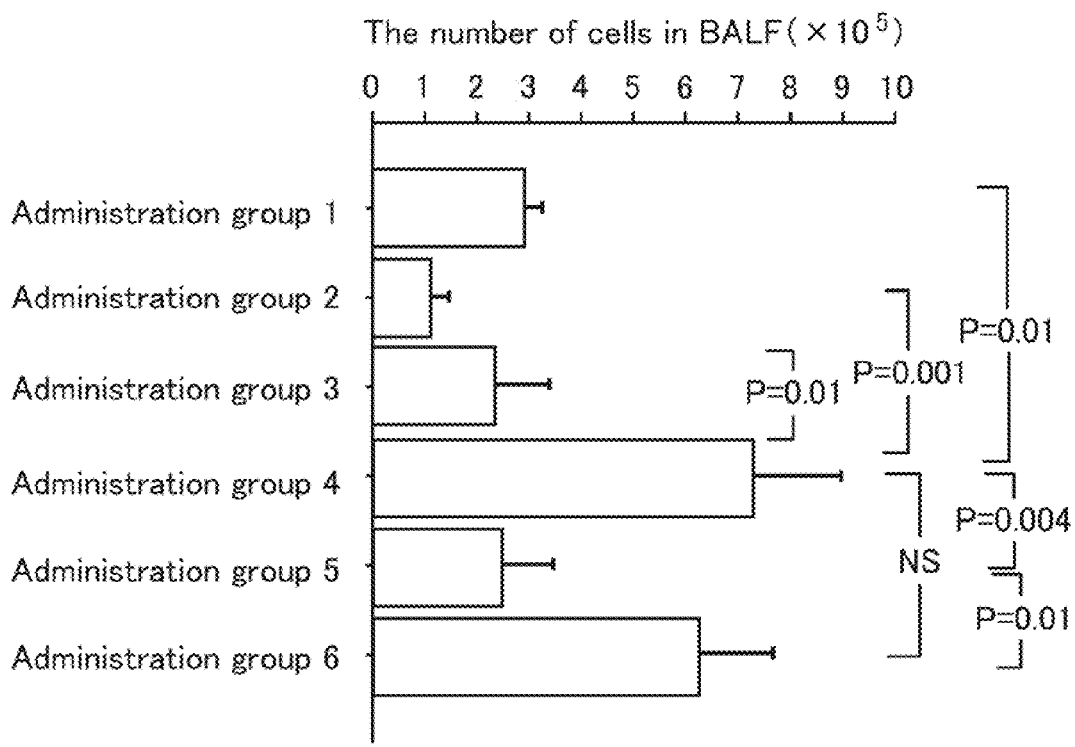
FIG. 10 is a graph showing the number of cells in a BALF sample in each administration group in the example of the present invention.

The results of counting the number of cells in the BALF sample are shown in FIG. 10. FIG. 10 is a graph showing the number of cells in the BALF sample in each administration group. In the administration group 4 (LPS (+)/RNA (−)), the number of cells in the BALF sample increased as a result of the LPS treatment, as compared with that in the administration group 1 (LPS (−)/RNA (−)). This indicates that LPS induced an inflammatory action, whereby the cells were allowed to infiltrate into the lungs. In the administration group 5 LPS (+)/NK-0033 (+) of the example, an increase in the number of cells was inhibited as compared with that in the administration group 4 (LPS (+)/INA (−)). This indicates that inflammation in acute lung injury was inhibited by NK-0033. This inhibitory effect was not observed in the administration group 6 (LPS (+)/negative control NK-0035 (+)). These results demonstrate that NK-0033 of the example can inhibit inflammation in acute lung injury effectively.

Figure 11:
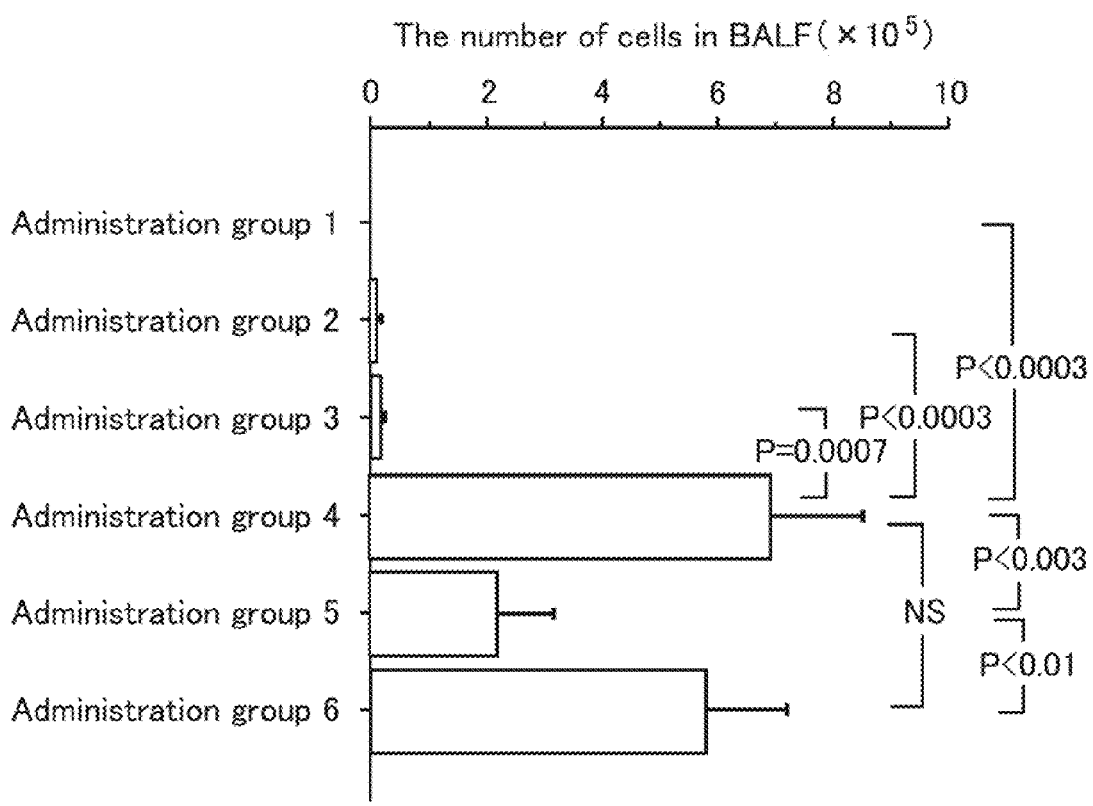
FIG. 11 is a graph showing the number of neutrophils in a BALF sample in each administration group in the example of the present invention.

The results of measuring the number of neutrophils in the BALE sample are shown in FIG. 11. FIG. 11 is a graph showing the number of neutrophils in the BALF sample in each administration group. In the administration group 4 (LPS (+)/RNA (−)), the number of neutrophils in the BALF sample increased as a result of the LPS treatment, as compared with that in the administration group 1 (LPS (−)/RNA (−)). This indicates that LPS induced an inflammatory action, whereby the neutrophils were allowed to infiltrate into the lungs. In the administration group 5 (LPS (+)/NK-0033 (+)) of the example, an increase in the number of neutrophils in the BALF sample was inhibited as compared with that in the administration group 4 (LPS (+)/ssRNA (−)). This indicates that inflammation in acute lung injury was inhibited by NK-0033. This inhibitory effect was not observed in the administration group 6 (LPS (+)/negative control NK-0035 (+)). These results demonstrate that NK-0033 of the example can inhibit inflammation in acute lung injury effectively.

(2.3) Histological Observation: Giemsa Staining

Figure 12A:
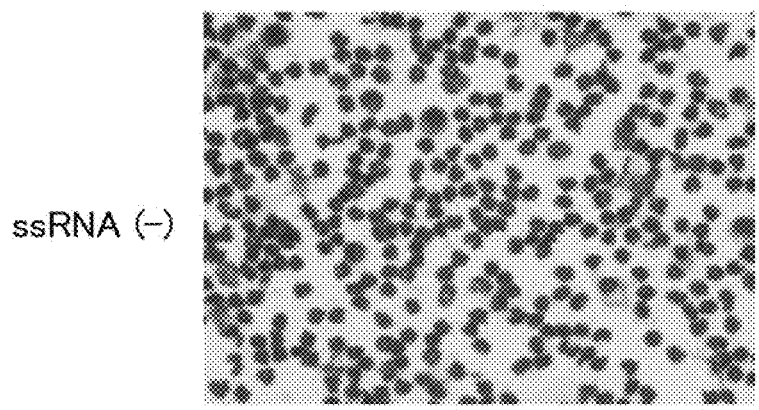
FIG. 12A shows the result obtained regarding the administration group 4 (LPS (+)/RNA (−)).
Figure 12B:
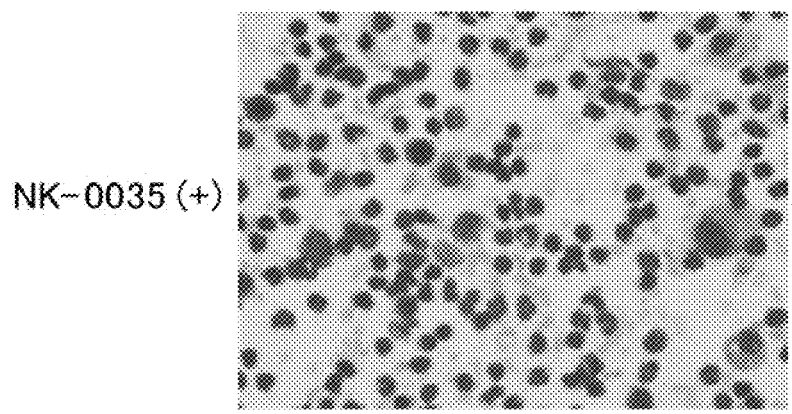
FIG. 12B shows the result obtained regarding the administration group 6 (LPS(+)/negative control NK-0035 (+)).
Figure 12C:
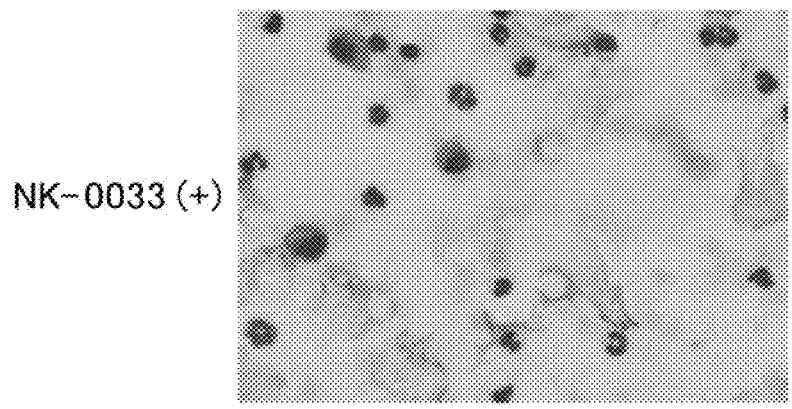
FIG. 12C shows the result obtained regarding the administration group 5 (LPS (+)/NK-0033 (+)).

The results of the Giemsa staining are shown in FIG. 12. FIG. 12 show photographs (×100) each showing the result of the Giemsa staining of the cells in the BALF sample. FIG. 12A shows the result obtained regarding the administration group 4 (LPS (+)/RNA (−)). FIG. 12B shows the result obtained regarding the administration group 6 (LPS (+)/negative control NK-0035 (+)). FIG. 12C shows the result obtained regarding the administration group 5 (LPS (+)/NK-0033 (+)).

As can be seen from FIG. 12, in the administration group 5 (FIG. 12C: LPS (+)/NK-0033 (+)) of the example, the number of the cells having infiltrated into the lungs was markedly lower than those in the administration group 4 (FIG. 12A: LPS (+)/RNA (−)) and the administration group 6 (FIG. 12B: LPS (+)/negative control NK-0035 (+)). The results of this histological observation agree with the results of counting the number of cells in the BALF sample described above.

(2.4) Histological Observation: HE Staining

Figure 13A:
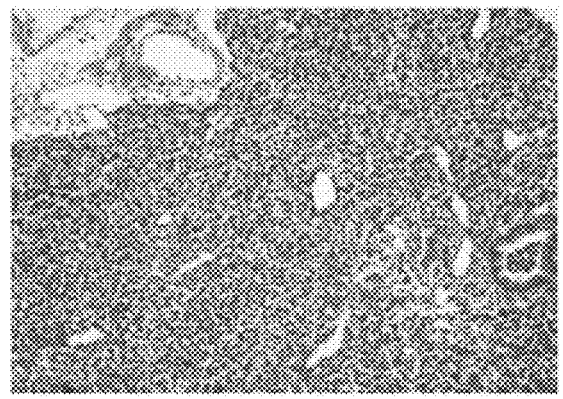
FIG. 13A shows the result obtained regarding the administration group 4 (LPS (+)/RNA (−)).
Figure 13B:
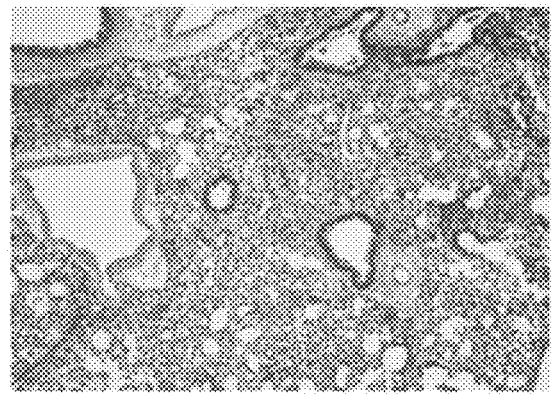
FIG. 13B shows the result obtained regarding the administration group 6 (LPS (+)/negative control NK-0035 (+)).
Figure 13C:
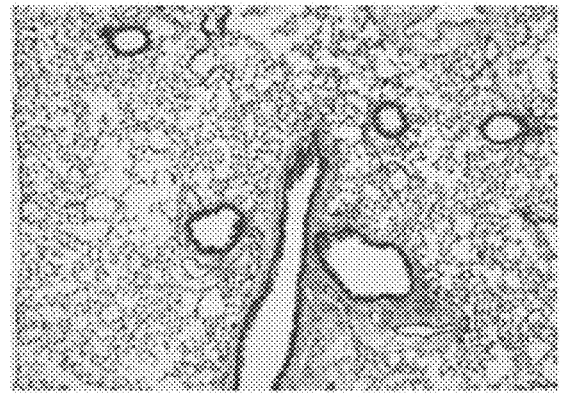
FIG. 13C shows the result obtained regarding the administration group 5 (LPS (+)/NK-0033 (+)).

The results of the HE staining are shown in FIG. 13. FIG. 13 show photographs (×10) each showing the result of the HE staining of the lung tissue. FIG. 13A shows the result obtained regarding the administration group 4 (LPS (+)/RNA (−)). FIG. 13B shows the result obtained regarding the administration group 6 (LPS (+)/negative control NK-0035 (+)). FIG. 13C shows the result obtained regarding the administration group 5 (LPS (+)/NK-0033 (+)) From FIG. 13, it was found that infiltration of the cells such as neutrophils into the vicinity of blood vessels, alveolar spaces, alveolar walls, and the vicinity of bronchial tubes was decreased and the damages to the lung tissues were decreased.

Example A7

Evaluation of Side Effect Using Interferon Induction as Indicator

It is known that conventional RNAi agents bring about a side effect that interferon is induced in a sequence-independent manner, and this side effect is perceived as a problem. Thus, regarding the ssRNA of the present invention, interferon induction as the side effect was evaluated.

(1) Materials and Method

The ssRNA was administered to mice with acute lung injury in the same manner and under the same conditions as in Example A6. Then, 24 hours after the instillation of the LPS solution or sterile physiological saline (negative control for LPS), the mice were euthanized, and their lung tissues were collected.

TABLE 4

| Administration group | RNA | LPS |
|---|---|---|
| 1 | — | − |
| 9 | Ex: NK-0033 | − |
| 4 | — | + |
| 5 | Ex: NK-0033 | + |

EX: RNA of the example

In order to measure the expression level of each gene, RNA was isolated from each of the lung tissues using TRIZOL (trade name, Invitrogen). Next, cDNA was synthesized from the RNA using a reverse transcriptase (trade name: SuperScriptII, Invitrogen) according to the protocol supplied therewith. Then. PCR was carried out using the thus-synthesized cDNA as a template, and the expression levels of the TGF-β1 gene, IFN-α gene, and IFN-β gene were measured.

The PCR was carried out using Gold AmpliTaq (trade name, Applied Biosystem. USA) as a reagent and AB Applied Biosystem 7600 (trade name, Applied Biosystem) as a measuring instrument. The TGF-β1 gene, the IFN-α gene, and the IFN-β gene were amplified using the following primer sets, respectively.

```
Primer set for GAPDH gene
5'-CCCTTATTGACCTCAACTACATGGT-3'      (SEQ ID NO: 21)

5'-GAGGGGCCATCCACAGTCTTCTG-3'        (SEQ ID NO: 22)

Primer set for TGF-β1 gene
5'-ACTCCACGTGGAAATCAACGG-3'          (SEQ ID NO: 23)

5'-TAGTAGACGATGGGCAGTGG-3'           (SEQ ID NO: 24)

Primer set for IFN-α gene
5'-ATGGCTAGRCTCTGTGCTTCCT-3'         (SEQ ID NO: 25)

5'-AGGGCTCTCCAGAYTTCTGCTCTG-3'       (SEQ ID NO: 26)

Primer set for IFN-β gene
5'-CATCAACTATAAGCAGCTCCA-3'          (SEQ ID NO: 27)

5'-TTCAAGTGGAGAGCAGTTCAG-3           (SEQ ID NO: 28)
```

Then, each of the thus-obtained PCR products was subjected to agarose gel electrophoresis. The density analysis of the agarose gel was performed using an NIH imaging system, and the expression levels of the respective genes were measured. The expression levels of the TGF-β1 gene, IFN-α gene, and IFN-β gene were evaluated relatively with reference to the expression level of the GAPDH gene as the standard. Specifically, the measured intensity of the PCR product obtained using the primer set for the GAPDH, was set as 1, and those for the respective genes were evaluated as relative value to that for the GAPDH.

(2) Results and Consideration

Figure 14A:
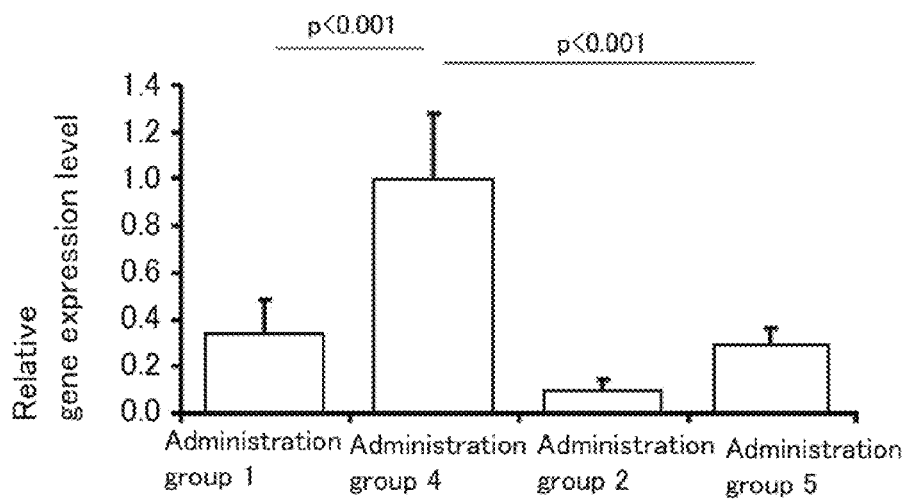
FIG. 14A shows the result of measuring the expression level of the TGF-β1 gene in still another example of the present invention.
Figure 14B:
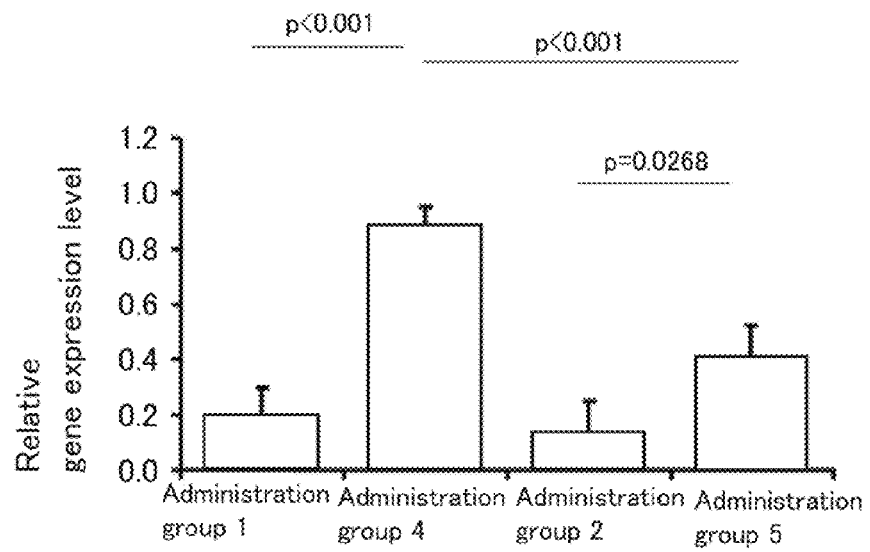
FIG. 14B shows the result of measuring the expression level of the IFN-α gene in the example of the present invention.
Figure 14C:
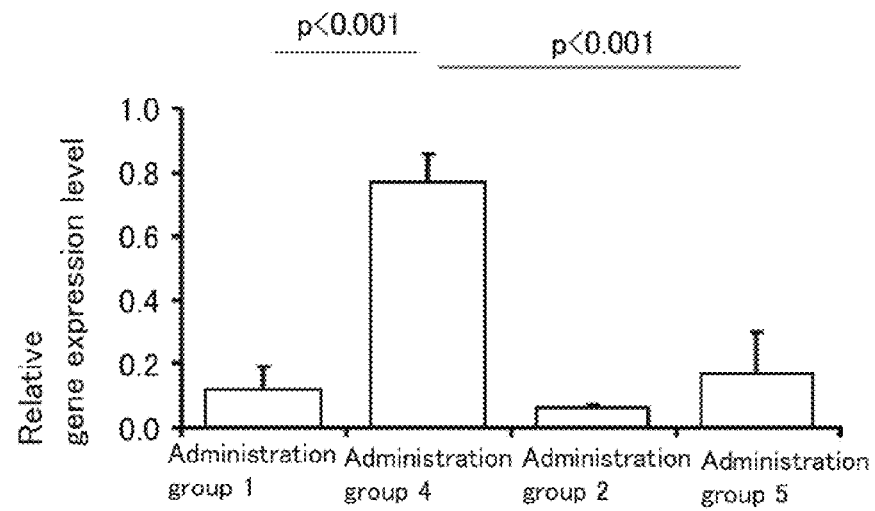
FIG. 14C shows the result of measuring the expression level of the IFN-β gene in the example of the present invention.

The results of quantitative analysis regarding the expression levels of the TGF-β1 gene, IFN-α gene, and IFN-β gene are shown in the graphs of FIGS. 14A to 14C, respectively. The administration groups are as shown below and are the same as in Example A6.

FIG. 14A shows the results of measuring the expression level of the TGF-β1 gene. As can be seen from FIG. 14A, in the administration group 5 of the example to which NK-0033 was administered, an increase in the TGF-β1 gene expression inducted by LPS was inhibited, as compared with that in the administration group 4 (RNA (−)). This result correlates with the results of measuring the expression level of TGF-β1 in Example A5, which are shown in FIG. 8.

FIG. 14B shows the results of measuring the expression level of the IFN-α gene, and FIG. 14C shows the results of measuring the expression level of the IFN-β gene. As can be seen from FIGS. 14B and 14C, when LPS was not instilled, it was found from the comparison between the administration group 1 (RNA (−)) and the administration group 2 (RNA (+)) that the expressions of the IFN-α gene and the IFN-β gene, which are both type I interferon, were not induced by the instillation of the ssRNA. Also, as can be seen from FIGS. 14B and 14C, when LPS was instilled, it was revealed from the comparison between the administration group 4 (RNA (−)) and the administration group 5 (NK-0033 (+)) that the expressions of both the IFN-α gene and the IFN-β gene were not induced by the instillation of the ssRNA.

These results contrast with the fact that the use of conventional siRNAs causes a side effect that type I interferon is induced. That is, it is demonstrated that, unexpectedly, the ssRNA of the present invention does not cause interferon induction as the side effect that has been perceived as a problem in conventional siRNAs.

Example A8

Inhibitory Effect on the TGF-β1 Gene Expression in Hepa1-6 Cells

Regarding the ssRNA of the present invention, the inhibitory effect on the TGF-β1 gene expression in vitro was examined.

(1) Materials and Method

As RNAs (Ex) of the present example, NK-0033 of Example A5 and NK-0061, NK-0055, and NK-0062 shown below were used. In the following sequences, "*" indicates an unpaired base.

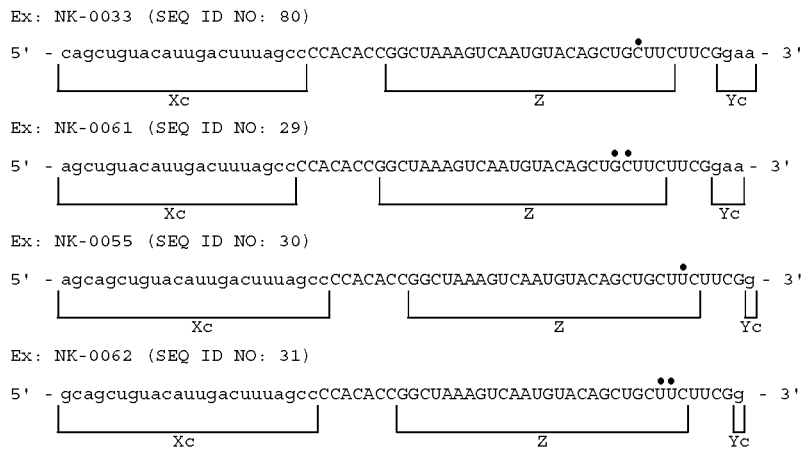

Also, as RNAs (Ex) of the present example, PK-0007, PK-0026, PK-0027, and PK-0028 shown below were used. In each of these ssRNAs, a linker region (Lx) and a linker region (Ly) were provided by linking Compound 10 (L-proline-diamide-amidite) in Scheme 3 shown in Examples B between Xc and X, and between Yc and Y, respectively.

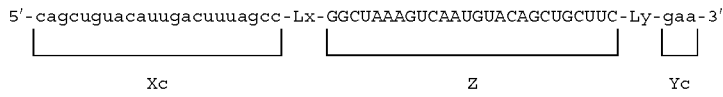

Ex: PK-0007 (SEQ ID NO: 32)

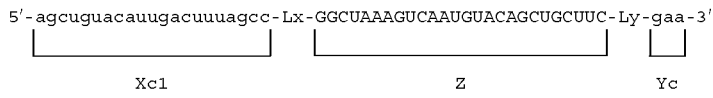

Ex: PK-0026 (SEQ ID NO: 33)

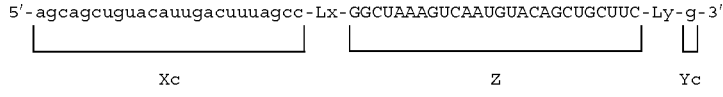

Ex: PK-0027 (SEQ ID NO: 34)

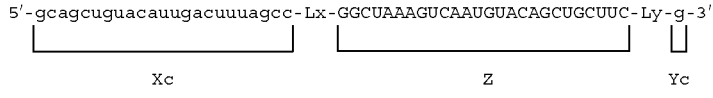

Ex: PK-0028 (SEQ ID NO: 35)

The sequences of NK-0033, NK-0061, NK-0055 and NK-0062 are the same as those of PK-0007, PK-0026, PK-0027 and PK-0028, respectively, except for the first linker (L1) and the second linker (L2). They all have a sequence that inhibits the expression of the TGF-β1 gene (SEQ ID NO: 16).

(1.2) Inhibition of Gene Expression

RNA solution was prepared by dissolving each of the RNAs that had been cryopreserved in distilled water for injection so as to achieve a concentration of 20 μmol/l. Then, transfection of the ssRNA to the Hepa1-6 cells, collection of RNA, synthesis of cDNA, PCR, and determination of the relative expression level of the TGF-β1 gene were carried out in the same manner as in Example A5, except that the above RNA solution was used. The RNA concentration at the time of the transfection was set to 1 nmol/l.

(2) Results

Figure 15:
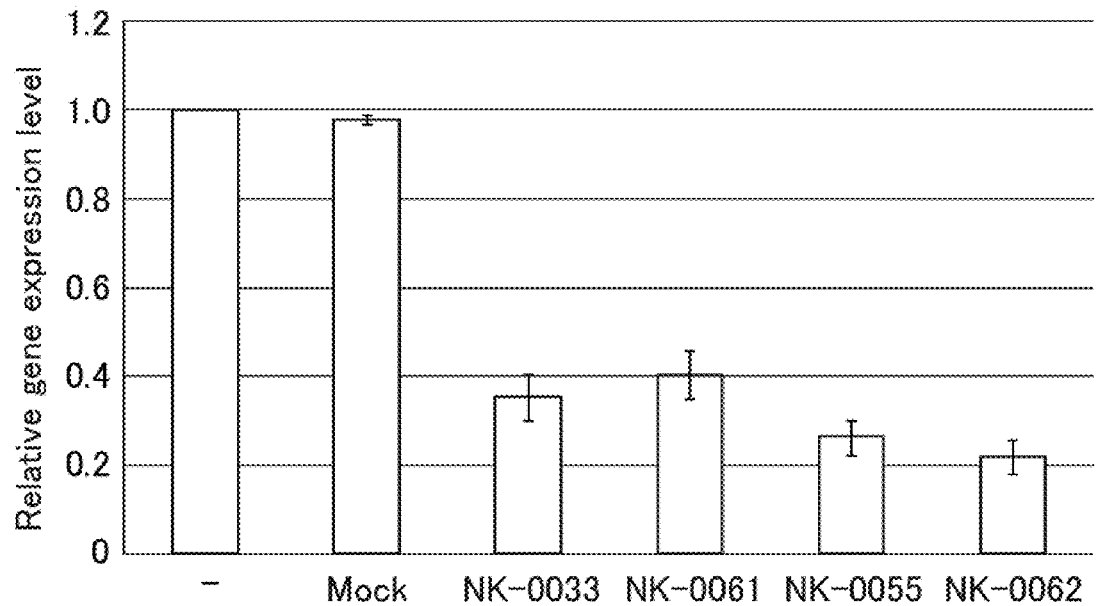
FIG. 15 is a graph showing the relative value of the expression level of the TGF-β1 gene in still another example of the present invention.
Figure 16:
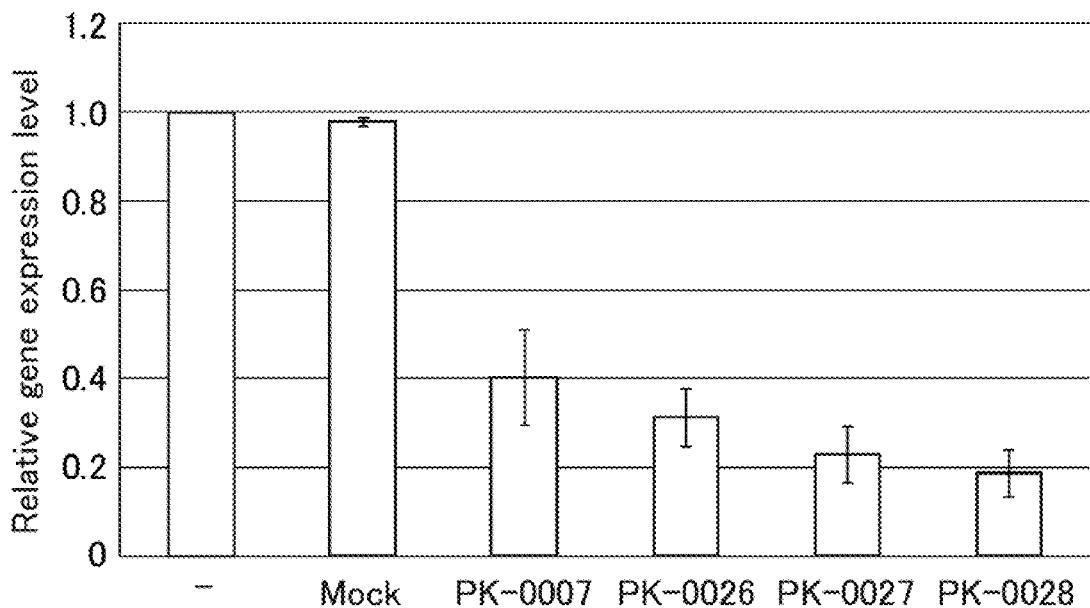
FIG. 16 is a graph showing the relative value of the expression level of the TGF-β1 gene in the example of the present invention.

The results thereof are shown in FIGS. 15 and 16. FIGS. 15 and 16 are each a graph showing the relative expression level of the TGF-β1 gene. FIG. 15 shows the results obtained when NK-0033, NK-0061, NK-0055, and NK-0062 were used, and FIG. 16 shows the results obtained when PK-0007, PK-0026, PK-0027, and PK-0028 were used. As can be seen from FIGS. 15 and 16, these ssRNAs all exhibited potent inhibitory activities.

Example A9

Inhibitory Effects on the TGF-β1 Gene Expression and Acute Lung Injury In Vivo (A9-1) Inhibitory Effect on the TGF-β1 Gene Expression In Vivo Using the ssRNA of the present invention, the effect of inhibiting TGF-β1 gene expression in vivo was examined.

(1) Materials and Method

Administration of the RNA to acute lung injury mice was carried out in the same manner as in Example A6, unless otherwise stated.

As RNAs (Ex) of the present example, PK-0007 and NK-0033 of Example A8 were used. Furthermore, as RNA of a comparative example, PK-0008 and NK-0035 as RNAi negative controls (Nc), dsRNA (NI-0030) as an RNAi positive control (Pc), and dsRNA (NI-0031) as an RNAi negative control (Nc) shown below were used. PK-0008 as the negative control has linkers Lx and Ly derived from the above-described amidite (Compound 10 in Scheme 3: L-proline-diamide-amidite), and these linkers are the same as those in PK-0007.

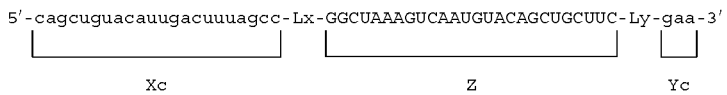

Ex: PK-0007 (SEQ ID NO: 32)

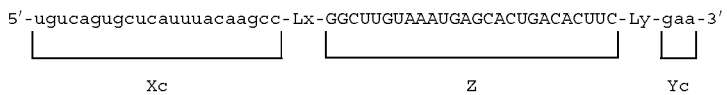

Nc: PK-0008 (SEQ ID NO: 36)

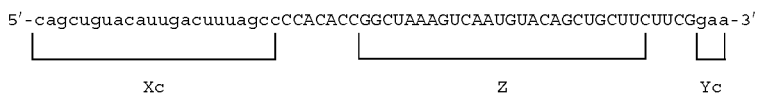

Ex: NK-0033 (SEQ ID NO: 80)

-continued

Nc: NK-0035 (SEQ ID NO: 15)

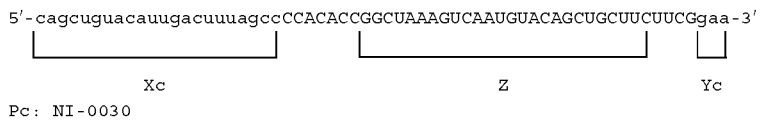

```
Pc: NI-0030
    5'-  GCAGCUGUACAUUGACUUUAG-3'(SEQ ID NO: 39)
    3'-UUCGUCGACAUGUAACUGAAA  -5'(SEQ ID NO: 40)
Nc: NI-0031
    5'-  GUGUCAGUGCUCAUUUACAAG-3'(SEQ ID NO: 41)
    3'-UUCACAGUCACGAGUAAAUGU  -5'(SEQ ID NO: 42)
```

RNA solution was prepared by dissolving 100 μg of each of the RNAs in 75 μl of sterile physiological saline. On the other hand, an LPS solution was prepared by dissolving 100 μg of lipopolysaccharide (LPS) in 50 μl of sterile physiological saline.

Administration groups are shown below. Unless otherwise stated, the administration was carried out in the same manner as in Example A6. In each administration group, four to six mice were used.

Administration Group 1:
5 minutes after the administration of 75 μl of sterile physiological saline, 50 μl of sterile physiological saline was administered.
Administration Group 2:
5 minutes after the administration of 75 μl of sterile physiological saline, 50 μl of the LPS solution was administered.
Administration Group 3:
5 minutes after the administration of 75 μl of the RNA solution (PK-0007), 50 μl of the LPS solution was administered.
Administration Group 4:
5 minutes after the administration of 75 μl of the RNA solution (PK-0008), 50 μl of the LPS solution was administered.
Administration Group 5:
5 minutes after the administration of 75 μl of the RNA solution (NK-0033), 50 μl of the LPS solution was administered.
Administration Group 6:
5 minutes after the administration of 75 μl of the RNA solution (NK-0035), 50 μl of the LPS solution was administered.
Administration Group 7:
5 minutes after the administration of 75 μl of the RNA solution (NI-0030), 50 μl of the LPS solution was administered.
Administration Group 8:
5 minutes after the administration of 50 μl of the RNA solution (NI-0031), 50 μl of the LPS solution was administered.

Then, lung samples were prepared and the expression level of TGF-β1 per unit lung weight was measured in the same manner as in Example A6.

Figure 17:
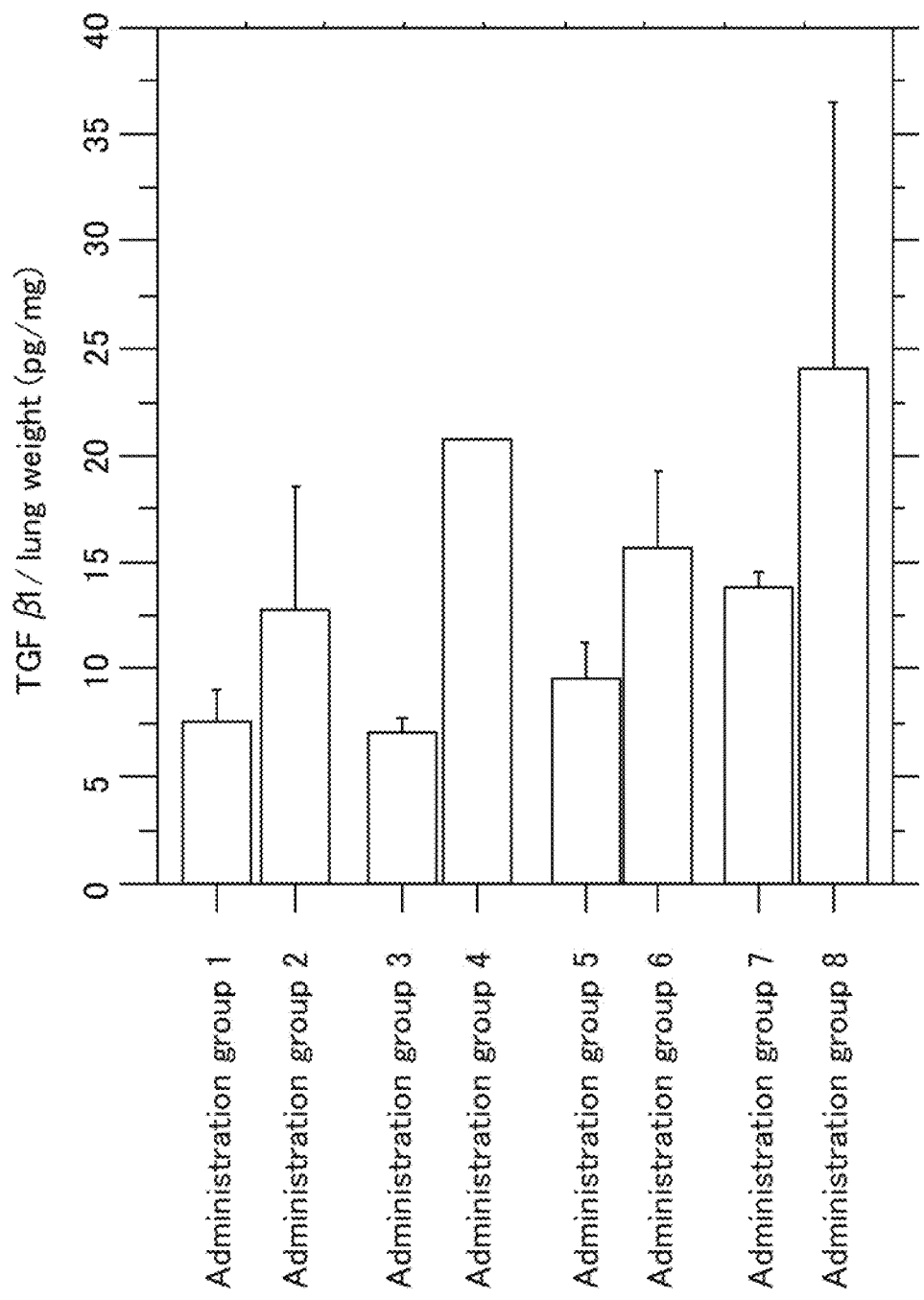
FIG. 17 is a graph showing the expression level of the TGF-β1 gene per unit lung weight in each administration group in still another example of the present invention.

The results thereof are shown in FIG. 17. FIG. 17 is a graph showing per unit lung weight in each administration group. In the administration group 3 (LPS (+)/PK-0007 (+)) and the administration group 5 (LPS (+)/NK-0033 (+)), the expression level of the TGF-β1 gene was inhibited as compared with that in the administration group 2 (LPS (+)/ssRNA (−)). It was found that these inhibitory effects were stronger than that in the administration group 7 (LPS (+)/positive control NI-0030). In particular, in the administration group 3 (LPS (+)/PK-0007 (+)), a marked inhibitory effect was observed. In the administration groups to which negative control RNAs were administered, namely, the administration group 4 (PK-0008), the administration group 6 (NK-0035), and the administration group 8 (NI-0031), no inhibitory effect, was observed.

(A9-2) Off-Target Effect In Vivo

Using the ssRNA of the present invention, the off-target effect in vivo was examined and the side effect was evaluated. As RNA of the present example, the ssRNA (PK-0007) of Example A8 was used. As RNAs of a comparative example, ssRNA (PK-0008) as an RNAi negative control (Nc), dsRNA (NI-0030) as an RNAi positive control (Pc), and dsRNA (NI-0031) as an RNAi negative control shown in Example A9-1 were used. RNA solution was prepared by dissolving 100 mg of each of the RNAs in 75 μl of sterile physiological saline.

Administration groups are shown below. In each administration group, two to four mice were used.
Administration Group 1:
75 μl of sterile physiological saline was administered.
Administration Group 2:
75 μl of the RNA solution (PK-0007) was administered.
Administration Group 3:
75 μl of the RNA solution (PK-0008) was administered.

Then, 24 hours after the administration, BALF samples were collected from the mice and supernatants of the BALF samples were obtained in the same manner as in Example M. The amount of TNF-α and the amount of IFN-β in each supernatant were measured. The amount of TNF-α was quantified using a Mouse TNF set II (trade name, Beckton Dickinson and Company) in accordance with its instructions for use. The amount of IFN-β was quantified using a ELISA plate produced using Rabbit Anti-Mouse Interferon β (trade name, PBL Interferon Source) and Biotin Labeling Kit-NH2 (trade name, Dojindo Laboratories) in accordance with their instructions for use.

Figure 18A:
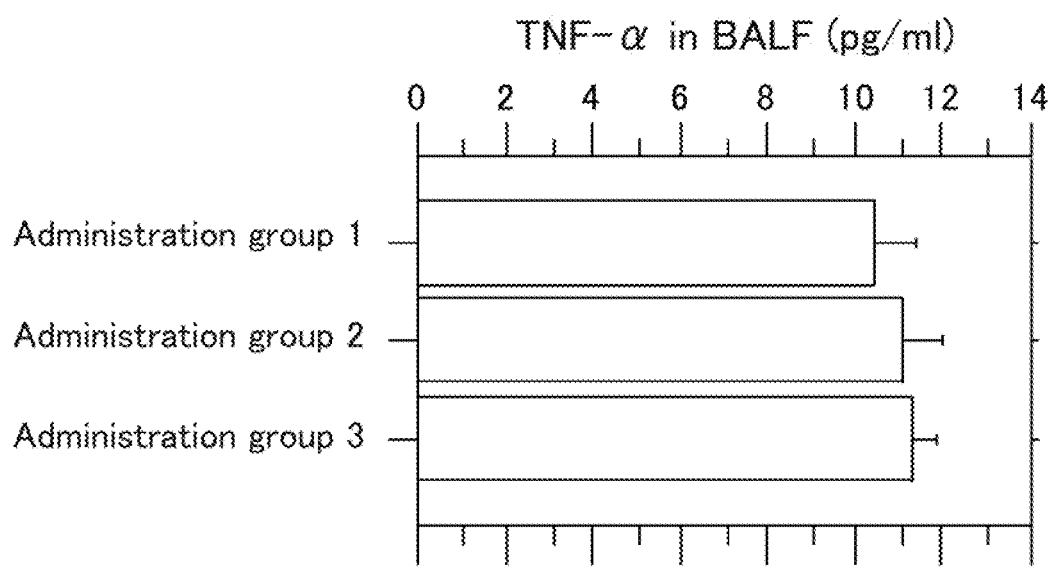
FIG. 18A is a graph showing the amount of TNF-α in a BALF sample in each administration group in the example of the present invention.
Figure 18B:
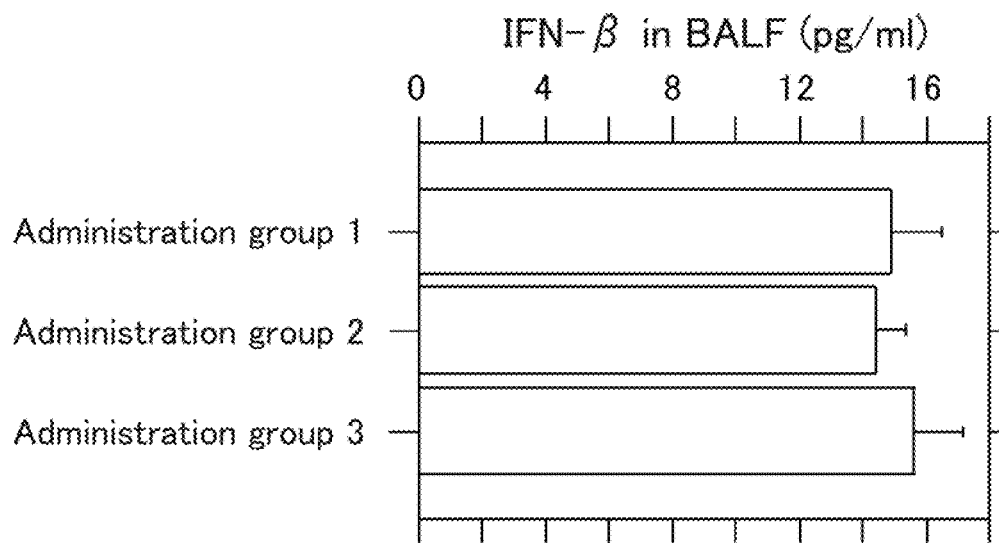
FIG. 18B is a graph showing the amount, of IFN-β in a BALF sample in each administration group in the example of the present invention.

The results thereof are shown in FIG. 18. FIG. 18A is a graph showing the amount of TNF-α in the BALF sample in each administration group, and FIG. 18B is a graph showing the amount of IFN-β in the BALF sample in each administration group. In FIGS. 18A and 18B, the horizontal axes indicate the respective amounts. In the administration group 2 (PK-0007 (+)), expressions of TNF-α and IFN-β were not caused, as compared with the administration group 1 (RNA (−)).

Example A10

Inhibitory Effect on the LAMA1 Gene Expression in 293 Cells

Using the ssRNA of the present invention, inhibition of the LAMA1 gene expression in vitro was examined.

(1) Materials and Method

As RNA (Ex) of the present example, NK-0043 and NK-0064 shown below were used. In the following sequences, "*" indicates an unpaired base (hereinafter the same).

Ex: NK-0043 (SEQ ID NO: 43)

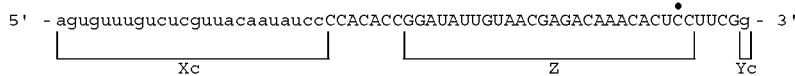

Ex: NK-0064 (SEQ ID NO: 44)

Transfection to 293 cells was carried out in the same manner as in Example A4, except that each of the above RNAs was used, and the cells were cultured for 48 hours. The RNA concentration at the time of the transfection was set to 10 nmol/l. Then, collection of RNA, synthesis of cDNA, and PCR were carried out in the same manner as in Example A2, except that a primer set for the LAMA1 gene shown below were used, and the expression level of the LAMA1 gene and that of the β-actin gene as an internal standard were measured. The expression level of the LAMA1 gene was corrected with reference to that of the β-actin gene as the internal standard.

```
Primer set for LAMA1 gene
5'-AAAGCTGCCAATGCCCCTCGACC-3'    (SEQ ID NO: 45)

5'-TAGGTGGGTGGCCCTCGTCTTG-3'     (SEQ ID NO: 46)
```

Figure 19:
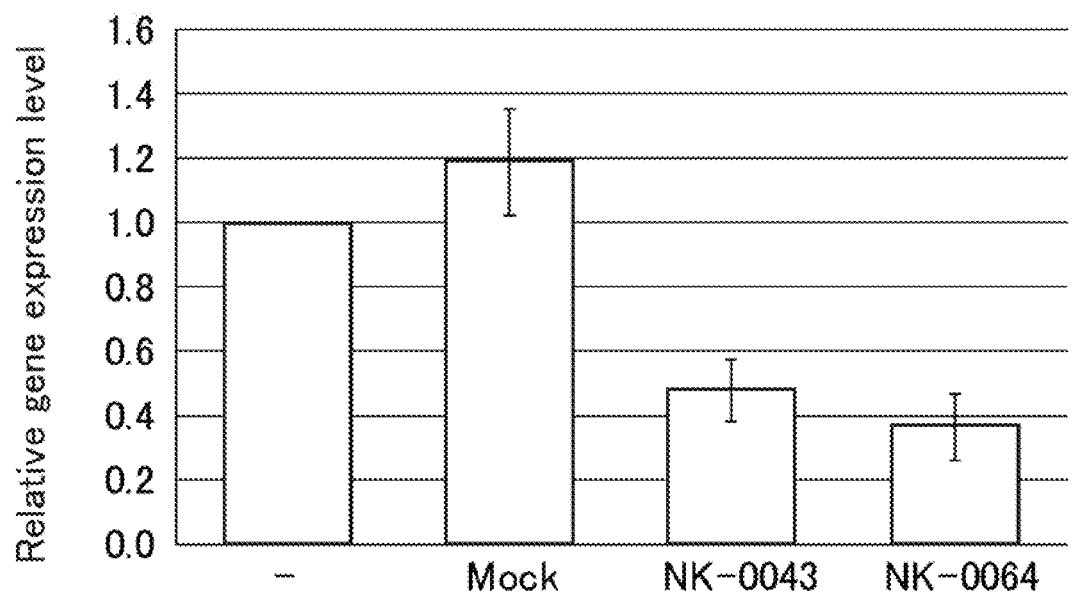
FIG. 19 is a graph showing the relative expression level of the LAMA1 gene in 293 cells in still another example of the present invention.

Regarding each of the control 1 (−) and the control 2 (mock), the expression level was measured in the same manner as in Example A2. The corrected expression level of the LAMA1 gene in the control (−) was set as 1, and that in the cells transfected with each RNA was presented as the relative value to that in the control (2) Results The results thereof are shown in FIG. 19. FIG. 19 is a graph showing the relative expression level of the LAMA1 gene in the 293 cells. As can be seen from FIG. 19, it was found that NK-0043 and NK-0064 of the example each exhibit a potent inhibitory activity.

Example A11

Inhibitory Effect on the LMNA Gene Expression in A549 Cells

Using the ssRNA of the present invention, inhibition of LMNA gene expression in vitro by the RNA interference effect was examined.

(1) Materials and Method

As RNAs (Ex) of the present example, NK-0063 and NK-0066 shown below were used. In the following sequences, "*" indicates an unpaired base.

Ex: NK-0063 (SEQ ID NO: 47)

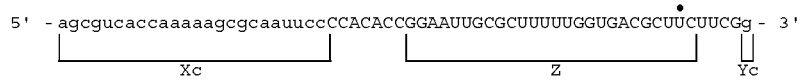

Ex: NK-0066 (SEQ ID NO: 48)

Transfection to A549 cells was carried out in the same manner as in Example A4, except that each of the above RNAs was used, and the cells were cultured for 48 hours. The RNA concentration at the time of the transfection was set to 3 nmol/l. Then, collection of RNA, synthesis of cDNA, and PCR were carried out in the same manner as in Example A2, except that a primer set for the LMNA gene shown below was used, and the expression level of the LMNA gene and that of the β-actin gene as an internal standard were measured. The expression level of the LMNA gene was corrected with reference to that of the β-actin gene as the internal standard.

```
Primer set for LMNA gene
5'-CTGGACATCAAGCTGGCCCTGGAC-3'   (SEQ ID NO: 49)

5'-CACCAGCTTGCGCATGGCCACTTC-3'   (SEQ ID NO: 50)
```

Regarding each of the control 1 (−) and the control 2 (mock), the expression level also was measured in the same manner as in Example A2. The corrected expression level of the LMNA gene in the control (−) was set as 1, and that in the cells transfected with each RNA was presented as the relative value to that in the control.

(2) Results

Figure 20:
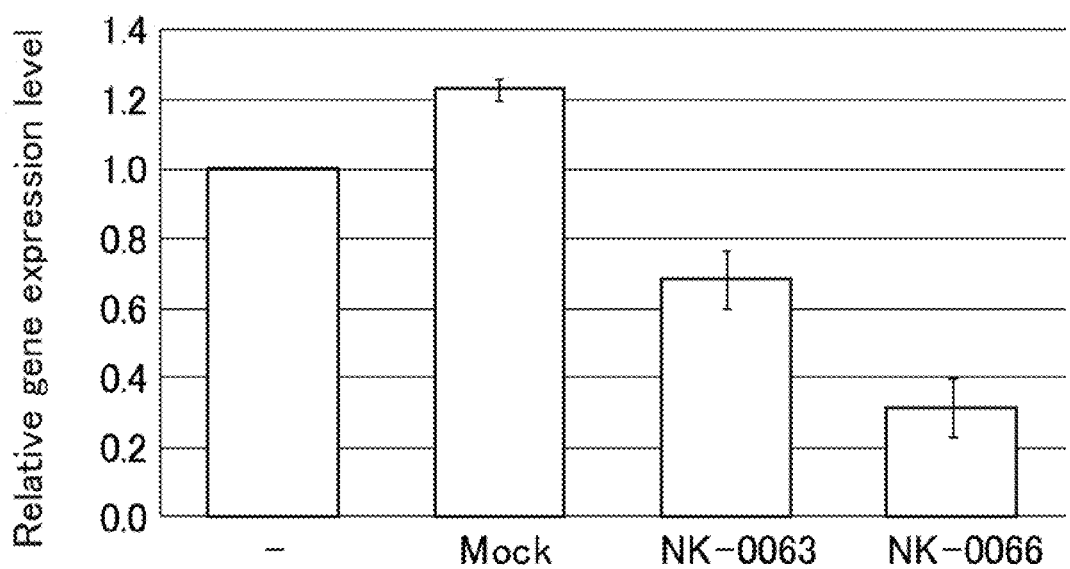
FIG. 20 is a graph showing the relative expression level of the LAMA gene in A549 cells in still another example of the present invention.

The results thereof are shown in FIG. 20. FIG. 20 is a graph showing the relative expression level of the LMNA gene in the A549 cells. As can be seen from FIG. 20, it was found that NK-0063 and NK-0066 of the example each exhibit a potent inhibitory activity.

Example A12

Lengths of Xc and Yc

Regarding the ssRNA of the present invention, the length of the 5' side region (Xc) complementary to the inner 5' side region (X) and the length of the 3' side region (Yc) complementary to the inner 3' side region (Y) were changed, and inhibition of the GAPDH gene expression in vitro was examined.

(1) Materials and Method

As RNAs of the present example, ssRNAs shown in FIG. 21 were used. In FIG. 21, the numbers on the right indicate sequence identification numbers. In FIG. 21, from the 5' side, a region indicated with underlined lowercase letters is the region (Xc); a region indicated with underlined capital letters is the inner region (Z); and a region indicated with underlined lowercase letters is the region (Yc). A region between Xc and Z is a linker region (Lx), and a region between Z and Yc is a linker region (Ly). Also, "Xc/Yc" indicates the ratio between the base length (Xc) of the region (Xc) and the base length (Yc) of the region (Yc). In FIG. 21, "*" indicates an unpaired base.

In each of the ssRNAs, the base length of the inner region (Z) was set to 26, the base length of the linker region (Lx) was set to 7, and the base length of the linker region (Ly) was set to 4. In NE-0036 and NK-0040, the total number of the bases (Xc+Yc) in the regions (Xc) and (Yc) was set to 26. In the ssRNAs other than NK-0036 and NK-0040, the total number of the bases (Xc+Yc) in the regions (Xc) and (Yc) was set to 25. Then, under these conditions, the base lengths of the regions (Xc) and (Yc) were changed. As a result. NK-0036 and NK-0040 became the molecules without unpaired bases. Furthermore, each of the ssRNAs other than NK-0036 and NK-0040 became the molecule in which the inner region (Z) includes only one unpaired base that does not form a double strand and the position of the unpaired base in the inner region (Z) was shifted from the 3' side to the 5' side.

Transfection into the HCT116 cells, culture, collection of RNA, synthesis of cDNA, and PCR were carried out in the same manner as in Example A2, except that each of the above RNAs wad used, and the relative expression level of the GAPDH gene was determined. The RNA concentration at the time of the transfection was set to 10 nmol/l.

(2) Results and Consideration

Figure 22:
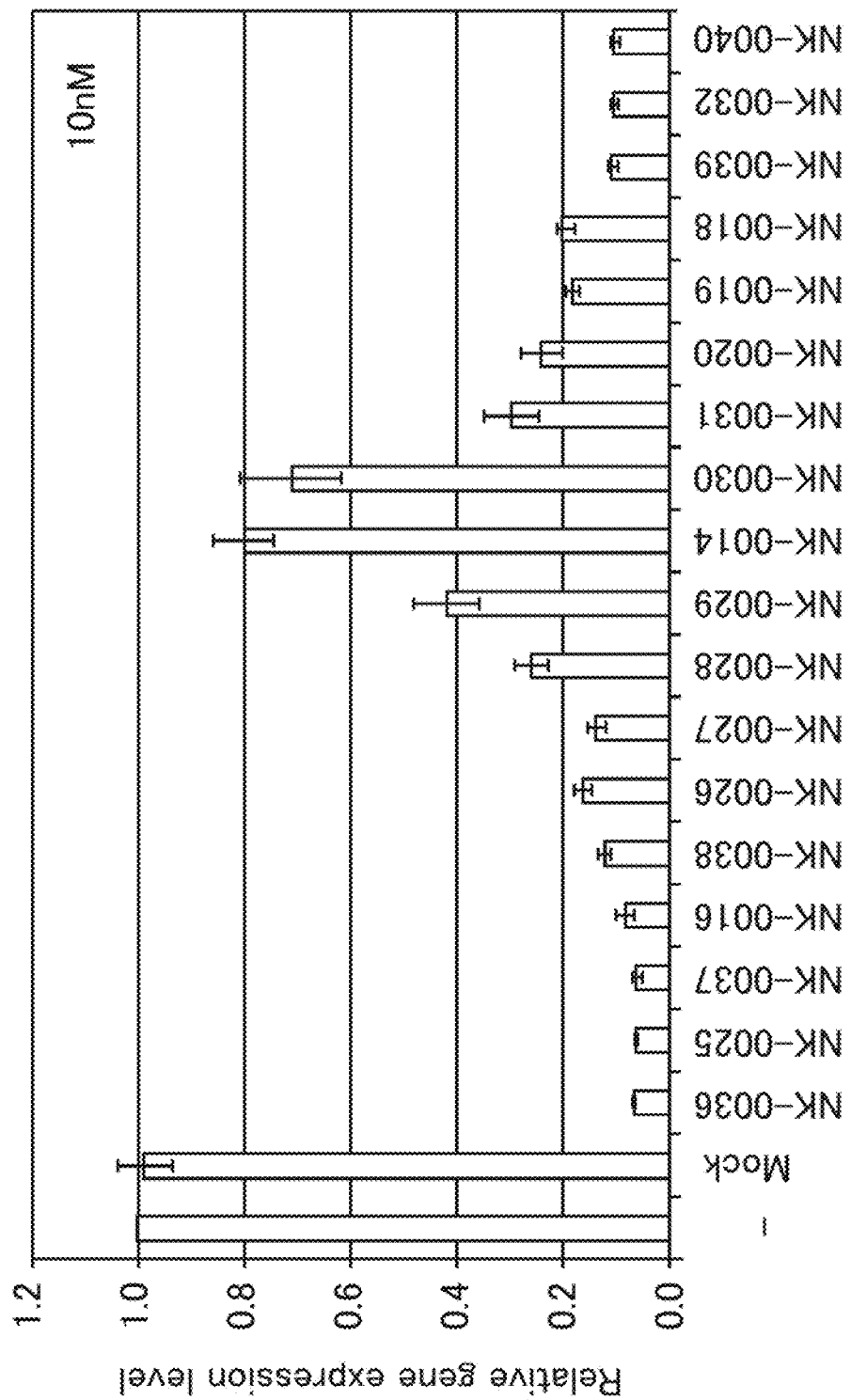
FIG. 22 is a graph showing the relative expression level of the GAPDH gene in the example of the present invention.

The results thereof are shown in FIG. 22. FIG. 22 is a graph showing the relative expression level of the GAPDH gene when each of the RNAs was used at the final concentration of 10 nmol/l. As can be seen from FIG. 22, it was found that all the ssRNAs with the varied lengths of the 5' side region (Xc) and the 3' side region (Yc) inhibited the expression of the GAPDH gene.

In particular, it was found that, as the difference between the base length of the region (Xc) and the base length of the region (Yc) became greater, the expression level of the gene decreased relatively, i.e., the inhibitory activity increased. That is, it was found that, by setting the position of the unpaired base in the inner region (Z) so as to be closer to the 5' side or the 3' side with respect to the middle of the inner region, it is possible to improve the inhibitory activity.

In Example A2, it was found that NK-0016 has a very potent inhibitory activity. In the present example, it was found that the inhibitory activities of NK-0025 and NK-0037 were even superior to that of NK-0016.

As to the position of the unpaired base, the same effect as in the present example also was obtained in the examples in which the different genes were examined, e.g., Example A8 (TGF-β1 gene), Example A10 (LAMA1 gene), and Example All (LANA gene).

That is, in Example A8, as shown in the above sequences, NK-0033 and NK-0055 both have a single unpaired base. In NK-0033, the unpaired base is the 4th base from the 3' end of the inner region (Z). In NK-0055, the unpaired base is the 2nd base from the 3' end of the inner region (Z). Then, as can be seen from FIG. 15 described above, NK-0055 having the unpaired base at a position closer to the 3' end exhibited a higher inhibitory activity. The same result was obtained when comparing NK-0061 and NK-0062 each having two unpaired bases. Also, in Examples A9 and A10, the position of the unpaired base was changed under the same conditions as in Example A8. As a result, similarly, the ssRNA having the unpaired base at a position closer to the 3' end exhibited a higher inhibitory activity.

Also from these results, it is clear that the ssRNA of the present invention exhibits a similar behavior regardless of the kind of a target gene and an expression inhibitory sequence for the target gene. Thus, it can be said that the ssRNA of the present invention is a tool that is applicable regardless of the kind of the target gene.

Example A13

Lengths of X, Xc, Y, and Yc

Regarding the ssRNA of the present invention, the lengths of the inner 5' side region (X), the 5' side region (Xc), the inner 3' side region (Y), and the 3' side region (Yc) were changed, and inhibition of the GAPDH gene expression in vitro was examined.

(1) Materials and Method

As RNAs of the present example, ssRNAs shown in FIG. 23 were used. In FIG. 23, the numbers on the right indicate sequence identification numbers. In FIG. 23, from the 5' side, a region indicated with underlined lowercase letters is the region (Xc); a region indicated with underlined capital letters is the inner region (Z); and a region indicated with underlined lower-case letters is the region (Yc). Also, "Xc+Yc/X+Y" indicates the ratio between the total base length of the regions (Xc) and (Yc) and the total base length of the regions (X) and (Y). In FIG. 23, "*" indicates an unpaired base.

In each of the ssRNAs, the base length of the linker region (Lx) was set to 7, the base length of the linker region (Ly) was set to 4, the base length of the region (Yc) was set to 1, and the 2nd base from the 3' end of the inner region (Z) was set to be an unpaired base. Then, the base length of the inner region (Z) and the base length of the region (Xc) were changed.

Unless otherwise stated, transfection of each of the RNAs into HCT116 cells, culture, collection of RNA, synthesis of cDNA, and PCR were carried out in the same manner as in Example A2, and the expression level of the GAPDH gene was measured. The transfection was carried out by setting the composition per well as follows. In the following composition, (B) is Opti-MEM (trade name, Invitrogen), (C) is the RNA solution of 20 µmol/l, and they were added so that the total amount thereof would be 98.5 µl. The final concentration of the RNA in the well was set to 1 mmol/l. Correction with an internal standard and calculation of a relative value of the expression level also were carried out in the same manner as in Example A2.

TABLE 5

| (Composition per well: µl) | |
|---|---|
| Medium | 400 |
| (A) Lipofectamine 2000 | 1.5 |
| (B) + (C) | 98.5 |
| Total | 500 |

(2) Results and Consideration

Figure 24:
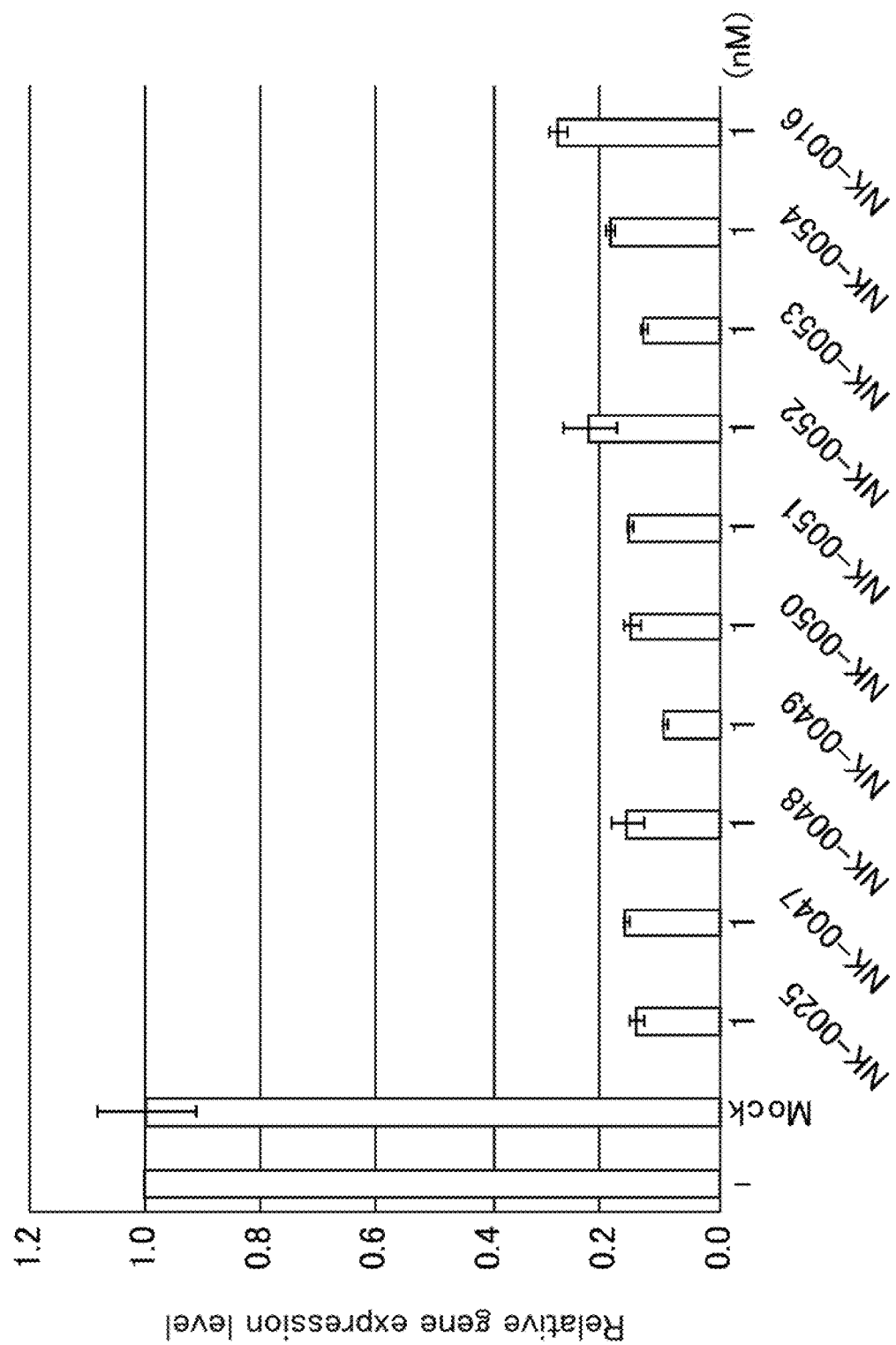
FIG. 24 is a graph showing the relative expression level of the GAPDH gene in the example of the present invention.

The results thereof are shown in FIG. 24. FIG. 24 is a graph showing the relative expression level of the GAPDH gene when each of the RNAs was used at the final concentration of 1 nmol/l. As can be seen from FIG. 24, it was found that all the ssRNAs with the varied lengths of the regions (X), (Xc), (Y), and (Yc) inhibited the expression of the GAPDH gene. In Example A2, it was found that NK-001.6 has a very potent inhibitory activity. In the present example, it was found that the inhibitory activities of all the ssRNAs excluding NK-0016 were superior even to that of NK-0016.

Example A14

Length of Xc

Regarding the ssRNA of the present invention, the length of the 5' side region (Xc) complementary to the inner 5' side region (X) was changed, and inhibition of the GAPDH gene expression in vitro was examined.

(1) Materials and Method

As RNAs of the present example, ssRNAs shown in FIG. 25 were used. In FIG. 25, from the 5' side, a region indicated with underlined lower-case letters is the region (Xc); a region indicated with underlined capital letters is the inner 5' side region (X); and a region indicated with underlined lower-case letters is the region (Yc). Also, "Xc/X" indicates the ratio between the base length (Xc) of the region (Xc) and the base length (X) of the region (X). In FIG. 25. "*" indicates an unpaired base. The sequences of the following RNAs are shown in SEQ ID NOs: 74 to 76.

In each of the ssRNAs, the base length of the inner region (Z) was set to 26: the base length of the region (X) was set to 25, the base length of the region (Y) was set to 1, the base length of the region (Yc) was set to 1, the base length of the linker region (Lx) was set to 7, and the base length of the linker region (Ly) was set to 4. Then, under these conditions, the base length of the region (Xc) was changed. Thus, in each of the ssRNAs, the presence or absence of an unpaired base that does not form a double strand and the number of such unpaired bases were changed. NK-0001 has no unpaired base.

Transfection into HCT116 cells, culture, collection of RNA, synthesis of cDNA, and PCR were carried out in the same manner as in Example A13, except that each of the above RNAs was used, and the expression level of the GAPDH gene was measured. Correction with an internal standard, and calculation of a relative value of the expression level also were carried out in the same manner as in Example A13.

(2) Results and Consideration

The results thereof are shown in FIG. 26. FIG. 26 is a graph showing the relative expression level of the GAPDH gene when each of the RNAs was used at the final concentration of 1 nmol/l. As can be seen from FIG. 26, it was found that all the ssRNAs with the varied lengths of the 5' side region (Xc) inhibited the expression of the GAPDH gene. In particular, when the ssRNAs have an unpaired base(s), it is considered that the inhibitory activity is improved as the number of the unpaired bases becomes lower. In Example A2, it was found that NK-0016 has a very potent inhibitory activity. In the present example, it was found that the ssRNAs used in the present example, which are different from NK-0016, all exhibited inhibitory activities superior even to that of NK-0016.

As to the number of the unpaired bases, the same effect as in the present example also was obtained in Example A8 in which the examined gene (TGF-β1 gene) was different from the one in the present example. That is, in Example A8, as shown in the above sequences, NK-0033 has one unpaired base, and NK-0061 has two unpaired bases. Then, as can be seen from FIG. 15 described above, NK-0033 having a lower number of unpaired bases exhibited a higher inhibitory activity. Furthermore, NK-0055 and NK-0062 in which the positions of the unpaired bases were changed so as to be closer to the 3' side of the inner region (Z) as compared to those in NK-0033 and NK-0061 exhibited a high inhibitory activity, as described in Example A12. Also from these results, it is clear that the ssRNA of the present invention exhibits a similar behavior regardless of the kind of a target gene and the kind of an expression inhibitory sequence for the target gene. Thus, it can be said that the ssRNA of the present invention is a tool that is applicable regardless of the kind of the target gene.

Example A15

Interchangeability of Linkers

Regarding the ssRNA of the present invention, the linker region (Lx) between the inner 5' side region (X) and the 5' side region (Xc) and the linker region (Ly) between the inner 3' side region (Y) and the 3' side region (Yc) were changed, and inhibition of the GAPDH gene expression in vitro was examined.

(1) Materials and Method

As RNAs of the present example, ssRNAs shown in FIG. 27 were used. In FIG. 27, from the 5' side, a region indicated with underlined lower-case letters is the 5' side region (Xc), a region indicated with underlined capital letters is the inner region (Z), and a region indicated with underlined lower-case letters is the 3' side region (Yc). The sequence between X and Xc is the linker region (Lx), and the sequence between Y and Yc is the linker region (Ly). Furthermore, regarding each of the RNAs, the ratio (Lx/Ly) between the base length (Lx) of the linker region (Lx) and the base length (Ly) of the linker region (Ly) is shown. In FIG. 27, "*" indicates an unpaired base.

Transfection into HCT116 cells, culture, collection of RNA, synthesis of cDNA, and KR were carried out in the same manner as in Example A13, except that each of the above RNAs was used, and the expression level of the GAPDH gene was measured. Correction with an internal standard, and calculation of a relative value of the expression level also were carried out in the same manner as in Example A13.

(2) Results and Consideration

Figure 28:
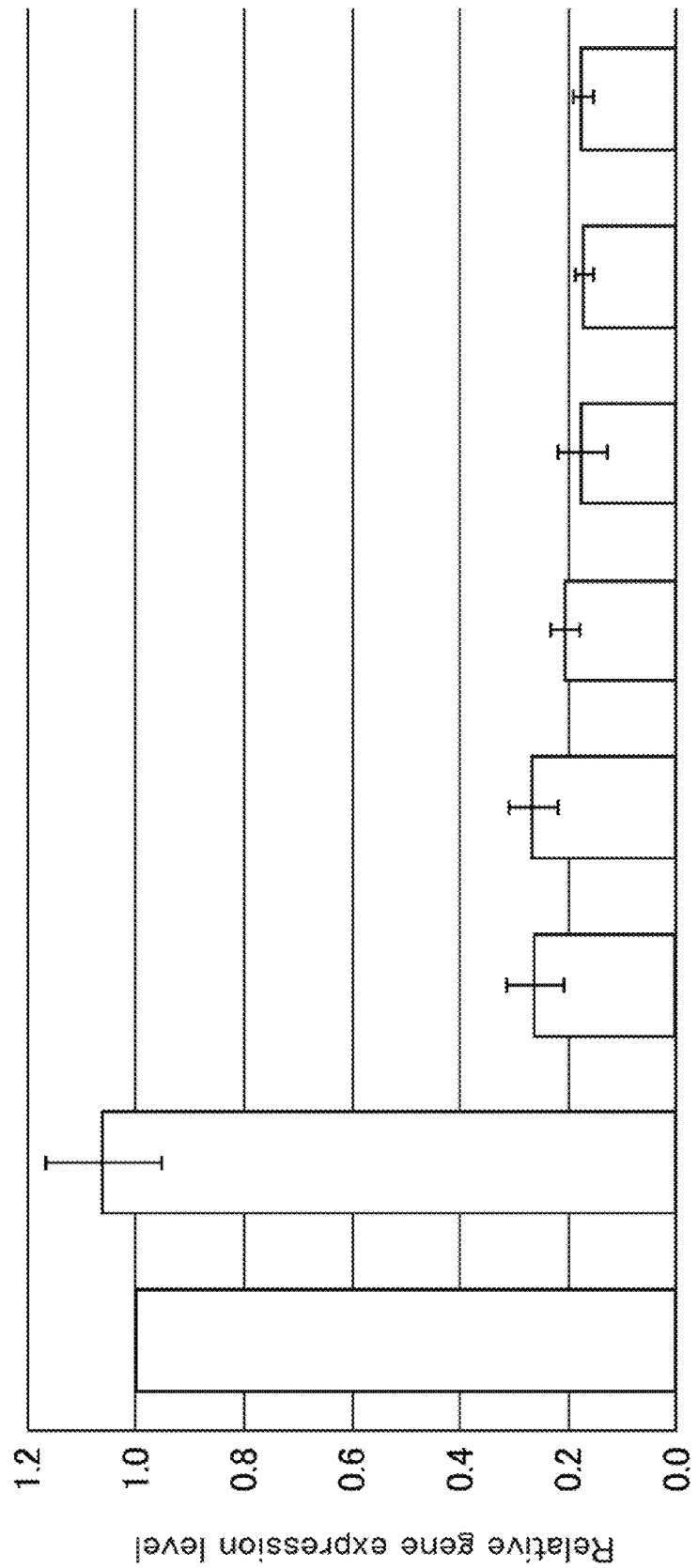
FIG. 28 is a graph showing the relative expression level of the GAPDH gene in the example of the present invention.

The results thereof are shown in FIG. 28. FIG. 28 is a graph showing the relative expression level of the GAPDH gene when each of the RNAs was used at the final concentration of 1 nmol/l. As can be seen from FIG. 28, all the ssRNAs with the varied conditions of the linker regions (Lx) and (Ly), with their lengths, the ratio between their lengths, their sequences, and the like being varied, similarly inhibited the expression of the GAPDH gene. From this result, it was found that the conditions of the linker regions (Lx) and (Ly) are not particularly limited, and they can be designed so as to have various lengths, sequences, and the like.

Example A16

Inhibitory Effect on the GAPDH Gene Expression in HCT116 Cells

Using ssRNA having undergone substitution with a linker including praline or prolinol, inhibitory effect on the GAPDH expression in HCT116 cells was examined.

(1) Materials and Method

As RNA (Ex) of the present example, RNA (Ex ssRNA) shown below was synthesized. Furthermore, ssRNA of a comparative example, Nc ssRNA as an RNAi negative control (Nc) shown below was synthesized. In each of the following sequences, a linker region (Lx) and a linker region (Ly) were provided by linking amidite having proline or prolinol shown in the table below (see Examples B) between Xc and X and between Yc and Y.

TABLE 6

| ssRNA | | |
|---|---|---|
| Comparative Example | Example | Amidite used in Lx and Ly |
| PK-0003 | PK-0004 | L-proline-diamide-amidite (Compound 10 in Scheme 3) |
| PK-0005 | PK-0006 | prolinol-urethane-amidite (Compound 6 in Scheme 7) |
| PK-0009 | PK-0010 | proline-amide-amine-amidite (Compound 12 in Scheme 3) |
| PK-0011 | PK-0012 | proline-amide-ureide-amidite (Compound 17 in Scheme 3) |
| PK-0015 | PK-0016 | prolinol-ureide-amidite (Compound 7 in Scheme 7) |

Transfection into HCT116 cells, culture, collection of RNA, synthesis of cDNA, and PCR were carried out in the same manner as in Example A13, except that each of the above RNAs was used, and the expression level of the GAPDH gene was measured. Correction with an internal standard, and calculation of a relative value of the expression level also were carried out in the same manner as in Example A13.

(2) Results

Figure 29:
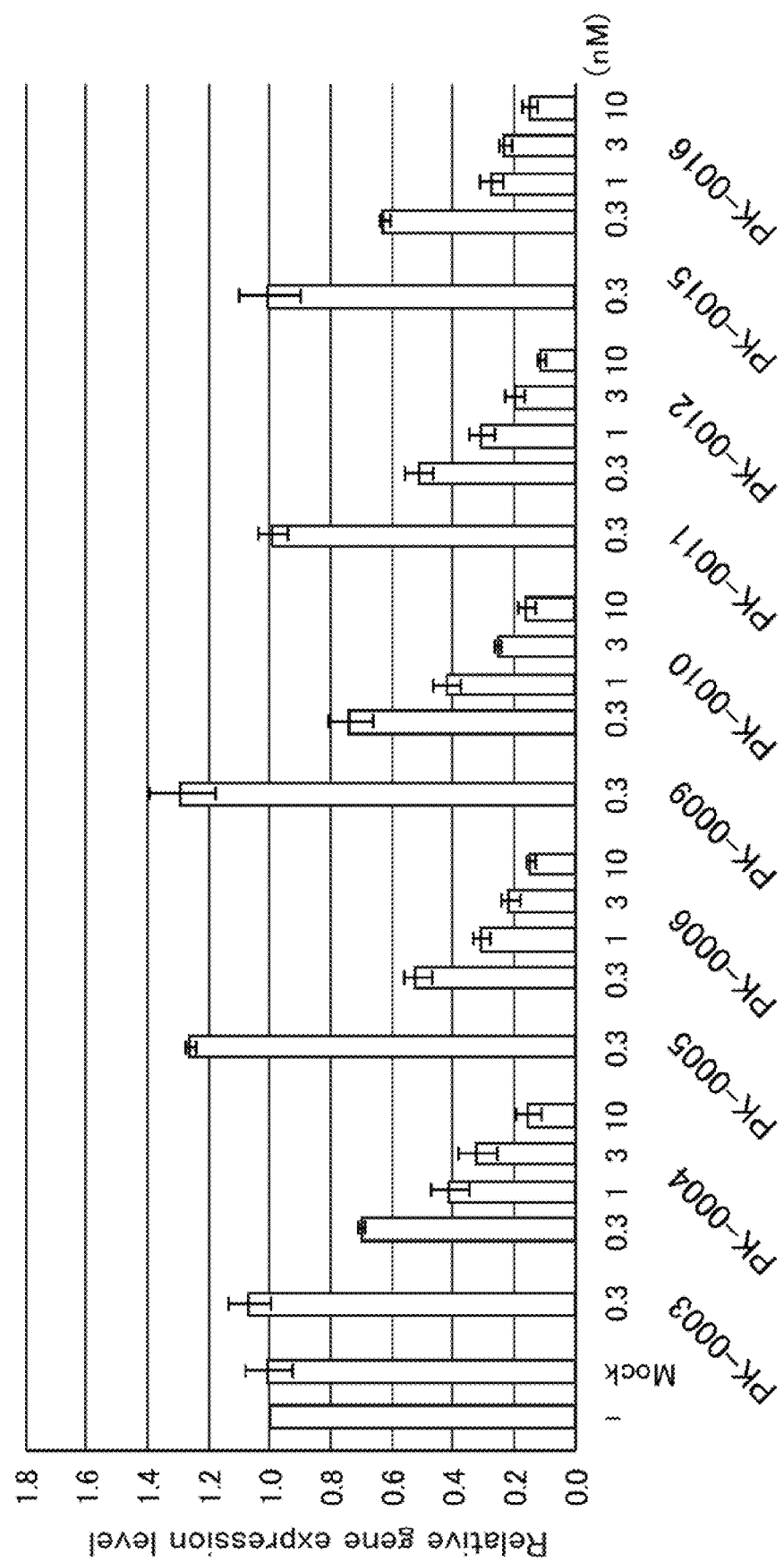
FIG. 29 is a graph showing the relative expression level of the GAPDH gene in still another example of the present invention.

The results thereof are shown in FIG. 29. FIG. 29 is a graph showing the relative expression level of the GAPDH gene. As can be seen from FIG. 29, it was found that all the Ex ssRNAs including proline or prolinol as the linker region (Lx) and the linker region (Ly) exhibit a potent inhibitory activity, and they exhibit the inhibitory activity in a concentration-dependent manner. On the other hand, no inhibitory effect was observed when the ssRNAs as the negative control were used.

Example A17

Inhibitory Effect on the GAPDH Gene Expression in HCT116 Cells

Using ssRNA having undergone substitution with a linker having proline, the inhibitory effect on the GAPDH expression in HCT116 cells was examined.

(1) Materials and Method

As RNA (Ex) of the present example, RNA (Ex ssRNA) shown below was synthesized. Furthermore, as RNA of a comparative example, Nc ssRNA as an RNAi negative control (Nc) shown below was synthesized. In each of the following sequences, a linker region (Lx) and a linker region

```
Ex: ssRNA (SEQ ID NO: 13)
5'-caugagaaguaugacaacagcc-Lx-GGCUGUUGUCAUACUUCUCAUGGUUC-Ly-gaa-3'
```
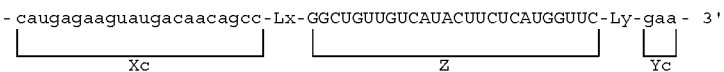

```
Nc ssRNA (SEQ ID NO: 38)
5'-ccaucaacgauaagugaaagcc-Lx-GGCUUUCACUUAUCGUUGAUGGCUUC-Ly-gaa-3'
```
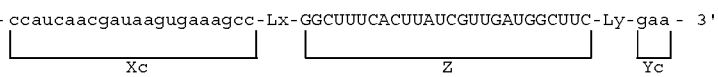

(Ly) were provided by linking amidite having proline shown in the table below (see Examples B) between Xc and X and between Yc and Y.

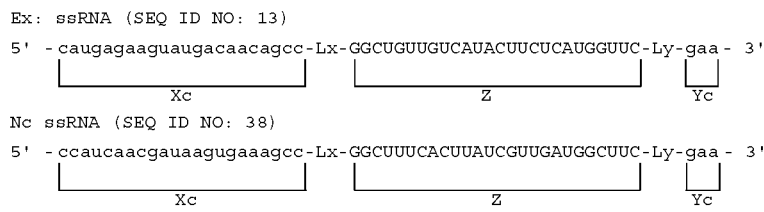

TABLE 7

| ssRNA | | |
|---|---|---|
| Comparative Example | Example | Amidite used in Lx and Ly |
| PK-0033 | PK-0034 | D-proline-diamide-amidite (Compound 9 in Scheme 3) |
| PK-0035 | PK-0036 | proline-diamide-amidite (type B) (Compound 22 in Scheme 4) |
| PK-0003 | PK-0004 | L-proline-diamide-amidite (Compound 10 in Scheme 3) |

Transfection into HCT116 cells, culture, collection of RNA, synthesis of cDNA, and PCR were carried out in the same manner as in Example A13, except that each of the above RNAs was used, and the expression level of the GAPDH gene was measured. Correction with an internal standard, and calculation of a relative value of the expression level also were carried out in the same manner as in Example A13.

(2) Results

Figure 30:
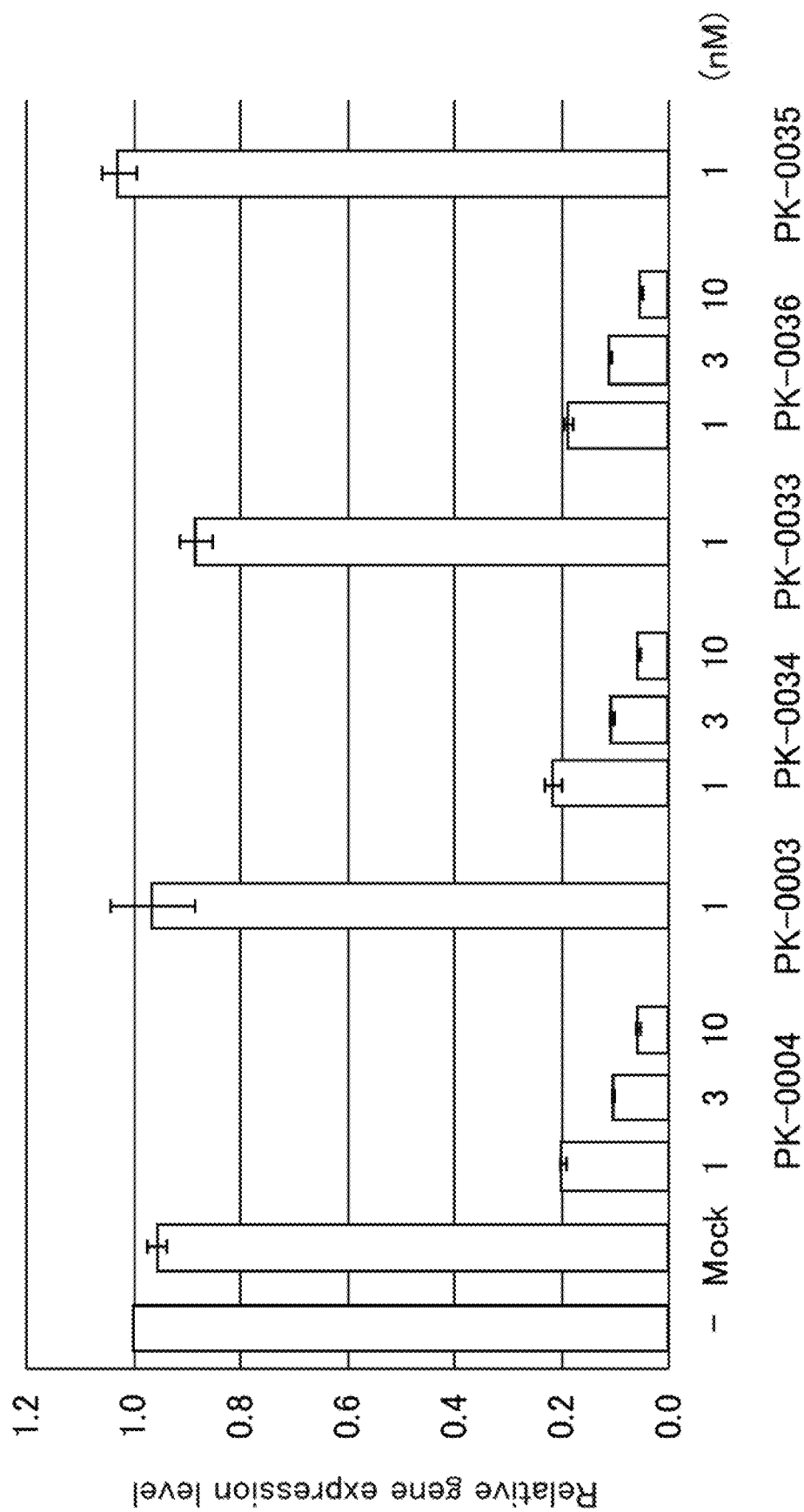
FIG. 30 is a graph showing the relative expression level of the GAPDH gene in HCT116 cells in still another example of the present invention.

The results thereof are shown in FIG. 30. FIG. 30 is a graph showing the relative expression level of the GAPDH gene in the HCT116 cells. As can be seen from FIG. 30, the Ex ssRNAs including proline as the linker region (Lx) and the linker region (Ly) exhibit a potent inhibitory activity and it was found that they exhibit the inhibitory activity in a concentration-dependent manner. On the other hand, no inhibitory effect was observed when the ssRNAs as the negative control were used.

Example A18

Ribonuclease Resistance

Regarding the ssRNA of the present invention, ribonuclease resistance was examined.

(1) Materials and Method

As RNAs (Ex) of the present example, NK-0033 of Example A5 and PK-0007 of Example A8 were used. Furthermore, as RNA of a comparative example, dsRNA (NI-0030) as a positive control (Pc) in Example A9 was used.

First, 60 pmol of each of the above RNAs, $5 \times 10^{-5}$ units of RNase A (Roche), and $5 \times 10^{-5}$ units of RNase T1 (Roche) were mixed with 20 mmol/l Tris-HCl (pH 8), and the resultant mixture was incubated at 37° C. 10 minutes, 20 minutes, and 30 minutes after the start of the incubation, the reaction of the RNases was terminated according to a conventional method. Then, the reaction solution was subjected to electrophoresis using 15% polyacrylamide gel. Thereafter, the gel was stained with SYBR Green II (Lonza, Switzerland) and then analyzed using an E-BOX-VX2 (M & S Instruments Inc., Tokyo).

(2) Results

Figure 31:
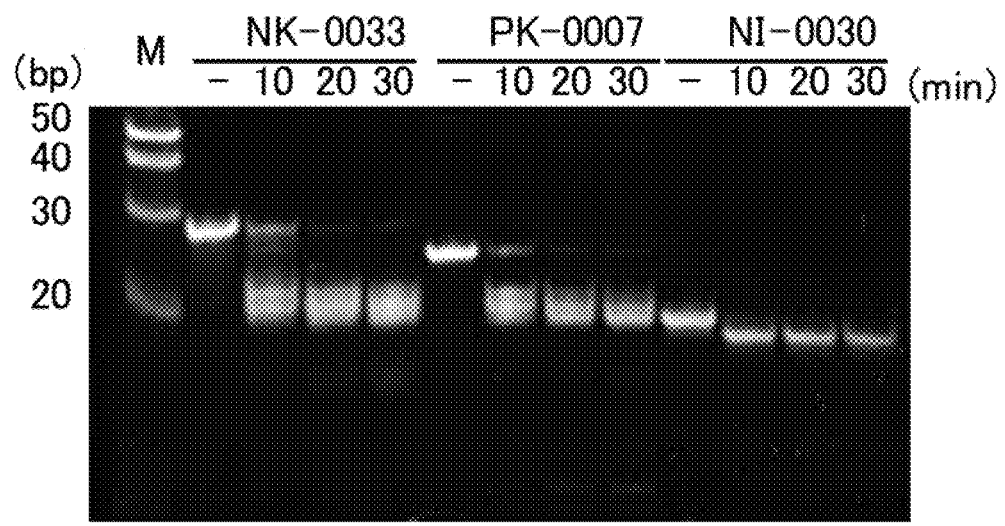
FIG. 31 is an electrophoretogram showing ribonuclease resistance in still another example of the present invention.

The results thereof are shown in FIG. 31. FIG. 31 is an electrophoretogram showing ribonuclease resistance. In FIG. 31, the lane "M" indicates a molecular weight marker, and "min" indicates the incubation time.

As can be seen from FIG. 31, NI-0030 of the comparative example was degraded almost completely after 10 minutes of incubation. In contrast. NK-0033 and PK-0007 of the example still remained even after 10 minutes of incubation. These results demonstrate that the ssRNA of the present invention is superior to dsRNA in ribonuclease resistance.

Example A19

Nuclease Resistance

Regarding the ssRNA of the present invention, the nuclease resistance was examined.

(1) Materials and Method

The same RNAs as in Example A18 were used. First, 60 pmol of each RNA and 0.5 units of S7 nuclease (Roche) were mixed with 50 mmol/l Tris-HCl (pH8) containing 5 mmol/l $CaCl_2$, and the resultant mixture was incubated at 37° C. 0.5 hours after the start of the incubation (0 h), the reaction of the S7 nuclease was terminated according to a conventional method. Then, the reaction solution was subjected to electrophoresis using 7M urea-15% polyacrylamide gel according to a conventional method. Thereafter, the gel was stained with SYBR Green II (trade name, Lonza) and then analyzed using an E-BOX-VX2 (trade name, M & S Instruments Inc.).

(2) Results

Figure 32:
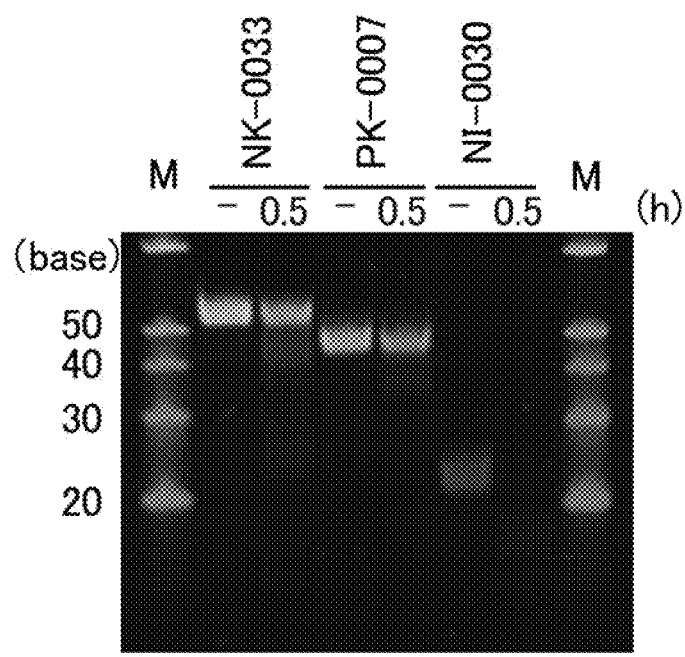
FIG. 32 is an electrophoretogram showing S7 nuclease resistance in still another example of the present invention.

The results thereof are shown in FIG. 32. FIG. 32 is an electrophoretogram showing S7 nuclease resistance. In FIG. 32, the lane "M" indicates a molecular weight marker, and "h" indicates the incubation time.

As can be seen from FIG. 32, NI-0030 of the comparative example was degraded almost completely after 0.5 hours of incubation. In contrast, NK-0033 and PK-0007 of the example still remained even after 0.5 hours of incubation. These results demonstrate that the ssRNA of the present invention is superior to dsRNA in S7 nuclease resistance.

From the respective results obtained in Examples A, it was found that the ssRNA of the present invention can be constructed regardless of the kind of a target gene, for example. Specifically, it was found that, in the ssRNA, it is possible to modify: the length of a double strand formed by the regions (X) and (Xc) and the length of a double strand formed by the regions (Y) and (Yc); the presence or absence of an unpaired base that does not form a double strand in the inner region (Z), the number and the position of such unpaired bases; the presence or absence of the linker regions (Lx) and (LA the kind and the length of the linker regions (Lx) and (Ly); and the like, for example. Thus, it can be said that the ssRNA of the present invention is a novel versatile tool that can be used for inhibiting the expression of a target gene without depending on the kind of the target gene.

Example B1

1. Synthesis of Prolinol

According to Scheme 1 shown below, prolinol protected with a dimethoxytrityl group was synthesized.

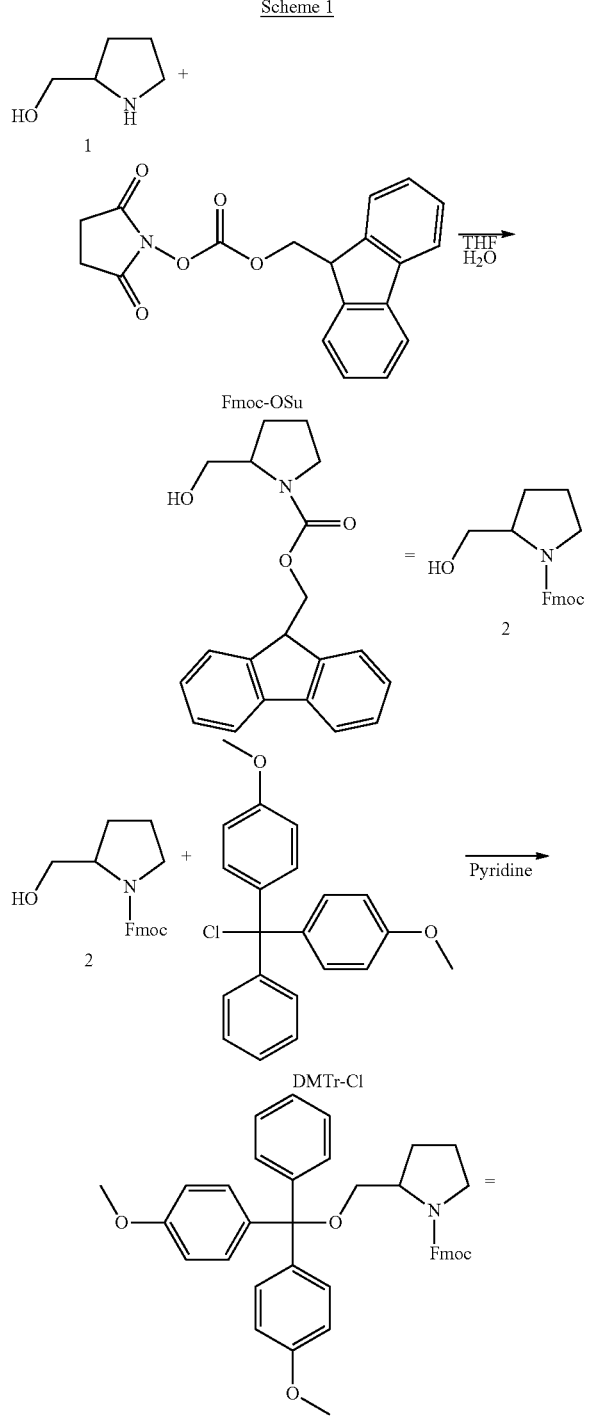

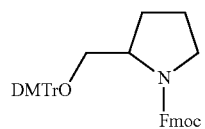

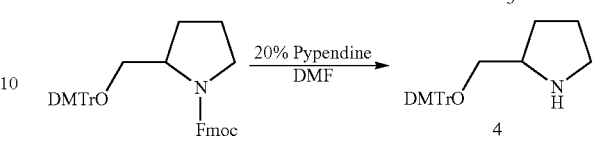

(1) Fmoc-L-Prolinol (Compound 2)

L-prolinol (Compound 1) (0.61 g, 6.0 mmol) was dissolved in 70 ml of pure water, thus preparing an L-prolinol aqueous solution. N-(9-Fluorenylmethoxycarbonyloxy)succinimide (Fmoc-OSu) (2.0 g, 6.0 mmol) was dissolved in 10 ml of THF. This THF solution was added to the L-prolinol aqueous solution, and this was stirred for 1 hour so as to react the L-prolinol and the Fmoc-OSu. The reaction solution was separated into a liquid fraction and a precipitate fraction. These fractions respectively were subjected to extraction with ethyl acetate, and organic layers respectively were collected therefrom. The thus-obtained organic layers were mixed together, and anhydrous sodium sulfate was added thereto to absorb moisture (hereinafter, this process is referred to as a "drying" process). The organic layers were filtered, and the filtrate obtained was vacuum concentrated. The residual substance obtained was purified by silica gel column chromatography (the eluent: hexane:ethyl acetate=1:1). Thus, Compound 2 was obtained (1.4 g, yield: 74%). The result of NMR analysis with respect to this compound is shown below.

$^1$H-NMR (CDCl$_3$): δ7.77 (2H, d, J=7.7 Hz, Ar—H), 7.60 (2H, J=7.3 Hz, Ar—H), 7.40 (2H, t, J=7.5 Hz, Ar—H), 7.31 (2H, t, J=7.6 Hz, Ar—H), 4.40-4.50 (2H, m, COOCH$_2$), 4.22 (1H, t, J=6.5 Hz, Ar—CH), 3.20-3.80 (5H, m, H-5, H-6), 1.75 (3H, m, H-3, H-4), 1.40 (1H, m, H-3).

(2) Fmoc-DMTr-L-Prolinol (Compound 3)

The Fmoc-L-prolinol (Compound 2) (1.4 g, 4.3 mmol) was dissolved in 20 ml of pyridine and azeotroped three times. The residual substance obtained was dissolved in 20 ml of pyridine. While stirring this solution in an ice bath under argon, 4,4'-dimethoxytrityl chloride (DMTr-Cl) (1.8 g, 5.3 mmol) was added thereto. The reaction in this reaction solution was followed by TLC using chloroform/methanol, and the reaction was allowed to proceed for 4 hours until a spot of the Fmoc-L-prolinol no longer was observed. In order to quench excess DMTr-Cl, 3 ml of methanol was added to the reaction solution, and this was stirred for 10 minutes. Chloroform was further added to the reaction solution, and thereafter, an organic layer was collected. The collected organic layer was washed with saturated saline, then with a 5% aqueous solution of sodium hydrogencarbonate, and again with saturated saline. The organic layer thus washed was dried with anhydrous sodium sulfate. The organic layer then was filtered, and the filtrate obtained was vacuum concentrated. The residual substance obtained was purified by silica gel column chromatography (the eluent: chloroform, 1% pyridine). Thus, Compound 3 was obtained (2.0 g, yield: 74%). The result of NMR analysis with respect to this compound is shown below.

$^1$H-NMR (CDCl$_3$): δ7.77 (2H, d, J=7.7 Hz, Ar—H), 7.60 (2H, d, J=7.3 Hz, Ar—H), 7.40-7.18 (13H, m, Ar—H), 6.89 (4H, d, J=8.6 Hz, Ar—H), 4.20-4.40 (2H, m, COOCH$_2$), 4.02

(1H, t, J=6.5 Hz, Ar—CH), 3.80-3.10 (5H, m, H-5, H-6), 3.73 (s, 6H, OCH₃), 1.84 (3H, m, H-3, H-4), 1.58 (1H, m, H-3).

(3) DMTr-L-Prolinol (Compound 4)

The Fmoc-DMTr-L-prolinol (Compound 3) (2.0 g, 3.2 mmol) was dissolved in 25 ml of a DMF solution containing 20% piperidine, and this was stirred for 12 hours. The solution was vacuum concentrated, and the residual substance obtained was purified by silica gel column chromatography (chloroform:methanol=85:15, containing 1% pyridine). Thus. Compound 4 was obtained (1.0 g, yield: 78%). The result of NMR analysis with respect to this compound is shown below.

$^1$H-NMR (CDCl₃) δ7.40-7.14 (9H, m, Ar—H), 6.82 (4H, d, J=8.6 Hz, Ar—H), 3.78 (6H, s, OCH₃), 3.31 (1H, m, H-6), 3.07 (2H, m, H-2, H-6), 2.90 (2H, m, H-5), 1.84 (3H, m, H-3, H-4), 1.40 (1H, m, H-3).

2. Synthesis of Amidite Derivatives

Next, according to Scheme 2 shown below, amidite derivatives having prolinol were synthesized. Hereinafter, 1-ethyl-3-(3-dimethylaminopropyl)carbodiimide hydrochloride is referred to as "EDC", and N,N-dimethylaminopyridine (4-dimethylaminopyridine) is referred to as "DMAP".

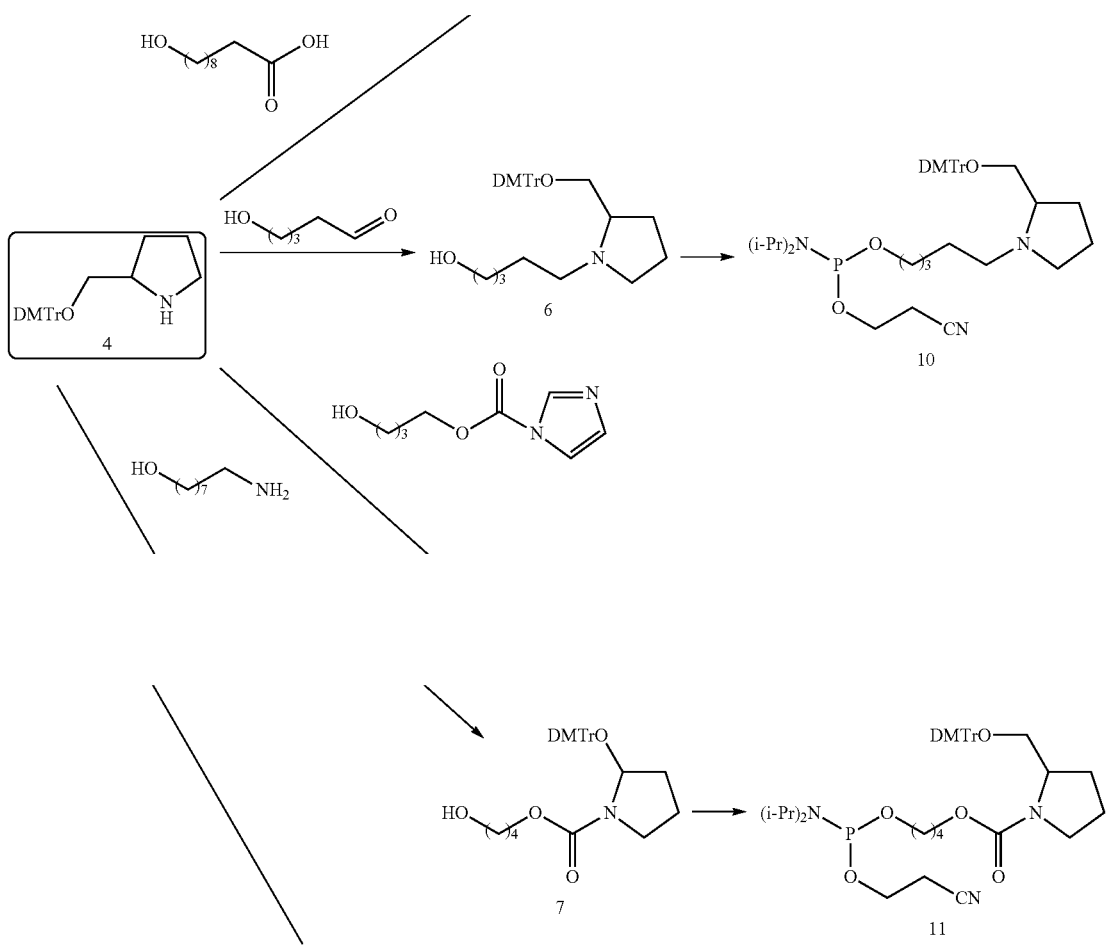

-continued

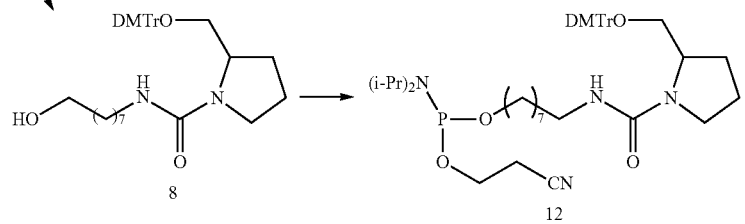

(1) DMTr-Amide-L-Prolinol (Compound 5)

The DMTr-L-prolinol (Compound 4) (0.80 g, 2.0 mmol), EDC (0.46 g, 2.4 mmol), and DMAP (0.29 g, 2.4 mmol) were dissolved in 20 ml of dichloromethane, and this then was stirred. 10-hydroxydecanoic acid (0.45 g, 2.4 mmol) was added to this solution, and this then was stirred. The reaction in this reaction solution was followed by TLC using ethyl acetate, and the reaction was allowed to proceed for 20 hours until a spot of the DMTr-L-prolinol no longer was observed. Then, dichloromethane was added to the reaction solution, and an organic layer then was collected. The collected organic layer was washed with saturated saline, and then dried with anhydrous sodium sulfate. The organic layer was filtered, and the filtrate obtained was vacuum concentrated. The residual substance was purified by silica gel column chromatography (ethyl acetate, containing 1% pyridine). Thus, Compound 5 was obtained (0.71 g, yield: 62%). The result of NMR analysis with respect to this compound is shown below.

$^1$H-NMR (CDCl$_3$): δ7.40-7.14 (9H, m, Ar—H), 6.82 (4H, d, J=8.6 Hz, Ar—H), 3.78 (6H, s, OCH$_3$), 3.68-2.93 (7H, m, H-2, H-5, H-6), 2.27-1.72 (6H, m, alkyl, H-3, H-4), 1.58 (4H, s, alkyl), 1.30 (10H, s, alkyl).

(2) DMTr-Alkyl-L-Prolinol (Compound 6)

The DMTr-L-prolinol (Compound 4) (0.80 g, 2.0 mmol) was dissolved in 15 ml of methanol. 5-hydroxypentanal (0.31 g, 3.0 mmol) was added thereto, and this then was stirred. Sodium cyanoborohydride (0.25 g, 4.0 mmol) was added to this solution, and this was further stirred. The reaction in this reaction solution was followed by TLC using ethyl acetate/hexane, and the reaction was allowed to proceed for 24 hours until a spot of the DMTr-L-prolinol no longer was observed. Ethyl acetate was added to the reaction solution, and an organic layer was collected. The collected organic layer was washed with saturated saline, and then dried with anhydrous sodium sulfate. The organic layer was filtered, and the filtrate obtained was vacuum concentrated. The residual substance was purified by silica gel column chromatography (hexane:ethyl acetate=1:1, containing 1% pyridine). Thus, Compound 6 was obtained (0.62 g, yield: 63%). The result of NMR analysis with respect to this compound is shown below.

$^1$H-NMR (CDCl$_3$): δ7.40-7.14 (9H, m, Ar—H), 6.82 (4H, d, J=8.6 Hz, Ar—H), 3.78 (6H, s, OCH$_3$), 3.70-2.86 (4H, m, CH$_2$OH, H-6), 2.06-1.79 (5H, m, alkyl, H-2, H-5), 1.74-1.49 (6H, m, alkyl, H-3, H-4), 1.45-1.27 (4H, m, alkyl).

(3) DMTr-Urethane-L-Prolinol (Compound 7)

1,4-butane diol (0.90 g, 10 mmol) was dissolved in 30 ml of dichloromethane. Carbonyldiimidazole (1.4 g, 8.6 mmol) was further added thereto, and this was stirred for 3 hours. An organic layer of this reaction solution was washed with saturated saline, and then dried with anhydrous sodium sulfate. The organic layer was filtered, and the filtrate obtained was vacuum concentrated. The residual substance was purified by silica gel column chromatography (chloroform:methanol=9:1). Thus, a compound in which one end of 1,4-butane diol was activated with carbonyldiimidazole was obtained (0.25 g, 1.5 mmol). This compound was dissolved in 15 ml of dichloromethane. The DMTr-L-prolinol (Compound 4) (0.6 g, 1.5 mmol) was added thereto, and this was stirred for 24 hours. Ethyl acetate further was added to this mixture, and an organic layer was collected. The collected organic layer was washed with saturated saline, and then dried with anhydrous sodium sulfate. The organic layer was filtered, and the filtrate obtained was vacuum concentrated. The residual substance was purified by silica gel column chromatography (hexane:ethyl acetate=1:1, containing 1% pyridine). Thus, Compound 7 was obtained (0.61 g. yield: 77%). The result of NMR analysis with respect to this compound is shown below.

$^1$H-NMR (CDCl$_3$): δ7.40-7.14 (9H, m, Ar—H), 6.82 (4H, d, J=8.6 Hz, Ar—H), 4.24-3.94 (2H, m, COOCH$_2$), 3.78 (s, 6H, OCH$_3$), 3.72-2.96 (7H, m, alkyl, H-2, H-5, H-6), 2.10-1.30 (8H, m, alkyl, H-3, H-4).

(4) DMTr-Ureido-L-Prolinol (Compound 8)

The DMTr-L-prolinol (Compound 4) (0.50 g, 1.2 mmol) and triphosgene (0.12 g, 0.40 mmol) were dissolved in 8 ml of dichloromethane, and the resultant mixture was stirred in an ice bath under argon. N. N-diisopropylethylamine (0.31 g, 2.4 mmol) was added to the solution, and this was stirred for 1 hour. Then, 8-amino-1-octanol (0.17 g, 1.2 mmol) was further added thereto, and this was stirred for 30 minutes in an ice bath in the same manner as in the above. Then, this was further stirred at room temperature for 20 hours. Dichloromethane was added to the solution, and an organic layer was collected. The collected organic layer was washed with saturated saline, and then dried with anhydrous sodium sulfate. The organic layer was filtered, and the filtrate obtained was vacuum concentrated. The residual substance was purified by silica gel column chromatography (hexane:ethyl acetate=4:1, containing 1% triethylamine). Thus, Compound 8 was obtained (0.44 g, yield: 62%). The result of NMR analysis with respect to this compound is shown below.

$^1$H-NMR (CDCl$_3$): δ7.40-7.14 (9H, m, Ar—H), 6.82 (4H, m, Ar—H), 3.78 (s, 6H, OCH$_3$), 3.68-3.25 (9H, m, CH$_2$NH, CH$_2$OH, H-2, H-5, H-6), 1.74-1.18 (16H, m, alkyl, H-3, H-4).

(5) Amidite Derivatives Having Prolinol (Compounds 9 to 12)

Compounds 9 to 12 were synthesized in the following manner using the modified prolinols (Compounds 5 to 8), respectively, as raw materials. Each of the modified prolinols and 5-benzylthio-1H-tetrazole were dissolved in 3 ml of acetonitrile. The amount of the modified prolinol used was as follows: Compound 5: 0.69 g (1.2 mmol); Compound 6: 0.60 g (1.2 mmol); Compound 7: 0.60 g (1.2 mmol); and Compound 8: 0.25 g (0.43 mmol). The amount of the 5-benzylthio-1H-tetrazole used was: 0.15 g (0.78 mmol) for Compounds 5 to 7; and 54 mg (0.15 mmol) for Compound 8. Under argon, 2-cyanoethyl N,N,N',N'-tetraisopropyl phosphorodiamidite was added to the solution, and this was stirred for 2 hours. The amount of the 2-cyanoethyl N,N,N',N'-tetraisopropyl phosphorodiamidite added was: 0.54 g (1.8 mmol) in reaction systems using Compounds 5 to 7; and 0.19 g (0.64 mmol) in a reaction system using Compound 8. Then, a saturated aqueous solution of sodium hydrogencarbonate was added to the solution, and an organic layer was extracted with dichloromethane and collected. The collected organic layer was dried with anhydrous sodium sulfate. The organic layer was filtered, and the filtrate obtained was vacuum concentrated. The residual substance was purified by silica gel column chromatography (hexane:ethyl acetate=1:1, containing 1% triethylamine). Thus. Compounds 9 to 12 were obtained. The results of NMR analysis with respect to these compounds are shown below.

DMTr-amide-L-prolinol amidite (Compound 9, 0.60 g, yield: 55%)

$^1$H-NMR (CDCl$_3$): δ7.40-7.14 (9H, m, Ar—H), 6.82 (4H, d, J=8.6 Hz, Ar—H), 3.78 (6H, s, OCH$_3$), 3.68-2.93 (11H, m, CH$_2$O, POCH$_2$, CHCH$_3$, H-2, H-5. H-6), 2.58 (2H, m, CH$_2$CN), 2.27-1.72 (6H, m, alkyl, H-3, H-4), 1.58 (4H, s, alkyl), 1.30 (22H, s, alkyl, CHCH$_3$).

DMTr-alkyl-L-prolinol amidite (Compound 10, 0.71 g, yield: 60%)

$^1$H-NMR (CDCl$_3$): δ7.40-7.14 (9H, m, Ar—H), 6.82 (4H, d, J=8.6 Hz, Ar—H), 3.78 (6H, s, OCH$_3$), 3.70-2.86 (8H, m, CH$_2$O, POCH$_2$, CHCH$_3$, H-6), 2.38 (2H, m, CH$_2$CN), 2.06-1.79 (5H, m, alkyl, H-2, H-5), 1.74-1.49 (6H, m, alkyl, H-3, H-4), 1.37-1.10 (16H, m, alkyl, CHCH$_3$).

DMTr-urethane-L-prolinol amidite (Compound 11, 0.67 g, yield: 52%)

$^1$H-NMR (CDCl$_3$): δ7.40-7.14 (9H, m, Ar—H), 6.82 (4H, d, J=8.6 Hz, Ar—H), 4.24-3.94 (2H, m, COOCH$_2$), 3.78 (s, 6H, OCH$_3$), 3.72-2.96 (11H, m, CH$_2$O, POCH$_2$, CHCH$_3$, H-2, H-5. H-6), 2.58 (2H, m, CH$_2$CN), 2.10-1.46 (8H, m, alkyl, H-3, H-4), 1.34-1.10 (12H, m, CHCH$_3$).

DMTr-ureido-L-prolinal amidite (Compound 12, 0.20 g, yield: 61%)

$^1$H-NMR (CDCl$_3$): δ7.40-7.14 (9H, m, Ar—H), 6.82 (4H, m, Ar—H), 3.78 (s, 6H, OCH$_3$), 3.65-3.25 (13H, m, CH$_2$O, POCH$_2$, CHCH$_3$, H-2, CH$_2$NH, CH$_2$OH, H-2, H-5, H-6), 2.73 (2H, m, CH$_2$CN), 2.10-1.48 (16H, m, alkyl, H-3, H-4), 1.35-1.10 (12H, m, CHCH$_3$).

Example B2

Next, according to Scheme 3 shown below, amidite derivatives having L-proline were synthesized.

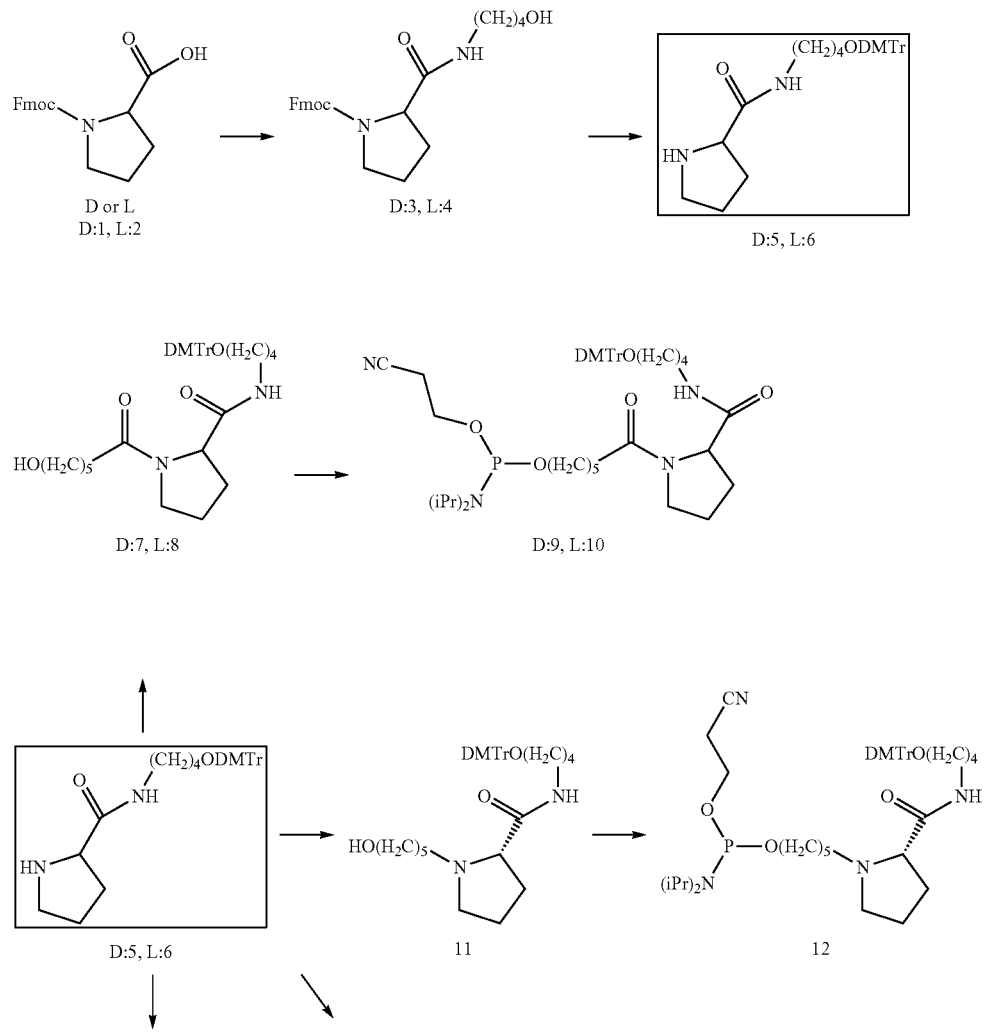

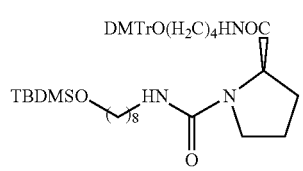
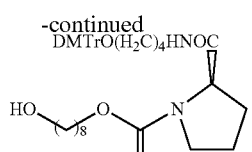
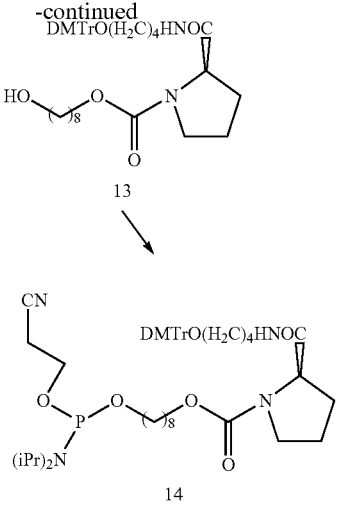
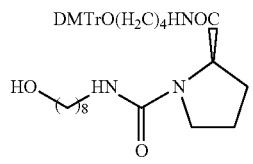
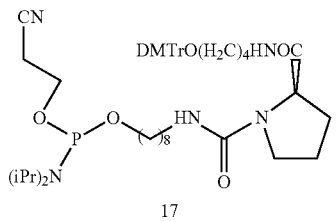

(1) DMTr-Hydroxy Amide Amino-L-Proline (Compound 11)

An acetic acid buffer (7 ml) was added to an ethanol solution (7 ml) containing DMTr-amide-L-proline (Compound 6) (1.00 g, 2.05 mmol) and 5-hydroxypentanal (0.33 g, 3.07 mmol) under ice-cooling. The resultant mixture was stirred for 20 minutes under ice-cooling. Thereafter, sodium cyanoboron (0.77 g, 12.28 mmol) was further added thereto, and this was stirred for 7 hours at room temperature. The mixture was diluted with dichloromethane, washed with water, and then further washed with saturated saline. Then, the organic layer was collected and dried with sodium sulfate. The organic layer was filtered, and the solvent in the resultant filtrate was removed by evaporation under reduced pressure. The residual substance obtained was applied to silica gel column chromatography (the eluent: $CH_2Cl_2:CH_3OH=98:2$, containing 0.05% pyridine). Then, the product obtained was applied to silica gel column chromatography (the eluent: $CH_2Cl_2:CH_3OH=98:2$, containing 0.05% pyridine), and the product obtained was further subjected to silica gel column chromatography (the eluent: dichloromethane:acetone=7:3, containing 0.05% pyridine). Thus, Compound 11 in the form of colorless syrup was obtained (0.49 g, yield: 41%).

Ms (FAB+): m/z 575 ($M^+$), 303 ($DMTr^+$)

(2) DMTr-Amide Amino-L-Proline Amidite (Compound 12)

The thus-obtained DMTr-hydroxy amide amino-L-proline (Compound 11) (0.50 g, 0.87 mmol) was mixed with anhydrous acetonitrile, and the mixture was azeotropically dried at room temperature. To the residual substance obtained, diisopropylammonium tetrazolide (178 mg, 1.04 mmol) was added. The resultant mixture was deaerated under reduced pressure and filled with argon gas. Anhydrous acetonitrile (1 ml) was added to the mixture, and an anhydrous acetonitrile solution (1 ml) of 2-cyanoethoxy-N,N, N',N'-tetraisopropyl phosphorodiamidite (313 mg, 1.04 mmol) was further added thereto. This mixture was stirred for 4 hours at room temperature in an argon atmosphere. Then, the mixture was diluted with dichloromethane, and this was washed with saturated sodium bicarbonate water and then with saturated saline. An organic layer was collected and dried with sodium sulfate. Thereafter, the organic layer was filtered. The solvent in the filtrate obtained was removed by evaporation under reduced pressure. The residual substance obtained was applied to column chromatography using amino silica as a filler (the eluent: hexane:acetone=7:3, containing 0.05% pyridine). Thus, Compound 12 in the form of colorless syrup was obtained (0.57 g, purity: 93%, yield: 79%). The purity was measured by HPLC (hereinafter the same). The result of NMR analysis with respect to this compound is shown below.

$^1$H-NMR ($CDCl_3$): δ7.41-7.43 (m, 2H, Ar—H), 7.28-7.32 (m, 4H, Ar—H), 7.25-7.27 (m, 2H, Ar—H), 7.18-7.21 (m, 1H, Ar—H), 6.80-6.84 (m, 4H, Ar—H), 3.73-3.84 (m, 1H), 3.79 (s, 6H, $OCH_3$), 3.47-3.64 (m, 3H), 3.12-3.26 (m, 2H), 3.05 (t, J=6.4 Hz, 2H, $CH_2$), 2.98-2.02 (m, 2H), 2.61 (t, J=5.8 Hz, 2H, $CH_2$), 2.55-2.63 (m, 2H), 2.27-2.42 (m, 1H, CH), 2.31 (t, 7.8 Hz, 2H, $CH_2$), 2.03-2.19 (m, 1H, CH), 1.40-1.90 (m, 8H), 1.23-1.33 (m, 5H), 1.14-1.20 (m, 12H, $CH_3$);

P-NMR ($CDCl_3$): δ146.91;

Ms (FAB+): m/z 774 ($M^+$), 303 ($DMTr^+$), 201 ($C_8H_{19}N_2OP^+$).

(3) DMTr-Hydroxy Amide Carbamoyl-L-Proline (Compound 13)

To an anhydrous acetonitrile solution (10 ml) in which the DMTr-amide-L-proline (Compound 6) (1.00 g, 2.05 mmol) had been dissolved, an anhydrous acetonitrile solution (20 ml) in which 1-imidazo carbonyloxy-8-hydroxyoctane (1.12 g, 4.92 mmol) has been dissolved was added at room temperature in an argon atmosphere. This mixture was heated at 40° C. to 50° C. for 2 days, and then was allowed to stand at room temperature for 5 days. The solvent in the mixture was removed by evaporation under reduced pressure. The residual substance obtained was applied to silica gel column chromatography (the eluent: dichloromethane:acetone=4:1, containing 0.05% pyridine). Thus, Compound 13 in the form of colorless syrup was obtained (0.68 g, yield: 50%). The result of NMR analysis with respect to this compound is shown below.

$^1$H-NMR (CDCl$_3$): δ7.90-7.42 (m, 2H, Ar—H), 7.27-7.31 (m, 6H, Ar—H), 7.17-7.21 (m, 1H, Ar—H), 6.79-6.82 (m, 4H, Ar—H), 4.23-4.30 (m, 1H), 4.05-4.10 (m, 2H), 3.79 (s, 6H, OCH$_3$), 3.60-3.65 (m, 2H), 3.32-3.55 (m, 2H), 3.16-3.29 (m, 2H), 3.01-3.07 (m, 2H), 2.38-2.40 (m, 1H, CH), 1.83-1.90 (m, 2H), 1.57-1.69 (m, 8H), 1.26-1.36 (m, 2H);

Ms (FAB+): m/z 602 (M$^+$) 303 (DMTr$^+$).

(4) DMTr-Amide Carbamoyl-L-Proline Amidite (Compound 14)

The thus-obtained DMTr-hydroxy amide carbamoyl-L-proline (Compound 13) (0.63 g, 1.00 mmol) was mixed with anhydrous pyridine, and the resultant mixture was azeotropically dried at room temperature. Diisopropylammonium tetrazolide (206 mg, 1.20 mmol) was added to the residual substance obtained, and the resultant mixture was deaerated under reduced pressure and filled with argon gas. Anhydrous acetonitrile nil) was added to the mixture, and an anhydrous acetonitrile solution (1 ml) of 2-cyanoethoxy-N,N,N',N'-tetraisopropyl phosphorodiamidite (282 mg, 1.12 mmol) was further added thereto. This mixture was stirred for 4 hours at room temperature in an argon atmosphere. Then, the mixture was diluted with dichloromethane, and this was washed with saturated sodium bicarbonate water and then with saturated saline. An organic layer was collected and dried with sodium sulfate. Thereafter, the organic layer was filtered. The solvent in the filtrate obtained was removed by evaporation under reduced pressure. The residual substance obtained was applied to column chromatography using amino silica as a filler (the eluent: hexane:acetone=7:3, containing 0.5% pyridine). Thus. Compound 14 in the form of colorless syrup was obtained (0.74 g, purity: 100%, yield: 87%). The result of NMR analysis with respect to this compound is shown below.

P-NMR (CDCl$_3$): δ147.19;

Ms (FAB+): m/z 860 (M$^+$), 303 (DMTr$^+$), 201 (C$_8$H$_{19}$N$_2$OP$^+$).

(5) DMTr-T-Butyl Dimethyl Siloxy Amide Ureido-L-Proline (Compound 15)

An anhydrous tetrahydrofuran solution (10 ml) was added to triphosgene (1.22 g, 4.10 mmol) under ice-cooling in an argon atmosphere. An anhydrous tetrahydrofuran solution (1.0 ml) in which DMTr-amide-L-proline (Compound 6) (1.00 g, 2.05 mmol) and DIEA (9.80 g, 75.8 mmol) had been dissolved was instilled in this mixture under ice-cooling in an argon atmosphere for 30 minutes. Thereafter, this was stirred for 1 hour at room temperature. An anhydrous tetrahydrofuran solution (20 ml) in which 10-amino-1-t-butyl dimethyl siloxy decane (2.66 g, 10.25 mmol) and DIEA (3.20 g, 24.76 mmol) had been dissolved was instilled in the mixture under ice-cooling in an argon atmosphere for 45 minutes. Then, the mixture was stirred overnight at room temperature in an argon atmosphere. This mixture was diluted with ethyl acetate (200 ml), and an organic layer was collected. The organic layer was washed with saturated sodium bicarbonate water and then further washed with saturated saline. Then, the organic layer was collected and dried with sodium sulfate. The organic layer was filtered, and the solvent in the filtrate obtained was removed by evaporation under reduced pressure. The residual substance obtained was applied to silica gel column chromatography (the eluent: dichloromethane:acetone=4:1, containing 0.05% pyridine). Thus, Compound 15 in the form of colorless syrup was obtained (0.87 g, yield: 55%).

(6) DMTr-Hydroxy Amide Ureido-L-Proline (16)

To the thus-obtained DMTr-t-butyl dimethyl siloxy amide ureido-L-proline (15) (0.87 g, 1.12 mmol), an anhydrous tetrahydrofuran dichloromethane solution (10 ml) was added at room temperature in an argon atmosphere. To the mixture, a 1 mol/l tetrabutylammonium fluoride-containing tetrahydrofuran solution (4.69 ml, Tokyo Chemical Industry Co., Ltd.) was added, and this was stirred for 3 days at room temperature in an argon atmosphere. The mixture was diluted with dichloromethane (150 ml), and this was washed with water and then further washed with saturated saline. An organic layer was collected and dried with sodium sulfate. Thereafter, the organic layer was filtered. The solvent in the filtrate obtained was removed by evaporation under reduced pressure. The residual substance obtained was applied to silica gel column chromatography (the eluent: dichloromethane:acetone=1:1, containing 0.05% pyridine). Thus, Compound 16 in the form of colorless syrup was obtained (0.68 g, yield: 92%). The result of NMR analysis with respect to this compound is shown below.

$^1$H-NMR (CDCl$_3$): δ7.41-7.43 (m, 2H, Ar—H), 7.27-7.31 (m, 4H, Ar—H), 7.19-7.26 (m, 2H, Ar—H) 7.19-7.21 (m, 1H, Ar—H), 6.80-6.83 (m, 4H, Ar—H), 4.34 (t, 2H, CH$_2$), 3.79 (s, 6H, OCH$_3$), 3.63 (d, 1H, J=6.4 Hz, CH$_2$), 3.61 (d, 1H, J=6.4 Hz, CH$_2$), 3.34-3.37 (m, 1H, CH), 3.16-3.27 (m, 5H), 3.04 (t, J=5.9 Hz, 2-H, CH$_2$), 2.38-2.45 (m, 1H, CH), 1.83-2.05 (m, 3H), 1.45-1.64 (m, 8H), 1.25-1.38 (m, 7H).

(7) DMTr-Amide Ureido-L-Proline Amidite (Compound 17)

The thus-obtained DMTr-hydroxy amide ureido-L-proline (Compound 16) (0.62 g, 0.94 mmol) was mixed with anhydrous acetonitrile, and the resultant mixture was azeotropically dried at room temperature. Diisopropylammonium tetrazolide (192 mg, 1.12 mmol) was added to the residual substance obtained, and the resultant mixture was deaerated under reduced pressure and filled with argon gas. Anhydrous acetonitrile (1 ml) was added to the mixture, and an anhydrous acetonitrile solution (1 ml) of 2-cyanoethoxy-N,N,N',N'-tetraisopropyl phosphorodiamidite (282 mg, 1.12 mmol) was further added thereto. This was stirred for 4 hours at room temperature in an argon atmosphere. Then, the mixture was diluted with dichloromethane, and this was washed with saturated sodium bicarbonate water and then with saturated saline. An organic layer was collected and dried with sodium sulfate. Thereafter, the organic layer was filtered. The solvent in the filtrate obtained was removed by evaporation under reduced pressure. The residual substance obtained was applied to column chromatography using amino silica as a filler (the eluent: hexane:acetone=1:1, containing 0.05% pyridine). Thus, Compound 17 in the form of colorless syrup was obtained (0.77 g, purity: 88%, yield: 84%). The result of NMR analysis with respect to this compound is shown below.

P-NMR (CDCl$_3$): δ147.27;

Ms (FAB+): m/z 860 (M$^+$+1), 303 (DMTr$^+$), 201 (C$_8$H$_{19}$N$_2$OP$^+$).

Example B3

Synthesis of Proline-Diamide-Amidite

In order to produce a nucleic acid molecule of the present invention including a linker having a proline backbone, L-proline-diamide-amidite and D-proline-diamide-amidite were synthesized according to Scheme 3.

(B3-1) L-Proline-Diamide-Amidite (1) Fmoc-Hydroxy Amide-L-Proline (Compound 4)

Compound 2 (Fmoc-L-proline) in Scheme 3 was used as a starting material. Compound 2 (10.00 g, 29.64 mmol), 4-amino-1-butanol (3.18 g, 35.56 mmol), and 1-hydroxybenzotriazole (10.90 g, 70.72 mmol) were mixed together. The mixture was deaerated under reduced pressure and filled with argon gas. Anhydrous acetonitrile (140 ml) was added to the mixture at room temperature, and an anhydrous acetonitrile solution (70 ml) of dicyclohexylcarbodiimide (7.34 g, 35.56 mmol) was further added thereto. Thereafter, this was stirred for 15 hours at room temperature in an argon atmosphere. After the completion of the reaction, the generated precipitate was removed by filtration, and the solvent in the collected filtrate was removed by evaporation under reduced pressure. Dichloromethane (200 ml) was added to the residual substance obtained, and the mixture was washed with saturated sodium bicarbonate water (200 ml). Then, an organic layer was collected and dried with magnesium sulfate. Thereafter, the organic layer was filtered, and the solvent in the filtrate obtained was removed by evaporation under reduced pressure. Diethyl ether (200 ml) was added to the residual substance, thereby turning the residual substance to powder. The thus-obtained powder was collected by filtration. Thus, Compound 4 in the form of colorless powder was obtained (10.34 g, yield: 84%). The result of NMR analysis with respect to this compound is shown below.

$^1$H-NMR (CDCl$_3$): δ7.76-7.83 (m, 2H, Ar—H), 7.50-7.63 (m, 2H, Ar—H), 7.38-7.43 (m, 2H, Ar—H), 7.28-7.33 (m, 2H, Ar—H), 4.40-4.46 (m, 1H, CH), 4.15-4.31 (m, 2H, CH$_3$), 3.67-3.73 (m, 2H, CH$_2$), 3.35-3.52 (m, 2H, CH$_2$), 3.18-3.30 (m, 2H, CH$_2$), 2.20-2.50 (m, 4H), 1.81-2.03 (m, 3H), 1.47-1.54 (m, 2H);

Ms (FAB+): m/z 409 (M+H$^+$).

(2) DMTr-Amide-L-Proline (Compound 6)

Fmoc-hydroxy amide-L-proline (Compound 4) (7.80 g, 19.09 mmol) was mixed with anhydrous pyridine (5 ml), and the resultant mixture was azeotropically dried twice at room temperature. To the residual substance obtained, 4,4'-dimethoxytrityl chloride (8.20 g, 24.20 mmol), DMAP (23 mg, 0.19 mmol), and anhydrous pyridine (39 ml) were added. This mixture was stirred for 1 hour at room temperature. Thereafter, methanol (7.8 ml) was added thereto, and this was stirred for 30 minutes at room temperature. This mixture was diluted with dichloromethane (100 ml), and washed with saturated sodium bicarbonate water (150 ml). Thereafter, an organic layer was separated. The organic layer was dried with sodium sulfate, and then filtered. The solvent in the filtrate obtained was removed by evaporation under reduced pressure. Anhydrous dimethylformamide (39 ml) and piperidine (18.7 ml, 189 mmol) were added to the thus-obtained unpurified residual substance, and this was stirred for 1 hour at room temperature. After the completion of the reaction, the solvent in the mixture was removed by evaporation under reduced pressure at room temperature. The residual substance obtained was applied to silica gel column chromatography (trade name: Wakogel C-300, the eluent: CH$_2$Cl$_2$:CH$_3$OH=9:1, containing 0.05% pyridine). Thus, Compound 6 in the form of light yellow oil was obtained (9.11 g, yield: 98%). The result of NMR analysis with respect to this compound is shown below.

$^1$H-NMR (CDCl$_3$): δ7.39-7.43 (m, 2H, Ar—H), 7.30 (d, J=8.8 Hz, 4H, Ar—H), 7.21 (tt, 1H, 4.9, 1.3 Hz, Ar—H), 6.81 (d, J=8.8 Hz, 4H, Ar—H), 3.78 (s, 6H, OCH$_3$), 3.71 (dd, H, J=6.3 Hz, 5.4 Hz, CH), 3.21 (2H, 12.9, 6.3 Hz, 2H, CH$_2$), 3.05 (t, J=6.3 Hz, 2H, CH$_2$), 2.85-2.91 (m, 2H, CH$_2$), 2.08-2.17 (m, 1H, CH), 1.85-2.00 (m, 3H), 1.55-1.65 (m, 5H);

Ms (FAB+): m/z 489 (M+H$^+$), 303 (DMTr$^+$).

(3) DMTr-Hydroxy Diamide-L-Proline (Compound 8)

An anhydrous dichloromethane solution was prepared by mixing the thus-obtained DMTr-amide-L-proline (Compound 6) (6.01 g, 12.28 mmol), EDC (2.83 g, 14.74 mmol), 1-hydroxybenzotriazole (3.98 g, 29.47 mmol), and triethylamine (4.47 g, 44.21 mmol) in anhydrous dichloromethane (120 ml). 6-hydroxyhexanoic acid (1.95 g, 14.47 mmol) was further added to this solution at room temperature in an argon atmosphere, and this then was stirred for 1 hour at room temperature in an argon atmosphere. The mixture was diluted with dichloromethane (600 ml), and this was washed three times with saturated saline (800 ml). An organic layer then was collected. The organic layer was dried with sodium sulfate, and then filtered. The solvent in the filtrate obtained was removed by evaporation under reduced pressure. Thus. Compound 8 in the form of light yellow foam was obtained (6.29 g, yield: 85%). The result of NMR analysis with respect to this compound is shown below.

$^1$H-NMR (CDCl$_3$): δ7.41-7.43 (m, 2H, Ar—H), 7.27-7.31 (m, 4H, Ar—H), 7.19-7.26 (m, 2H, Ar—H), 7.17-7.21 (m, 1H, Ar—H), 6.79-6.82 (m, 4H, Ar—H), 4.51-4.53 (m, 1H, CH), 3.79 (s, 6H, OCH$_3$), 3.61 (t, 2H, J=6.4 Hz, CH$_2$), 3.50-3.55 (m, 1H, CH), 3.36-3.43 (m, 1H, CH), 3.15-3.24 (m, 2H, CH$_2$), 3.04 (t, J=6.3 Hz, 2H, CH$_2$), 2.38-2.45 (m, 1H, CH), 2.31 (t, 6.8 Hz, 2H, CH$_2$), 2.05-2.20 (m, 1H, CH), 1.92-2.00 (m, 1H, CH), 1.75-1.83 (m, 1H, CH), 1.48-1.71 (m, 8H), 1.35-1.44 (m, 2H, CH$_2$);

Ms (FAB+): m/z 602 (M$^+$), 303 (DMTr$^+$).

(4) DMTr-Diamide-L-Proline Amidite (Compound 10)

The thus-obtained DMTr-hydroxy diamide-L-proline (Compound 8) (8.55 g, 14.18 mmol) was mixed with anhydrous acetonitrile, and the resultant mixture was azeotropically dried three times at room temperature. To the residual substance obtained, diisopropylammonium tetrazolide (2.91 g, 17.02 mmol) was added. The resultant mixture was deaerated under reduced pressure and filled with argon gas. Anhydrous acetonitrile (10 ml) was added to the mixture, and an anhydrous acetonitrile solution (7 ml) of 2-cyanoethoxy-N,N,N',N'-tetraisopropyl phosphorodiamidite (5.13 g, 17.02 mmol) was further added thereto. This mixture was stirred for 2 hours at room temperature in an argon atmosphere. Then, the mixture was diluted with dichloromethane, and this was washed with saturated sodium bicarbonate water (200 ml) three times and then with saturated saline (200 ml). An organic layer was collected and dried with sodium sulfate. Thereafter, the organic layer was filtered. The solvent in the filtrate obtained was removed by evaporation under reduced pressure. The residual substance obtained was applied to column chromatography using amino silica gel as a filler (the eluent: hexane:ethyl acetate=1:3, containing 0.05% pyridine). Thus, Compound 10 in the form of colorless syrup was obtained (10.25 g, purity: 92%, yield: 83%). The result of NMR analysis with respect to this compound is shown below.

$^1$H-NMR (CDCl$_3$): δ7.40-7.42 (m, 2H, Ar—H), 7.29-7.31 (m, 4H, Ar—H), 7.25-7.27 (m, 2H, Ar—H), 7.17-7.21 (m, 1H, Ar—H), 6.80-6.82 (m, 4H, Ar—H), 4.51-4.53 (m, 1H, CH), 3.75-3.93 (m, 4H), 3.79 (s, 6H, OCH$_3$), 3.45-3.60 (m, 4H), 3.35-3.45 (m, 1H, CH), 3.20-3.29 (m, 1H), 3.04 (t, J=6.4 Hz, 2H, CH$_2$), 2.62 (t, J=5.8 Hz, 2H, CH$_2$), 2.40-2.44 (m, 1H, CH), 2.31 (t, 7.8 Hz, 2H, CH$_2$), 2.03-2.19 (m, 1H, CH), 1.92-2.02 (m, 1H, CH), 1.70-1.83 (m, 1H, CH), 1.51-1.71 (m, 8H), 1.35-1.44 (m, 2H, CH$_2$), 1.18 (d, J=6.8 Hz, 6H, CH$_3$), 1.16 (d, J=6.8 Hz, 6H, CH$_3$);

P-NMR (CDCl$_3$): Ms δ147.17;

MS (FAB+): m/z 802 (M$^+$), 303 (DMTr$^+$), 201 (C$_8$H$_{19}$N$_2$OP$^+$).

(B3-2) D-Proline-Diamide-Amidite (1) Fmoc-Hydroxy Amide-D-Proline (Compound 3)

Compound 1 (Fmoc-D-proline) in Scheme 3 was used as a starting material. The mixture of Compound 1 (1.5 g, 4.45 mmol), dicyclohexylcarbodiimide (1.1 g, 5.34 mmol), and 1-hydroxybenzotriazole (1.5 g, 10.69 mmol) was deaerated under reduced pressure and filled with argon gas. Anhydrous acetonitrile (24 ml) was added to the mixture at room temperature, and an anhydrous acetonitrile solution (6 ml) of 4-amino-1-butanol (0.48 g, 5.34 mmol) was further added thereto. Thereafter, this was stirred for 15 hours at room temperature in an argon atmosphere. After the completion of the reaction, the generated precipitate was removed by filtration, and the solvent in the collected filtrate was removed by evaporation under reduced pressure. Dichloromethane was added to the residual substance obtained, and the mixture was washed with acetic acid buffer (pH4.0) three times and further washed with saturated sodium bicarbonate water three times. Then, an organic layer was collected and dried with magnesium sulfate. Thereafter, the organic layer was filtered, and the solvent in the filtrate obtained was removed by evaporation under reduced pressure. Diethyl ether (50 ml) was added to the residual substance, thereby turning the residual substance to powder. The thus-obtained powder was collected by filtration. Thus, Compound 3 in the form of white powder was obtained. The result of NMR analysis with respect to this compound is shown below.

$^1$H-NMR (400 MHz, CDCl$_3$): δ7.77 (d, J=7.3 Hz, 2H); 7.58 (br, 2H); 7.41 (t, J=7.3 Hz, 2H); 7.32 (t, J=7.3 Hz, 2H); 4.25-4.43 (m, 4H); 3.25-3.61 (m, 6H); 1.37-1.92 (m, 8H).

MS (FAB+): m/z 409 (M+H$^+$).

(2) DMTr-Amide-D-Proline (Compound 5)

Fmoc-hydroxy amide-D-proline (Compound 3) (1.0 g, 2.45 mmol) was mixed with anhydrous pyridine (5 ml), and the resultant mixture was azeotropically dried twice at room temperature. To the residual substance obtained, 4,4'-dimethoxytrityl chloride (1.05 g, 3.10 mmol), DMAP (3 mg, 0.024 mmol), and anhydrous pyridine (5 ml) were added. This mixture was stirred for 1 hour at room temperature. Thereafter, methanol (1 ml) was added thereto, and this was stirred for 30 minutes at room temperature. This mixture was diluted with dichloromethane, and this was washed with saturated sodium bicarbonate water. Thereafter, an organic layer was separated. The organic layer was dried with sodium sulfate, and then filtered. The solvent in the filtrate obtained was removed by evaporation under reduced pressure. Anhydrous dimethylformamide (5 ml) and piperidine (2.4 ml, 24 mmol) were added to the thus-obtained unpurified residual substance, and this was stirred for 1 hour at room temperature. After the completion of the reaction, the solvent in the mixture was removed by evaporation under reduced pressure at room temperature. The residual substance obtained was applied to silica gel column chromatography (trade name Wakogel C-300, the eluent: CH$_2$Cl$_2$:CH$_3$OH=9:1, containing 0.05% pyridine). Thus, Compound 5 in the form of light yellow oil was obtained (1.26 g, yield: 96%). The result of NMR analysis with respect to this compound is shown below.

$^1$H-NMR (400 MHz, CDCl$_3$): δ7.62 (br, 1H); 7.41-7.44 (m, 2H); 7.26-7.33 (m, 6H); 7.17-7.22 (m, 1H); 6.80-6.84 (m, 4H); 3.78 (s, 6H); 3.71 (dd, J=8.8, 5.4 Hz, 1H); 3.22 (q, 6.5 Hz, 2H); 3.07 (t, J=6.1 Hz, 2H); 2.97-3.03 (m, 1H); 2.85-2.91 (m, 1H); 1.85-2.15 (m, 3H); 1.55-1.73 (m, 6H).

MS (FAB+): m/z 489 (M+H$^+$), 303 (DMTr$^+$).

(3) DMTr-Hydroxy Diamide-D-Proline (Compound 7)

An anhydrous dichloromethane solution was prepared by mixing the thus-obtained DMTr-amide-D-proline (Compound 5) (1.2 g, 2.45 mmol). EDC (566 mg, 2.95 mmol), 1-hydroxybenzotriazole (796 mg, 5.89 mmol), and triethylamine (1.2 ml, 8.84 mmol) in anhydrous dichloromethane (24 ml), 6-hydroxyhexanoic acid (390 mg, 2.95 mmol) was further added to this solution at room temperature in an argon atmosphere, and this then was stirred for 1 hour at room temperature in an argon atmosphere. The mixture was diluted with dichloromethane, and this was washed with saturated sodium bicarbonate water three times. An organic layer was collected and dried with sodium sulfate. Thereafter, the organic layer was filtered. The solvent in the filtrate obtained was removed by evaporation under reduced pressure. Thus, Compound 7 in the form of light yellow oil was obtained (1.4 g, yield: 95%). The result of NMR analysis with respect, to this compound is shown below.

$^1$H-NMR (400 MHz, CDCl$_3$): δ7.40-7.43 (m, 2H); 7.25-7.32 (m, 6H); 7.17-7.22 (m, 1H); 6.79-6.83 (m, 4H); 3.79 (s, 6H); 3.58-3.63 (m, 2H); 3.49-3.55 (m, 1H); 3.15-3.26 (m, 2H); 3.02-3.07 (m, 2H); 2.30-2.33 (m, 2H); 2.11-2.20 (m, 1H); 1.50-1.99 (m, 13H); 1.36-1.43 (m, 2H).

MS (FAB+): m/z 602 (M$^+$), 303 (DMTr$^+$).

(4) DMTr-Diamide-D-Proline Amidite (Compound 9)

The thus-obtained DMTr-hydroxy diamide-D-proline (Compound 7) (1.2 g, 1.99 mmol) was mixed with anhydrous acetonitrile, and the resultant mixture was azeotropically dried three times at room temperature. Diisopropylammonium tetrazolide (410 mg, 2.40 mmol) was added to the residual substance obtained. The resultant mixture was deaerated under reduced pressure and filled with argon gas. Anhydrous acetonitrile (2.4 ml) was added to the mixture, and 2-cyanoethoxy-N,N,N',N'-tetraisopropyl phosphorodiamidite (722 mg, 2.40 mmol) was further added thereto. This mixture was stirred for 2 hours at room temperature in an argon atmosphere. Then, the mixture was diluted with dichloromethane, and this was washed with saturated sodium bicarbonate water three times and then washed with saturated saline. An organic layer was collected and dried with sodium sulfate. Thereafter, the organic layer was filtered. The solvent in the filtrate obtained was removed by evaporation under reduced pressure. The residual substance obtained was applied to column chromatography using amino silica gel as a filler (the eluent: hexane:ethyl acetate=1:3). Thus, Compound 9 in the form of colorless oil was obtained (1.4 g, purity: 95%, yield: 83%). The result of NMR analysis with respect to this compound is shown below.

$^1$H-NMR (400 MHz, CDCl$_3$): δ7.40-7.43 (m, 2H); 7.25-7.32 (m, 6H); 7.14-7.21 (m, 1H); 6.80-6.83 (m, 4H); 3.80-3.85 (m, 2H); 3.79 (s, 6H); 3.49-3.65 (m, 5H); 3.02-3.06 (m, 2H); 2.60-2.63 (m, 2H); 2.29-2.33 (m, 2H); 1.77-1.82 (m, 2H); 1.56-1.68 (m, 8H); 1.38-1.43 (m, 2H); 1.15-1.29 (m, 18H).

$^{31}$P-NMR (162 MHz, CDCl$_3$); δ146.94.

MS (FAB+): m/z 802 (M$^+$), 303 (DMTr$^+$), 201 (C$_8$H$_{19}$N$_2$OP$^+$).

Example B4

In order to produce a nucleic acid molecule of the present invention including a linker having a proline backbone, L-proline-diamide-amidite (type B) was synthesized according to Scheme 4 shown below.

Scheme 4

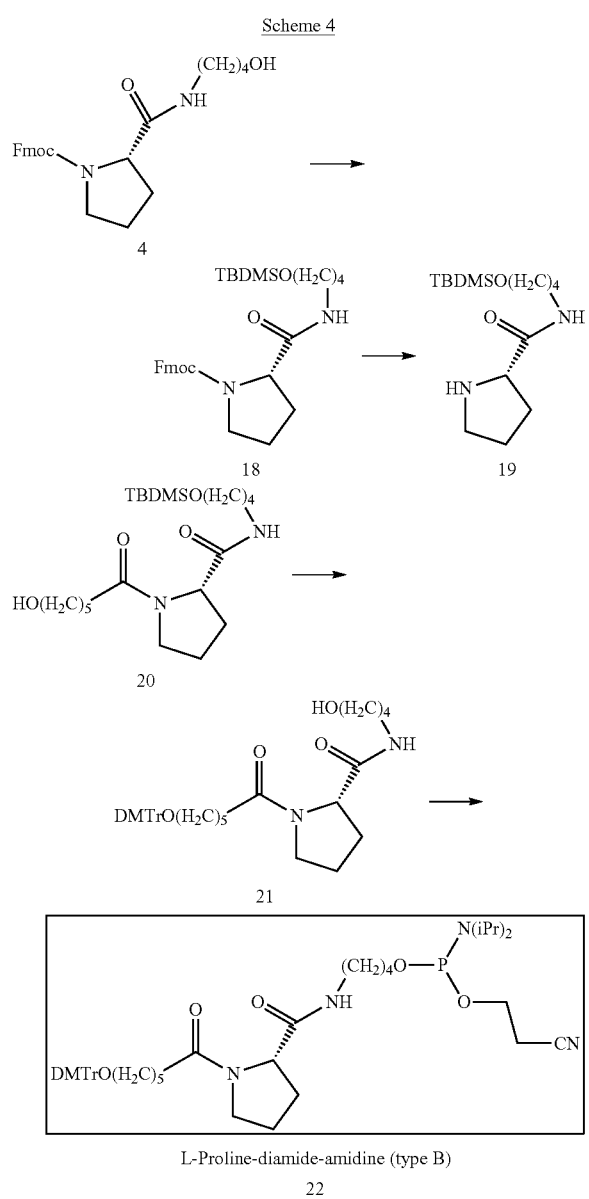

Fmoc:9-fluorenylmethyloxycarbonyl
TBDMS: tert-butyldimethylsilyl
DMTr:4,4'dimethoxytrityl (1) Fmoc-T-Butyl-Dimethyl Siloxy Amide-L-Proline (Compound 18)

Fmoc-hydroxy amide-L-proline (Compound 4) (2.00 g, 30 mmol), t-butyl-dimethyl silyl chloride (1.11 g, 35 mmol), and imidazole (10.90 g, 71 mmol) were mixed together. The mixture was deaerated under reduced pressure and filled with argon gas. Anhydrous acetonitrile (20 ml) was added to the mixture at room temperature, and this was stirred overnight at room temperature in an argon atmosphere. After the completion of the reaction, dichloromethane (150 ml) was added to the mixture. The resultant mixture was washed with water three times and then with saturated saline. An organic layer was collected and dried with magnesium sulfate. Thereafter, the organic layer was filtered. The solvent, in the filtrate obtained was removed by evaporation under reduced pressure, and the residual substance was applied to silica gel column chromatography (the eluent: $CH_2Cl_2:CH_3OH=95:5$).

Thus. Compound 18 in the form of colorless syrup was obtained (2.35 g, yield: 92%). The result of NMR analysis with respect to this compound is shown below.
$^1$H-NMR (CDCl$_3$): δ7.76-7.78 (m, 2H, Ar—H), 7.50-7.63 (m, 2H, Ar—H), 7.38-7.42 (m, 2H, Ar—H), 7.29-7.34 (m, 2H, Ar—H), 4.10-4.46 (m, 4H, CH$_2$), 3.47-3.59 (m, 4H, CH$_2$), 3.20-3.26 (m, 2H, CH), 1.85-1.95 (m, 2H), 1.42-1.55 (m, 6H), 0.96 (s, 9H, t-Bu), 0.02 (s, 6H, SiCH$_3$);
Ms (FAB+): m/z 523 (M+H$^+$).

(2) T-Butyl-Dimethyl Siloxy Amide-L-Proline (Compound 19)

To the thus-obtained Fmoc-t-butyl-dimethyl siloxy amide-L-proline (Compound 18) (1.18 g, 2.5 mmol), anhydrous acetonitrile (5 ml) and piperidine (2.4 ml) were added, and this was stirred for 1 hour at room temperature. After the completion of the reaction, acetonitrile (50 ml) was added to the mixture, and insoluble matters were removed by filtration. The solvent in the filtrate obtained was removed by evaporation under reduced pressure. The residual substance obtained was applied to silica gel column chromatography (the eluent: $CH_2Cl_2:CH_3OH=9:1$). Thus, Compound 19 in the form of colorless syrup was obtained (0.61 g, yield: 90%). The result of NMR analysis with respect to this compound is shown below.
$^1$H-NMR (CDCl$_3$): δ3.71 (dd, 1H, J=9.0 Hz, 5.2 Hz, CH), 3.61-3.64 (m, 2H, CH$_2$), 3.22-3.28 (m, 2H, CH$_2$), 2.98-3.04 (m, 1H, CH), 2.86-2.91 (m, 1H, CH), 2.08-2.17 (m, 1H, CH), 1.86-1.93 (m, 1H, CH), 1.66-1.75 (m, 2H, CH$_2$), 1.52-1.57 (m, 4H), 0.89 (s, 9H, t-Bu), 0.05 (s, 6H, SiCH$_3$);
Ms (FAB+): m/z 301 (M+H$^+$).

(3) T-Butyl-Dimethyl Siloxy Amide Hydroxy Amide-L-Proline (Compound 20)

An anhydrous dichloromethane solution was prepared by mixing the thus-obtained t-butyl-dimethyl siloxy amide-L-proline (Compound 19) (550 mg, 1.8 mmol), 6-hydroxyhexanoic acid (300 mg, 2.3 mmol), EDC (434 mg, 2.3 mmol), and 1-hydroxybenzotriazole (695 mg, 4.5 mmol) in anhydrous dichloromethane (20 ml). Triethylamine (689 mg, 6.8 mmol) was added to this solution at room temperature in an argon atmosphere, and then, this was stirred overnight at room temperature in an argon atmosphere. The mixture was washed with saturated saline. An organic layer was collected, and the collected organic layer was dried with sodium sulfate. Thereafter, the organic layer was filtered. The solvent in the filtrate obtained was removed by evaporation under reduced pressure. The residual substance obtained was applied to silica gel column chromatography (the eluent: $CH_2Cl_2:CH_3OH=9:1$). Thus, Compound 20 in the form of colorless syrup was obtained (696 mg, yield: 92%). The result of NMR analysis with respect to this compound is shown below.
$^1$H-NMR (CDCl$_3$): δ4.54 (d, 1H, CH), 3.58-3.67 (m, 5H), 3.52-3.56 (m, 1H, CH), 3.32-3.39 (m, 1H), 3.20-3.25 (m, 2H), 2.40-2.43 (m, 1H, CH), 2.33 (t, J=7.3 Hz, 2H, CH$_2$), 2.05-2.25 (m, 2H), 1.93-203 (m, 1H, CH), 1.75-1.85 (m, 1H, CM, 1.50-1.73 (m, 8H), 1.37-1.46 (m, 2H, CH$_2$), 0.87 (s, 9H, t-Bu), 0.04 (s, 6H, SiCH$_3$);
Ms (FAB+): m/z 415 (M$^+$+1).

(4) DMTr-Hydroxy Diamide-L-Proline (Type B) (Compound 21)

The thus-obtained t-butyl-dimethyl siloxy amide hydroxy amide-L-proline (Compound 20) (640 mg, 1.54 mmol) was mixed with anhydrous pyridine (1 ml), and this was azeotropically dried at room temperature. To the residual substance obtained, 4,4'-dimethoxytrityl chloride (657 mg, 1.85 mmol), DMAP (2 mg), and anhydrous pyridine (5 ml) were added, and this was stirred for 4 hours at room temperature. Thereafter, methanol (1 ml) was added thereto, and this was stirred for 30 minutes at room temperature. The mixture was diluted with dichloromethane, and this was washed with saturated sodium bicarbonate water. An organic layer was collected and dried with sodium sulfate. Thereafter, the organic layer was filtered. The solvent in the filtrate obtained was removed by evaporation under reduced pressure. To the residual substance obtained, anhydrous acetonitrile (5 ml) and a 1 mol/l tetrabutylammonium fluoride-containing tetrahydrofuran solution (1.42 ml, tetrabutylammonium fluoride 1.42 mmol) were added, and this was stirred overnight at room temperature. After the completion of the reaction, ethyl acetate (100 ml) was added to the mixture. The resultant mixture was washed with water and then with saturated saline. An organic layer was collected and dried with sodium sulfate. Thereafter, the organic layer was filtered. The solvent in the filtrate obtained was removed by evaporation under reduced pressure. The residual substance obtained was applied to silica gel column chromatography (the eluent: $CH_2Cl_2$:$CH_3OH$=95:5, containing 0.05% pyridine). Thus. Compound 21 in the form of colorless syrup was obtained (680 mg, yield: 73%). The result of NMR analysis with respect to this compound is shown below.

$^1$H-NMR (CDCl$_3$): δ7.41-7.44 (m, 2H, Ar—H), 7.26-7.33 (m, 4H, Ar—H), 7.18-7.21 (m, 2-H, Ar—H), 7.17-7.21 (m, 1H, Ar—H), 6.80-6.84 (m, 4H, Ar—H), 4.51-4.53 (d, 6.8 Hz, 1H, CH), 3.79 (s, 6H, OCH$_3$), 3.61 (dd, 2H, J=11 Hz, 5.4 Hz, CH$_2$), 3.50-3.54 (m, 1H, CH), 3.36-3.43 (m, 1H, CH), 3.20-3.26 (m, 2H, CH$_2$), 3.05 (t, J=6.4 Hz, 2H, CH$_2$), 2.38-2.45 (m, 1H, CH), 2.30 (t, J=7.8 Hz, 2H, CH$_2$), 2.05-2.25 (m, 1H, CH), 1.92-2.00 (m, 1H, CH), 1.75-1.83 (m, 1H, CH), 1.52-1.67 (m, 8H), 1.35-1.45 (m, 2H, CH$_2$);

Ms (FAB+): m/z 602 (M$^+$), 303 (DMTr$^+$).

(5) DMTr-Diamide-L-Proline Amidite (Type B) (Compound 22)

The thus-obtained DMTr-hydroxy diamide-L-proline (type B) (Compound 21) (637 mg, 1.06 mmol) was mixed with anhydrous acetonitrile, and the resultant mixture was azeotropically dried at room temperature. To the residual substance obtained, diisopropylammonium tetrazolide (201 mg, 1.16 mmol) was added, and the resultant mixture was deaerated under reduced pressure and filled with argon gas. Anhydrous acetonitrile (1 ml) was added to the mixture, and an anhydrous acetonitrile solution (1 ml) of 2-cyanoethoxy-N,N,N',N'-tetraisopropyl phosphorodiamidite (350 mg, 1.16 mmol) was further added thereto. This mixture was stirred for 4 hours at room temperature in an argon atmosphere. The mixture was diluted with dichloromethane, and this was washed with saturated sodium bicarbonate water and saturated saline. An organic layer was collected and dried with sodium sulfate. Thereafter, the organic layer was filtered. The solvent in the filtrate obtained was removed by evaporation under reduced pressure. The residual substance obtained was applied to column chromatography using amino silica gel as a filler (the eluent: hexane:acetone=7:3). Thus, Compound 22 in the form of colorless syrup was obtained (680 mg, purity: 95%, yield: 76%). The result of NMR analysis with respect to this compound is shown below.

$^1$H-NMR (CDCl$_3$): δ7.41-7.43 (m, 2H, Ar—H), 7.25-7.32 (m, 4H, Ar—H), 7.17-7.22 (m, 2H, Ar—H), 6.80-6.83 (m, 4H, Ar—H), 4.53 (d, J=7.8 Hz, 1H, CH), 3.75-3.93 (m, 3H), 3.79 (s, 6H, OCH$_3$), 3.46-3.68 (m, 5H), 3.34-3.41 (m, 1H, CH), 3.10-3.31 (m, 1H, CH), 3.05 (t, J=6.3 Hz, 2H, CH$_2$), 2.62 (t, J=6.3 Hz, 2H, CH$_2$), 2.39-2.46 (m, 1H, CH), 2.29 (t, 7.3 Hz, 2H, CH$_2$), 2.03-2.19 (m, 1H, CH), 1.90-2.00 (m, 1H, CH), 1.70-1.83 (m, 1H, CH), 1.51-1.71 (m, 8H), 1.35-1.45 (m, 2H, CH$_2$), 1.18 (d, J=6.4 Hz, 6H, CH$_3$), 1.16 (d, J=6.4 Hz, 6H, CH$_3$);

P-NMR (CH$_3$CN): δ146.90;
Ms (FAB+): m/z 803 (M$^+$+1), 303 (DMTr$^+$).

Example B5

In order to produce a nucleic acid molecule of the present invention including a linker having a proline backbone, DMTr-amide ethylene oxy ethyl amino-L-proline amidite (hereinafter referred to as "PEG spacer type") was synthesized according to Scheme 5 shown below.

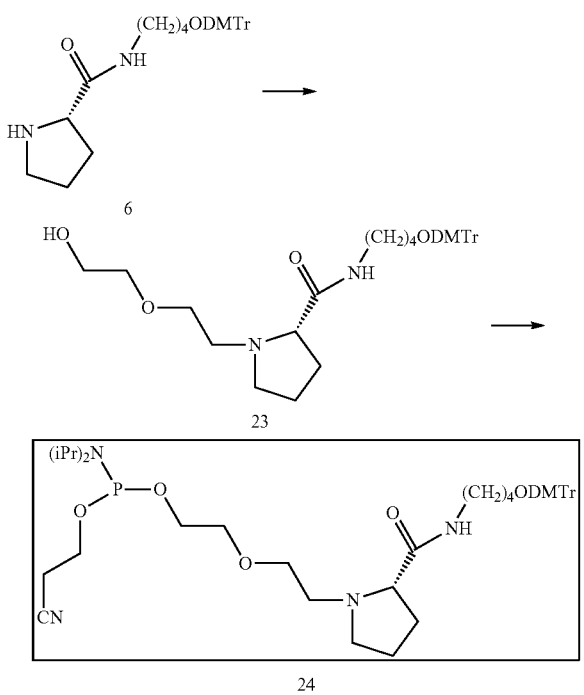

Scheme 5

(1) DMTr-Amide Hydroxy Ethoxy Ethyl Amino-L-Proline (Compound 23)

DMTr-amide-L-proline (Compound 6) (1.00 g, 2.05 mmol), 4-toluenesulfonic acid 2-(2-hydroxyethoxy)ethyl ester (3.10 g, 12.30 mmol), and anhydrous dimethylformamide solution (10 ml) of potassium carbonate (0.85 g, 6.15 mmol) were mixed together, and the resultant mixture was stirred for 4 days at room temperature in an argon atmosphere. The solvent in the mixture was removed by evaporation at room temperature under reduced pressure. Thereafter, dichloromethane (20 ml) was added thereto, and the resultant mixture was filtered. The filtrate was concentrated, and the residual substance obtained was applied to silica gel column chromatography. As eluents in the silica gel column chromatography, first, ethyl acetate containing 0.05% pyridine was used, and then, a mixture of CH$_2$Cl$_2$ and CH$_3$OH(CH$_2$Cl$_2$:CH$_3$OH=9:1) containing 0.05% pyridine was used. As a result. Compound 23 in the form of colorless syrup was obtained (1.15 g, yield: 97%). The result of NMR analysis with respect to this compound is shown below.

$^1$H-NMR (CDCl$_3$): δ7.41-7.45 (m, 2H, Ar—H), 7.27-7.31 (m, 6H, Ar—H), 7.17-7.21 (m, 1H, Ar—H), 6.79-6.82 (m, 4H, Ar—H), 3.79 (s, 6H, OCH$_3$), 3.60-3.70 (m, 2H), 3.39-3.57 (m, 4H), 3.13-3.27 (m, 3H), 3.07-3.08 (m, 2H), 2.71-2.84 (m, 1H), 2.38-2.46 (m, 1H), 2.14-2.19 (m, 1H), 1.84-1.87 (m, 1H), 1.57-1.76 (m, 8H).

(2) DMTr-Amide Ethylene Oxy Ethyl Amino-L-Proline Amidite (Compound 24)

The thus-obtained DMTr-amide hydroxy ethoxy ethyl amino-L-proline (Compound 23) (0.63 g, 1.00 mmol) was mixed with anhydrous pyridine, and the resultant mixture was azeotropically dried at room temperature. To the residual substance obtained, diisopropylammonium tetrazolide (206 mg, 1.20 mmol) was added. The resultant mixture was deaerated under reduced pressure and filled with argon gas. Anhydrous acetonitrile (1 ml) was added to the mixture, and an anhydrous acetonitrile solution (1 ml) of 2-cyanoethoxy-N,N,N',N'-tetraisopropyl phosphorodiamidite (282 mg, 1.12 mmol) was further added thereto. This mixture was stirred for 4 hours at room temperature in an argon atmosphere. Then, the mixture was diluted with dichloromethane, and this was washed with saturated sodium bicarbonate water and saturated saline. An organic layer was collected and dried with sodium sulfate. Thereafter, the organic layer was filtered. The solvent in the filtrate obtained was removed by evaporation under reduced pressure. The residual substance obtained was applied to column chromatography using amino silica gel as a filler (the eluent hexane:acetone=7:3, containing 0.05% pyridine). Thus, Compound 24 in the form of colorless syrup was obtained (0.74 g, purity: 100%, yield: 87%). The result of NMR analysis with respect to this compound is shown below.

$^{1}$H-NMR (CD$_3$CN): δ7.41-7.43 (m, 2H, Ar—H), 7.28-7.31 (m, 6H, Ar—H), 7.18-7.22 (m, 1H, Ar—H), 6.84-6.86 (m, 4H, Ar—H), 3.73-3.84 (m, 2H, CH$_2$), 3.79 (s, 6H, OCH$_3$), 3.47-3.64 (m, 7H), 3.15-3.23 (m, 1H), 3.11 (t, J=6.4 Hz, 2H, CH$_2$), 3.01 (t, =5.9 Hz, 2H, CH$_2$), 2.95-2.99 (m, 1H), 2.58-2.63 (m, 2H), 2.31-2.35 (m, 1H, CH), 2.03-2.19 (m, 1H, CH), 1.48-1.78 (m, 10H), 1.12-1.57 (m, 12H, CH$_3$).

P-NMR (CD$_3$CN): δ148.00;

Ms (FAB+): m/z 776 (M$^+$), 303 (DMTr$^+$) 201 (C$_8$H$_{19}$N$_2$OP$^+$).

Example B6

1. Synthesis of Protected Prolinol

According to Scheme 6 shown below, prolinol protected with a dimethoxytrityl group (Compound 3) was synthesized.

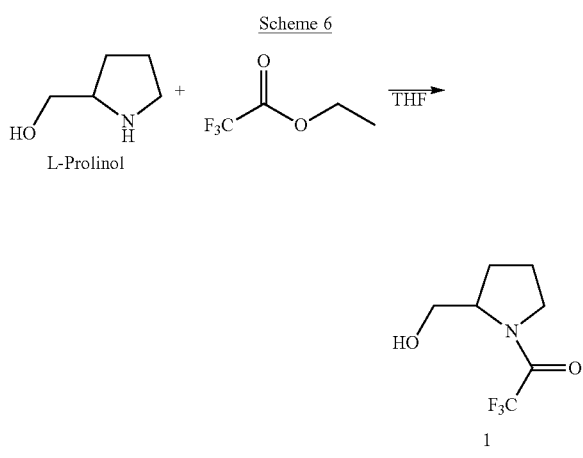

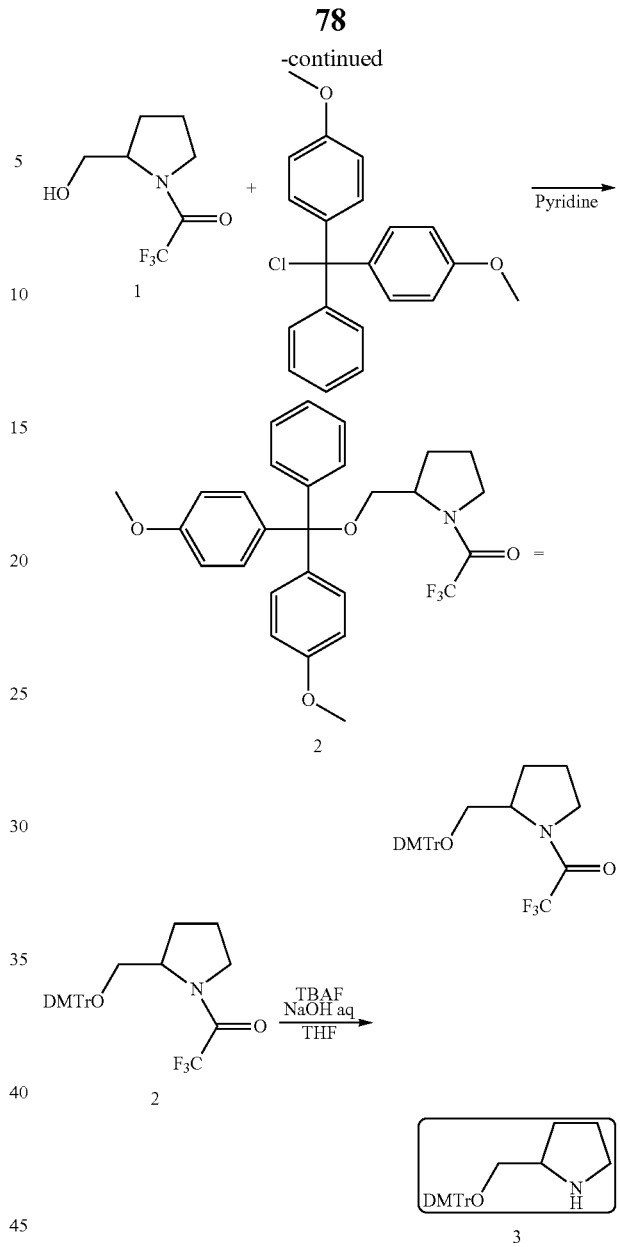

(1) Trifluoroacetyl-L-Prolinol (Compound 1)

L-prolinol (2.0 g, 20 mmol) was dissolved in 20 ml of THF. On the other hand, ethyl trifluoroacetate (3.0 g, 21 mmol) was dissolved in 20 ml of THF. Then, the latter THF solution was instilled in the former THF solution containing the L-prolinol, and this was stirred for 12 hours. This reaction solution was vacuum concentrated. Thus, Compound 1 was obtained (3.7 g, yield: 97%). The result of NMR analysis with respect to this compound is shown below.

$^{1}$H-NMR (CDCl$_3$): δ4.28-4.23 (1.0H, m, OH), 3.90-3.41 (5H, H-2, H-5, H-6, m), 2.27-1.77 (4H, H-3, H-4, m).

(2) Trifluoroacetyl-DMTr-L-Prolinol (Compound 2)

The thus-obtained trifluoroacetyl-L-prolinol (Compound 1) (3.7 g, 19 mmol) was dissolved in pyridine, and the resultant mixture was azeotropically dried three times at room temperature. The residual substance obtained was dissolved in 15 ml of pyridine, and 4,4'-dimethoxytrityl chloride (DMTr-Cl) (8.1 g, 24 mmol) was added to this mixture while stirring the mixture in an ice bath under argon. They were allowed to further react for 4 hours at room temperature. Then, in order to quench excess DMTr-Cl, 10 ml of methanol was further added to the reaction solution, and this was stirred for 10 minutes. Thereafter, dichloromethane was added to the reaction solution, and the resultant mixture was washed with a saturated aqueous solution of sodium hydrogencarbonate and saturated saline. An organic layer collected after the washing was dried with sodium sulfate. The organic layer was filtered, and the filtrate obtained was vacuum concentrated. The residual substance obtained was applied to silica gel column chromatography (eluent $CH_2Cl_2:CH_3OH=95:5$, containing 0.1% pyridine). Thus, purified Compound 2 was obtained (8.5 g, yield: 89%). The result of NMR analysis with respect to this compound is shown below.

$^1$H-NMR (CDCl$_3$): δ7.39-7.18 (9H, m, Ar—H), 6.82 (4H, d, J=8.6 Hz, Ar—H), 3.78 (6H, s, OCH$_3$), 3.70-3.41 (5H, H-2, H-5, H-6, m), 2.19-1.85 (4H, H-3, H-4, m).

(3) DMTr-L-Prolinol (Compound 3)

The thus-obtained trifluoroacetyl-DMTr-L-prolinol (Compound 2) (5 g, 10 mmol) was dissolved in 100 ml of THF. 100 ml of a 5% aqueous solution of sodium hydroxide was added to this THF solution, and this then was stirred. 5 ml of 1M tetra-n-butylammonium fluoride (TBAF) solution was added to this solution, and this was stirred for 12 hours at room temperature. This reaction solution was washed with a saturated aqueous solution of sodium hydrogencarbonate and saturated saline. An organic layer collected after the washing was dried with sodium sulfate. The organic layer was filtered, and the filtrate obtained was vacuum concentrated. Thus, Compound 3 was obtained (3.6 g, yield: 90%). The result of NMR analysis with respect to this compound is shown below.

$^1$H-NMR (CDCl$_3$): δ7.40-7.14 (9H, m, Ar—H), 6.82 (4H, d, J=8.6 Hz, Ar—H), 3.78 (6H, s, OCH$_3$), 3.31 (1H, m, H-6), 3.07 (2H, m, H-2, H-6), 2.90 (2H, m, H-5), 1.84 (3H, m, H-3, H-4), 1.40 (1H, m, H-3).

2. Synthesis of Amidite Derivative

Using the protected prolinol (Compound 3) synthesized in the item "1" above, amidite derivatives having prolinol bound in various binding forms were synthesized according to Scheme 7 shown below.

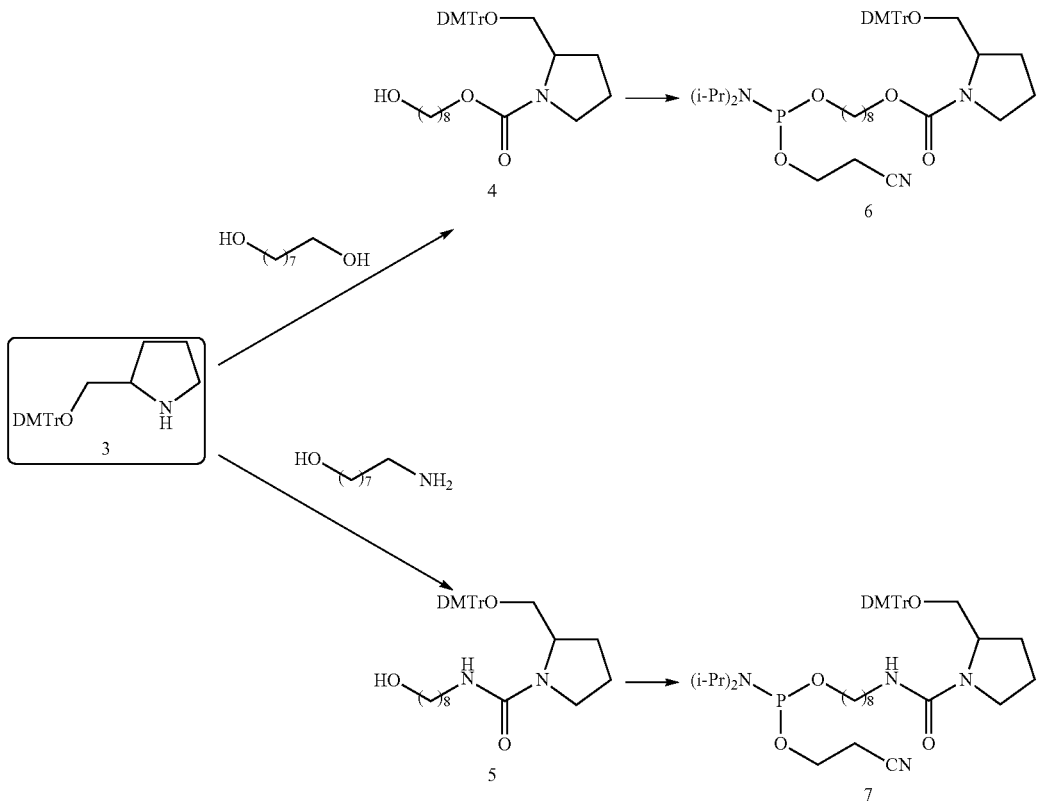

Scheme 7

(1) DMTr-Urethane-L-Prolinol (Compound 4)

1,8-octanediol (9.0 g, 62 mmol) was dissolved in 90 ml of THF, and this solution was placed under argon. On the other hand, carbonyldiimidazole (2.0 g, 12 mmol) was dissolved in 10 ml of THF. The latter THF solution was added to the former THF solution, and this was stirred for 1 hour at room temperature. This reaction solution was washed with water until a spot of the 1,8-octanediol no longer was observed in TLC. Further, an organic layer collected after the washing was washed with saturated saline and dried with anhydrous sodium sulfate. The organic layer was filtered, and the filtrate obtained was vacuum concentrated. The residual substance obtained was applied to silica gel column chromatography (the eluent: $CH_2Cl_2:CH_3OH=95:5$). Thus, a purified title compound was obtained. In this compound, one end of the 1,8-octanediol was activated with carbonyldiimidazole (2.3 g, yield: 77%).

0.9 g of the compound was dissolved in 10 ml of acetonitrile, and this solution was placed under argon. On the other hand, DMTr-L-prolinol (Compound 3) (1.9 g, 4.8 mmol) was dissolved in 20 ml of acetonitrile. The latter acetonitrile solution was added to the former acetonitrile solution, and this was stirred for 24 hours at room temperature. Then, this reaction solution was washed with a saturated aqueous solution of sodium hydrogencarbonate and saturated saline. An organic layer was collected and dried with anhydrous sodium sulfate. The organic layer was filtered, and the filtrate obtained was vacuum concentrated. The residual substance obtained was applied to silica gel column chromatography (the eluent: dichloromethane:acetone=9:1, containing 0.1% pyridine). Thus, purified Compound 4 (prolinol-urethane-amidite) was obtained (1.5 g, yield: 65%). The result of NMR analysis with respect to this compound is shown below.

$^1$H-NMR (CDCl$_3$): δ7.40-7.14 (9H, m, Ar—H), 6.82 (4H, d, J=8.6 Hz, Ar—H), 4.24-3.94 (2H, m, COOCH$_2$), 3.78 (s, 6H, OCH$_3$), 3.72-2.96 (7H, m, alkyl, H-2, H-5, H-6), 2.10-1.30 (16H, m, alkyl, H-3, H-4).

FAB-MS: 576 [M+H]$^+$.

(2) DMTr-Ureido-L-Prolinol (Compound 5)

Under argon, triphosgene (2.0 g, 6.7 mmol) was dissolved in 10 ml of THF, and this was stirred at 0° C. On the other hand, DMTr-L-prolinol (Compound 3) (1.3 g, 3.2 mmol) and N,N-diisopropylethylamine (16 g, 124 mmol) were dissolved in 10 ml of THF, and this solution was instilled in the THF solution of triphosgene. This reaction solution was stirred for 1 hour at 0° C. and then for 2 hours at worn temperature. Then, 8-amino-1-octanol (2.3 g, 16 mmol) and N,N-diisopropylethylamine (5.0 g, 38 mmol) were dissolved in 30 ml of THF. The reaction solution having been stirred was instilled in this THF solution, and this was stirred for 1 hour at 0° C. and then for 48 hours at room temperature. This reaction solution was vacuum concentrated, and the residual substance obtained was dissolved in dichloromethane. This solution was washed with a saturated aqueous solution of sodium hydrogencarbonate and saturated saline. An organic layer was collected and dried with anhydrous sodium sulfate. The organic layer was filtered, and the filtrate obtained was vacuum concentrated. The residual substance obtained was purified by subjecting it to reverse-phase silica gel column chromatography. At this time, the eluent used was a mixed solvent of acetone and water, containing 0.1% pyridine, and the mixing ratio between the acetone and water was changed stepwise. Specifically, the molar ratio between the acetone and water (acetone:water) was changed gradually so as to be 2:8, 3:7, 4:6, and 5:5 in this order. A fraction containing Compound 5 as a target compound was extracted with dichloromethane, and the thus-obtained organic layer was dried with anhydrous sodium sulfate. The organic layer was filtered, and the filtrate obtained was vacuum concentrated. Thus, Compound 5 (prolinol ureido amidite) was obtained (0.9 g, yield: 49%). The result of NMR analysis with respect to this compound is shown below.

$^1$H-NMR (CDCl$_3$): δ7.40-7.14 (9H, m, Ar—H), 6.82 (4H, m, Ar—H), 3.78 (s, 6H, OCH$_3$), 3.68-3.25 (9H, m, CH$_2$NH, CH$_2$OH, H-2, H-5, H-6), 1.74-1.18 (16H, m, alkyl, H-3, H-4).

FAB-MS: 575 [M+H]$^+$.

(3) Amidite Derivatives Having Prolinol (Compounds 6 and 7)

As a modified prolinol, the thus-obtained Compound 4 (0.80 g, 1.4 mmol) was dissolved in acetonitrile, and the resultant mixture was azeotropically dried three times at room temperature. The residual substance obtained was dissolved in 1 ml of acetonitrile, and the solution was placed under argon. Diisopropylammonium tetrazolide (0.24 g, 1.4 mmol) was added to this acetonitrile solution, thus providing a reaction solution. On the other hand, 2-cyanoethyl N,N,N', N'-tetraisopropyl phosphorodiamidite (0.50 g, 1.7 mmol) was dissolved in 1 ml of acetonitrile. This was added to the reaction solution, and the resultant mixture was stirred for 4 hours at room temperature. Dichloromethane was added to the reaction solution, and the resultant mixture was washed with a saturated aqueous solution of sodium hydrogencarbonate and saturated saline. An organic layer collected after the washing was dried with anhydrous sodium sulfate. The organic layer was filtered, and the filtrate obtained was Vacuum concentrated. The residual substance obtained was applied to amino silica gel column chromatography (the eluent: hexane:acetone=10:1, containing 0.1% pyridine). Thus, purified Compound 6 (DMTr-urethane-L-prolinol amidite) was obtained (0.90 g, yield: 83%). The result of NMR analysis with respect to this compound is shown below.

$^1$H-NMR (CDCl$_3$): δ7.40-7.14 (9H, m, Ar—H), 6.82 (4H, d, J=8.6 Hz, Ar—H), 4.24-3.94 (2H, m, COOCH$_2$), 3.78 (s, 6H, OCH$_3$), 3.72-2.96 (11H, m, CH$_2$O, POCH$_2$, CHCH$_3$, H-2, H-5, H-6), 2.58 (2H, m, CH$_2$CN), 2.10-1.46 (16H, m, alkyl, H-3, H-4), 1.34-1.10 (12H, m, CHCH$_3$). $^{31}$P-NMR (CD$_3$CN) δ 146.82.

FAB-MS: 776 [M+H]$^+$.

Purified Compound 7 (DMTr-ureido-L-prolinol amidite) (0.80 g, yield: 74%) was obtained in the same manner as in the above, except that, as the modified prolinol, Compound 5 was used instead of Compound 4. The result of NMR analysis with respect to this compound is shown below.

$^1$H-NMR (CDCl$_3$): δ7.40-7.14 (9H, m, Ar—H), 6.82 (4H, m, Ar—H), 3.78 (s, 6H, OCH$_3$), 3.63-3.25 (13H, m, CH$_2$O, POCH$_2$, CHCH$_3$, H-2, CH$_2$NH, CH$_2$OH, H-2, H-5, H-6), 2.73 (2H, m, CH$_2$CN), 2.10-1.48 (16H, m, alkyl, H-3, H-4), 1.35-1.10 (12H, m, CHCH$_3$).

$^{31}$P-NMR (CD$_3$CN) δ 146.83.

FAB-MS: 775 [M+H]$^+$.

While the present invention has been described above with reference to illustrative embodiments and examples, the present invention is by no means limited thereto. Various changes and modifications that may become apparent to those skilled in the art may be made in the configuration and specifics of the present invention without departing from the scope of the present invention.

This application claims priority from: Japanese Patent Application No. 2010-156122 filed on Jul. 8, 2010; Japanese Patent Application No. 2010-230808 filed on Oct. 13, 2010; Japanese Patent Application No. 2010-269824 filed on Dec. 2, 2010; Japanese Patent Application No. 2010-174915 filed on Aug. 3, 2010; Japanese Patent Application No. 2010-230806 filed on Oct. 13, 2010; and Japanese Patent Application No. 2010-269823 filed on Dec. 2, 2010. The entire disclosures of these Japanese Patent Applications are incorporated herein by reference.

INDUSTRIAL APPLICABILITY

According to the single-stranded nucleic acid molecule of the present invention, it is possible to inhibit the expression of a gene. Moreover, since the single-stranded nucleic acid molecule is not circular, it can be synthesized easily. Also, since it is a single strand, an annealing step as required in the production of a double strand is not necessary, so that it can be produced efficiently. As described above, since the ssNc molecule of the present invention can inhibit the expression of a target gene, it is useful as, for example, a pharmaceutical, a diagnostic agent, an agricultural chemical, and a tool for conducting research on agricultural chemicals, medical science, life science, and the like.

[Sequence Listing]
TF11005WO.ST25.txt

The invention claimed is:

1. A single-stranded nucleic acid molecule comprising:
an expression inhibitory sequence that inhibits expression of a target gene, wherein
the single-stranded nucleic acid molecule comprises, in sequence from a 5' side to a 3' side: a 5' side region (Xc); a linker region (Lx); an inner 5' side region (X); an inner 3' side region (Y); a linker region (Ly); and a 3' side region (Yc), the 5' end and the 3' end of the single-stranded nucleic acid molecule are not linked to each other,
the 5' side region (Xc) and the inner 5' side region (X) are linked to each other by the linker region (Lx), wherein the 5' side region (Xc) has 1 to 29 bases,
the 3' side region (Yc) and the inner 3' side region (Y) are linked to each other by the linker region (Ly), wherein the 3' side region (Yc) has 1 to 29 bases,
a inner region (Z) consists of the inner 5' side region (X) and the inner 3' side region (Y) that are linked to each other, and has 19 to 30 bases,
the 5' side region (Xc) is complementary to the inner 5' side region (X),
the 3' side region (Yc) is complementary to the inner 3' side region (Y), and
the inner region (Z), comprises the expression inhibitory sequence, and the expression inhibitory sequence is a ribonucleic acid (RNA) molecule.

2. The single-stranded nucleic acid molecule according to claim 1, wherein the number of bases (Z) in the inner region (Z), the number of bases (X) in the inner 5' side region (X), the number of bases (Y) in the inner 3' side region (Y), the number of bases (Xc) in the 5' side region (Xc), and the number of bases (Yc) in the 3' side region (Yc) satisfy conditions of Expressions (1) and (2):

$$Z=X+Y \quad (1)$$

$$Z \geq Xc+Yc \quad (2).$$

3. The single-stranded nucleic acid molecule according to claim 1, wherein the number of bases (X) in the inner 5' side region (X), the number of bases (Xc) in the 5' side region (Xc), the number of bases (Y) in the inner 3' side region (Y), and the number of bases (Yc) in the 3' side region (Yc) satisfy any of conditions (a) to (d):

(a) Conditions of Expressions (3) and (4) are satisfied;

$$X>Xc \quad (3)$$

$$Y=Yc \quad (4)$$

(b) Conditions of Expressions (5) and (6) are satisfied;

$$X=Xc \quad (5)$$

$$Y>Yc \quad (6)$$

(c) Conditions of Expressions (7) and (8) are satisfied;

$$X>Xc \quad (7)$$

$$Y>Yc \quad (8)$$

(d) Conditions of Expressions (9) and (10) are satisfied;

$$X=Xc \quad (9)$$

$$Y=Yc \quad (10).$$

4. The single-stranded nucleic acid molecule according to claim 3, wherein, in the conditions (a) to (d), the difference between the number of bases (X) in the inner 5' side region (X) and the number of bases (Xc) in the 5' side region (Xc), and the difference between the number of bases (Y) in the inner 3' side region (Y) and the number of bases (Yc) in the 3' side region (Yc) satisfy the following conditions:

(a) Conditions of Expressions (11) and (12) are satisfied;

$$X-Xc=1, 2 \text{ or } 3 \quad (11)$$

$$Y-Yc=0 \quad (12)$$

(b) Conditions of Expressions (13) and (14) are satisfied;

$$X-Xc=0 \quad (13)$$

$$Y-Yc=1, 2 \text{ or } 3 \quad (14)$$

(c) Conditions of Expressions (15) and (16) are satisfied;

$$X-Xc=1, 2 \text{ or } 3 \quad (15)$$

$$Y-Yc=1, 2 \text{ or } 3 \quad (16)$$

(d) Conditions of Expressions (17) and (18) are satisfied;

$$X-Xc=0 \quad (17)$$

$$Y-Yc=0 \quad (18).$$

5. The single-stranded nucleic acid molecule according to claim 1, wherein the number of bases (Xc) in the 5' side region (Xc) is 1 to 11.

6. The single-stranded nucleic acid molecule according to claim 5, wherein the number of bases (Xc) in the 5' side region (Xc) is 1 to 7.

7. The single-stranded nucleic acid molecule according to claim 5, wherein the number of bases (Xc) in the 5' side region (Xc) is 1 to 3.

8. The single-stranded nucleic acid molecule according to claim 1, wherein the number of bases (Yc) in the 3' side region (Yc) 1 to 11.

9. The single-stranded nucleic acid molecule according to claim 8, wherein the number of bases (Yc) in the 3' side region (Yc) is 1 to 7.

10. The single-stranded nucleic acid molecule according to claim 8, wherein the number of bases (Yc) in the 3' side region (Yc) is 1 to 3.

11. The single-stranded nucleic acid molecule according to claim 1, wherein the single-stranded nucleic acid molecule comprises at least one modified residue.

12. The single-stranded nucleic acid molecule according to claim 1, further comprising a labeling substance.

13. The single-stranded nucleic acid molecule according to claim 1, further comprising a stable isotope.

14. The single-stranded nucleic acid molecule according to claim 1, which is an RNA molecule.

15. The single-stranded nucleic acid molecule according to claim 1, wherein the linker region (Lx) and/or the linker region (Ly) is composed of at least one of a nucleotide residue and a non-nucleotide residue.

16. The single-stranded nucleic acid molecule according to claim 15, wherein the nucleotide residue is an unmodified nucleotide residue and/or a modified nucleotide residue.

17. The single-stranded nucleic acid molecule according to claim 15, wherein the linker region (Lx) and/or the linker region (Ly) is composed of any of residues (1) to (7):
  (1) an unmodified nucleotide residue
  (2) a modified nucleotide residue
  (3) an unmodified nucleotide residue and a modified nucleotide residue
  (4) a non-nucleotide residue
  (5) a non-nucleotide residue and an unmodified nucleotide residue
  (6) a non-nucleotide residue and a modified nucleotide residue
  (7) a non-nucleotide residue, an unmodified nucleotide residue, and a modified nucleotide residue.

18. The single-stranded nucleic acid molecule according to claim 1, wherein the total number of bases in the single-stranded nucleic acid molecule is 50 or more.

19. The single-stranded nucleic acid molecule according to claim 1, wherein expression of the gene is inhibited by RNA interference.

20. The single-stranded nucleic acid molecule according to claim 1, wherein a base sequence of the single-stranded nucleic acid molecule is any of SEQ ID NOs: 2, 7, 8, 13, 14, 29 to 35, 37, 43, 44, 47, 48, and 51 to 80.

21. A composition for inhibiting expression of a target gene, the composition comprising: the single-stranded nucleic acid molecule according to claim 1.

22. A pharmaceutical composition comprising: the single-stranded nucleic acid molecule according to claim 1.

23. A method for inhibiting expression of a target gene, the method comprising the step of: using the single-stranded nucleic acid molecule according to claim 1.

24. The method according to claim 23, comprising the step of: administering the single-stranded nucleic acid molecule to a cell, a tissue, or an organ.

25. The method according to claim 24, wherein the single-stranded nucleic acid molecule is administered in vivo or in vitro.

26. The method according to claim 23, wherein expression of the gene is inhibited by RNA interference.

27. A method for inducing RNA interference that inhibits expression of a target gene, the method comprising the step of: using the single-stranded nucleic acid molecule according to claim 1.

28. The single-stranded nucleic acid molecule according to claim 1, wherein the linker region (Lx) and/or the linker region (Ly) has 3 to 50 bases and at least one non-nucleotide residue.

29. The single-stranded nucleic acid molecule according to claim 1, wherein the expression inhibitory sequence inhibits expression of a GAPDH gene, TGF-$\beta$1 gene, LAMA1 gene, or LMNA gene.

30. A method of treating an acute lung injury comprising administering the single-stranded nucleic acid molecule according to claim 1 to a patient, wherein the single-stranded nucleic acid molecule comprises, as the expression inhibitory sequence, a sequence that inhibits expression of a TGF-$\beta$1 gene expressed during the acute lung injury.

* * * * *